(12) United States Patent
Shen et al.

(10) Patent No.: US 11,497,198 B2
(45) Date of Patent: Nov. 15, 2022

(54) GENETICALLY MODIFIED MICE EXPRESSING HUMANIZED CD40

(71) Applicant: Biocytogen Pharmaceuticals (Beijing) Co., Ltd., Beijing (CN)

(72) Inventors: Yuelei Shen, Beijing (CN); Chaoshe Guo, Beijing (CN); Rui Huang, Beijing (CN); Lei Zhao, Beijing (CN); Yanan Guo, Beijing (CN); Yang Bai, Beijing (CN); Meiling Zhang, Beijing (CN); Jiawei Yao, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

(21) Appl. No.: 16/435,453

(22) Filed: Jun. 7, 2019

(65) Prior Publication Data

US 2019/0343098 A1 Nov. 14, 2019

Related U.S. Application Data

(63) Continuation of application No. PCT/CN2018/091845, filed on Jun. 19, 2018.

(30) Foreign Application Priority Data

| Jun. 19, 2017 | (CN) | 201710464564.4 |
| Sep. 25, 2017 | (CN) | 201710872886.2 |
| Jun. 15, 2018 | (CN) | 201810622839.7 |

(51) Int. Cl.
*A01K 67/027* (2006.01)
*A61K 49/00* (2006.01)

(52) U.S. Cl.
CPC .... *A01K 67/0278* (2013.01); *A01K 2217/072* (2013.01); *A01K 2227/105* (2013.01); *A01K 2267/03* (2013.01)

(58) Field of Classification Search
None
See application file for complete search history.

(56) References Cited

U.S. PATENT DOCUMENTS

| 4,683,195 A | 7/1987 | Mullis et al. |
| 5,824,837 A * | 10/1998 | Chen .................. A01K 67/0278 800/3 |
| 2015/0106961 A1 | 4/2015 | Rojas et al. |

FOREIGN PATENT DOCUMENTS

| CN | 106604635 | 4/2017 |
| WO | WO 2014070934 | 5/2014 |
| WO | WO 2016175285 | 11/2016 |
| WO | WO 2018001241 | 1/2018 |
| WO | WO 2018041118 | 3/2018 |
| WO | WO 2018041119 | 3/2018 |
| WO | WO 2018041120 | 3/2018 |
| WO | WO 2018041121 | 3/2018 |
| WO | WO 2018068756 | 4/2018 |
| WO | WO 2018086583 | 5/2018 |
| WO | WO 2018086594 | 5/2018 |
| WO | WO 2018121787 | 7/2018 |
| WO | WO 2018177440 | 10/2018 |
| WO | WO 2018177441 | 10/2018 |

OTHER PUBLICATIONS

Denning and Priddle (Reproduction 126:1-11.2003 (Year: 2003).*
Brevini, 2010, Theriogenology, vol. 74, pp. 544-550, (Year: 2010).*
Munoz, (Stem Cell Rev and Rep (2009) 5:6-9 (Year: 2009).*
Ahonen (Nature Immunology, 3(5): 451-456, 2002). (Year: 2002).*
Dahan, (Cancer Cell 29, 820-831, 2016). (Year: 2016).*
Bulliard (abstract, 2014). (Year: 2014).*
Ristevski (Molecular Biotechnology, 29: 153-157, 2005) (Year: 2005).*
Gama Sosa, (Brain Struct Funct (2010) 214:91-109) (Year: 2010).*
Smith (Journal of Biotechnology, 99: 1-22, 2002) (Year: 2002).*
Qi, (Hypertension, 45:1004-1011, 2005) (Year: 2005).*
Hong (Stem Cells and Development, 21(9): 1-16, 2012) (Year: 2012).*
Khodarovich (Applied Biochemistry and Microbiology, 49(9): 711-722, 2013) (Year: 2013).*
Guo (Cell Research, 25: 767-768, 2005) (Year: 2005).*
Dow et al (Trends in Molecular Medicine, 2015, 21, 609-621) (Year: 2015).*
Kosicki et al (Nature Biotechnology, 2018, 1-8) (Year: 2018).*
Dow (Trends in Molecular Medicine, 2015, 21, 609-621 (Year: 2015).*
Kosicki (Nature Biotechnology, 2018, 1-8) (Year: 2018).*
Tong (Nature Protocols, 6(6): 827-844, 2011 (Year: 2011).*
Zhu (Nature Communications, 1-13, 2919) (Year: 2019).*
Ai et al., "Establishment of a human sCD40L transgenic mouse model," Acta Laboratorium Animalis Scientia Sinica, 2012, 20(4):35-40.
Beatty et al., "CD40 agonists alter tumor stroma and show efficacy against pancreatic carcinoma in mice and humans," Science, 2011, 331(6024):1612-1616.
International Search Report and Written Opinion in International Appln. No. PCT/CN2018/091845, dated Sep. 4, 2018, 12 pages.
Inui et al., "Identification of the intracytoplasmic region essential for signal transduction through a B cell activation molecule, CD40," Eur. J. Immunol., 1990, 20(31):1747-1753.
Ito et al., "NOC/SCID ycnull mouse: an excellent recipient mouse model for engraftment of human cells," Blood, 2002, 100(9):3175-3182.
Nova-Lamperti et al., "tumor necrosis factor receptor superfamily member 5 isoform 1 precursor [Homo sapiens], NCBI Reference Sequence: NP_001241.1," NCBI GenBank, Jun. 15, 2017, 4 pages.

(Continued)

*Primary Examiner* — Anoop K Singh
*Assistant Examiner* — Magdalene K Sgagias
(74) *Attorney, Agent, or Firm* — Fish & Richardson P.C.

(57) ABSTRACT

The present disclosure relates to genetically modified non-human animals that express a human or chimeric (e.g., humanized) CD40, and methods of use thereof.

4 Claims, 20 Drawing Sheets

Specification includes a Sequence Listing.

(56) References Cited

OTHER PUBLICATIONS

Strausberg et al., "Cd40 protein [*Mus musculus*], GenBank accession No. AAH29254.1," NCBI GenBank, Oct. 20, 2006, 2 pages.

Vonderheide et al., "Agonistic CD40 antibodies and cancer therapy," 2013, 1035-1043.

Vonderheide et al., "Clinical activity and immune modulation in cancer patients treated with CP-870,893, a novel CD40 agonist monoclonal antibody," Journal of Clinical Oncology, 2007, 25(7):876-883.

Yasui et al., "Dissection of B cell differentiation during primary immune responses in mice with altered CD40 signals," International Immunology, 2002, 14(3):379-329.

Yin et al., "Delivery technologies for genome editing," Nature Reviews Drug Discovery, 2017, 16(6):387-399.

Brehm, "Generation of improved humanized mouse models for human infectious diseases," J. Immunol. Methods, 2014, 410:3-17.

Dahan, "Therapeutic Activity of Agonistic, Human Anli-CD40 Monoclonal Antibod.ics Requires Selective FcyR Engagement," Cancer Cell, 2016, 26(6):820-831.

Mangsbo, "The Human Agonistic CD40 Antibody ADC-J 013 Eradicates Bladder Tumors and Generates T-cell-Dependent Tumor Immunity," Clin. Cancer Res., 2014, 21(5):1115-1126.

Lu et al., "Research and Application Progress of Humanized Mouse Models," Medical Recapitulate, Sep. 2014, 20(18):3281-3284 (with English abstract).

\* cited by examiner

FIG. 20

| Score | Expect | Method | Identities | Positives | Gaps |
|---|---|---|---|---|---|
| 357 bits(917) | 1e-129 | Compositional matrix adjust. | 172/281(61%) | 211/281(75%) | 7/281(2%) |

```
Mouse    1   MVSLPRLCALWGCLLTAVHLGQCVTCSDKQYLHDGQCCDLCQPGSRLTSHCTALEKTQCH    60
             MV LP  C LWGCLLTAVH       C +KQYL + QCC LCQPG +L S CT    +T+C
Human    1   MVRLPLQCVLWGCLLTAVHPEPPTACREKQYLINSQCCSLCQPGQKLVSDCTEFTETECL    60

Mouse   61   PCDSGEFSAQWNREIRCHQHRHCEPNQGLRVKKEGTAESDTVCTCKEGQHCTSKDCEACA   120
             PC   EF   WNRE  CHQH++C+PN GLRV+++GT+E+DT+CTC+EG HCTS+ CE+C
Human   61   PCGESEFLDTWNRETHCHQHKYCDPNLGLRVQQKGTSETDTICTCEEGWHCTSEACESCV   120

Mouse  121   QHTPCIPGFGVMEMATETTDTVCHPCPVGFFSNQSSLFEKCYPWTSCEDKNLEVLQKGTS   180
             H C PGFGV ++AT   +DT+C PCPVGFFSN SS FEKC+PWTSCE K+L V Q GT+
Human  121   LHRSCSPGFGVKQIATGVSDTICEPCPVGFFSNVSSAFEKCHPWTSCETKDLVVQQAGTN   180

Mouse  181   QTNVICGLKSRMRALLVIPVVMGILITIFGVFLYIKKVVKKPKDNEILPPAARRQDPQEM   240
             +T+V+CG + R+RAL+VIP++ GIL  I  V ++IKKV KKP +    P    +Q+PQE+
Human  181   KTDVVCGPQDRLRALVVIPIIFGILFAILLVLFIKKVAKKPTNKAPHP----KQEPQEI   236

Mouse  241   ---EDYPGHNTAAPVQETLHGCQPVTQEDGKESRISVQERQ   278
               +D  PG NTAAPVQETLHGCQPVTQEDGKESRISVQERQ
Human  237   NFPDDLPGSNTAAPVQETLHGCQPVTQEDGKESRISVQERQ   277
```

GENETICALLY MODIFIED MICE EXPRESSING HUMANIZED CD40

CLAIM OF PRIORITY

This application is a continuation of and claims priority to international Application No. PCT/CN2018/091845, filed on Jun. 19, 2018, which claims the benefit of Chinese Patent Application App. No. 201710464564.4, filed on Jun. 19, 2017, Chinese Patent Application App. No. 201710872886.2, filed on Sep. 25, 2017, and Chinese Patent Application App. No. 201810622839.7 filed on Jun. 15, 2018. The entire contents of the foregoing are incorporated herein by reference.

TECHNICAL FIELD

This disclosure relates to genetically modified animal expressing human or chimeric (e.g., humanized) CD40, and methods of use thereof.

BACKGROUND

The immune system has developed multiple mechanisms to prevent deleterious activation of immune cells. One such mechanism is the intricate balance between positive and negative costimulatory signals delivered to immune cells. Targeting the stimulatory or inhibitory pathways for the immune system is considered to be a potential approach for the treatment of various diseases, e.g., cancers and autoimmune diseases.

The traditional drug research and development for these stimulatory or inhibitory receptors typically use in vitro screening approaches. However, these screening approaches cannot provide the body environment (such as tumor microenvironment, stromal cells, extracellular matrix components and immune cell interaction, etc.), resulting in a higher rate of failure in drug development. In addition, in view of the differences between humans and animals, the test results obtained from the use of conventional experimental animals for in vivo pharmacological test may not reflect the real disease state and the interaction at the targeting sites, resulting in that the results in many clinical trials are significantly different from the animal experimental results. Therefore, the development of humanized animal models that are suitable for human antibody screening and evaluation will significantly improve the efficiency of new drug development and reduce the cost for drug research and development.

SUMMARY

This disclosure is related to an animal model with human CD40 or chimeric CD40. The animal model can express human CD40 or chimeric CD40 (e.g., humanized CD40) protein in its body. It can be used in the studies on the function of CD40 gene, and can be used in the screening and evaluation of anti-human CD40 antibodies. In addition, the animal models prepared by the methods described herein can be used in drug screening, pharmacodynamics studies, treatments for immune-related diseases (e.g., autoimmune disease), and cancer therapy for human CD40 target sites; they can also be used to facilitate the development and design of new drugs, and save time and cost. In summary, this disclosure provides a powerful tool for studying the function of CD40 protein and a platform for screening cancer drugs.

In one aspect, the disclosure relates to genetically-modified, non-human animals whose genome comprises at least one chromosome comprising a sequence encoding a human or chimeric CD40. In some embodiments, the sequence encoding the human or chimeric CD40 is operably linked to an endogenous regulatory element at the endogenous CD40 gene locus in the at least one chromosome. In some embodiments, the sequence encoding a human or chimeric CD40 comprises a sequence encoding an amino acid sequence that is at least 50%, 55%, 65%, 70%, 75%, 80%, 85%, 90%, 95%, 99%, or 100% identical to human CD40 (NP_001241.1 (SEQ ID NO: 23)). In some embodiments, the sequence encoding a human or chimeric CD40 comprises a sequence encoding an amino acid sequence that is at least 50%, 55%, 65%, 70%, 75%, 80%, 85%, 90%, 95%, 99%, or 100% identical to SEQ ID NO: 27. In some embodiments, the sequence encoding a human or chimeric CD40 comprises a sequence encoding an amino acid sequence that corresponds to amino acids 20-192 of SEQ ID NO: 23.

In some embodiments, the animal is a mammal, e.g., a monkey, a rodent or a mouse. In some embodiments, the animal is a C57BL/6 mouse. In some embodiments, the animal does not express endogenous CD40. In some embodiments, the animal has one or more cells expressing human or chimeric CD40. In some embodiments, the expressed human or chimeric CD40 can bind to or interact with human protein CD40L (also known as CD154). In some embodiments, the expressed human or chimeric CD40 can bind to or interact with endogenous CD154.

In one aspect, the disclosure relates to genetically-modified, non-human animals, wherein the genome of the animals comprises a replacement, at an endogenous CD40 gene locus, of a sequence encoding a region of endogenous CD40 with a sequence encoding a corresponding region of human CD40. In some embodiments, the sequence encoding the corresponding region of human CD40 is operably linked to an endogenous regulatory element at the endogenous CD40 locus, and one or more cells of the animal expresses a chimeric CD40. In some embodiments, the animal does not express endogenous CD40. In some embodiments, the locus of endogenous CD40 is the extracellular region of CD40. In some embodiments, the animal has one or more cells expressing a chimeric CD40 having an extracellular region, a transmembrane region, and a cytoplasmic region, wherein the extracellular region comprises a sequence that is at least 50%, 60%, 70%, 80%, 90%, 95%, or 99% identical to the extracellular region of human CD40. In some embodiments, the extracellular region of the chimeric CD40 has a sequence that has at least 10, 20, 30, 40, 50, 60, 70, 80, 90, 100, 110, 120, 130, 140, 150, 160, 170, or 180 contiguous amino acids that are identical to a contiguous sequence present in the extracellular region of human CD40. In some embodiments, the animal is a mouse, and the sequence encoding the region of endogenous CD40 is exon 2, exon 3, exon 4, exon 5, exon 6, and/or exon 7 of the endogenous mouse CD40 gene. In some embodiments, the animal is heterozygous with respect to the replacement at the endogenous CD40 gene locus. In some embodiments, the animal is homozygous with respect to the replacement at the endogenous CD40 gene locus.

In one aspect, the disclosure relates to methods for making a genetically-modified, non-human animal. The methods involve replacing in at least one cell of the animal, at an endogenous CD40 gene locus, a sequence encoding a region of an endogenous CD40 with a sequence encoding a corresponding region of human CD40. In some embodiments, the sequence encoding the corresponding region of human CD40 comprises exon 1, exon 2, exon 3, exon 4, exon 5, exon 6, exon 7, exon 8, and/or exon 9 of a human CD40 gene. In some embodiments, the sequence encoding the corresponding region of CD40 comprises exon 2, exon 3, exon 4, exon 5, exon 6, and/or exon 7 (or part thereof, e.g., part of exon 2 and/or exon 7) of a human CD40 gene. In some embodiments, the sequence encoding the corresponding region of human CD40 encodes amino acids 20-192 of SEQ ID NO: 23. In some embodiments, the region is located within the extracellular region of CD40. In some embodiments, the animal is a mouse, and the sequence encoding the region of the endogenous CD40 locus is exon 2, exon 3, exon 4, exon 5, exon 6, and/or exon 7 of mouse CD40 gene (e.g., part of exon 2, exon 3, exon 4, exon 5, exon 6, and part of exon 7).

In one aspect, the disclosure relates to non-human animals comprising at least one cell comprising a nucleotide sequence encoding a chimeric CD40 polypeptide, wherein the chimeric CD40 polypeptide comprises at least 50 contiguous amino acid residues that are identical to the corresponding contiguous amino acid sequence of a human CD40, wherein the animal expresses the chimeric CD40. In some embodiments, the chimeric CD40 polypeptide has at least 50 contiguous amino acid residues that are identical to the corresponding contiguous amino acid sequence of a human CD40 extracellular region. In some embodiments, the chimeric CD40 polypeptide comprises a sequence that is at least 90%, 95%, or 99% identical to amino acids 20-192 of SEQ ID NO: 23. In some embodiments, the nucleotide sequence is operably linked to an endogenous CD40 regulatory element of the animal. In some embodiments, the chimeric CD40 polypeptide comprises an endogenous CD40 transmembrane region and/or an endogenous CD40 cytoplasmic region. In some embodiments, the nucleotide sequence is integrated to an endogenous CD40 gene locus of the animal. In some embodiments, the chimeric CD40 has at least one mouse CD40 activity (e.g., interacting with mouse CD154, and promoting immune responses in mice) and/or at least one human CD40 activity (e.g., interacting with human CD154, and promoting immune responses in human).

In one aspect, the disclosure relates to methods of making a genetically-modified mouse cell that expresses a chimeric CD40, the method including: replacing, at an endogenous mouse CD40 gene locus, a nucleotide sequence encoding a region of mouse CD40 with a nucleotide sequence encoding a corresponding region of human CD40, thereby generating a genetically-modified mouse cell that includes a nucleotide sequence that encodes the chimeric CD40, wherein the mouse cell expresses the chimeric CD40. In some embodiments, the chimeric CD40 comprises a signal peptide sequence (e.g., a mouse signal peptide sequence or a human signal peptide sequence), an extracellular region of mouse CD40, an extracellular region of human CD40, a transmembrane and/or a cytoplasmic region of a mouse CD40. In some embodiments, the nucleotide sequence encoding the chimeric CD40 is operably linked to an endogenous CD40 regulatory region, e.g., promoter.

In some embodiments, the animals further comprise a sequence encoding an additional human or chimeric protein. In some embodiments, the additional human or chimeric protein is programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD47, CD137, CD154, T-Cell Immunoreceptor With Ig And ITIM Domains (TIGIT), Glucocorticoid-Induced TNFR-Related Protein (GITR), T-cell immunoglobulin and mucin-domain containing-3 (TIM-3), Signal regulatory protein α (SIRPα) or TNF Receptor Superfamily Member 4 (TNFRSF4 or OX40).

In one aspect, the disclosure relates to methods of determining effectiveness of an anti-CD40 antibody for the treatment of cancer, including: administering the anti-CD40 antibody to the animal as described herein, wherein the animal has a tumor, and determining the inhibitory effects of the anti-CD40 antibody to the tumor. In some embodiments, the animal has one or more cells (e.g., antigen presenting cells (APC)) that express CD40. In some embodiments, the animal has one or more tumor cells that express CD40.

In some embodiments, the tumor comprises one or more cancer cells that are injected into the animal. In some embodiments, determining the inhibitory effects of the anti-CD40 antibody to the tumor involves measuring the tumor volume in the animal. In some embodiments, the tumor cells are melanoma cells (e.g., advanced melanoma cells), non-small cell lung carcinoma (NSCLC) cells, small cell lung cancer (SCLC) cells, bladder cancer cells, non-Hodgkin lymphoma cells, and/or prostate cancer cells (e.g., metastatic hormone-refractory prostate cancer). In some embodiments, the tumor cells are hepatocellular, ovarian, colon, or cervical tumor cells. In some embodiments, the tumor cells are breast cancer cells, ovarian cancer cells, and/or solid tumor cells. In some embodiments, the tumor cells are lymphoma cells, colorectal cancer cells, or oropharyngeal cancer cells. In some embodiments, the animal has metastatic solid tumors, NSCLC, melanoma, lymphoma (e.g., non-Hodgkin lymphoma), colorectal cancer, or multiple myeloma. In some embodiments, the animal has melanoma, pancreatic carcinoma, mesothelioma, hematological malignancies (e.g., Non-Hodgkin's lymphoma, lymphoma, chronic lymphocytic leukemia), or solid tumors.

In one aspect, the disclosure relates to methods of determining effectiveness of an anti-CD40 antibody for the treatment of various immune-related disorders, e.g., autoimmune diseases.

In one aspect, the disclosure relates to methods of determining effectiveness of an anti-CD40 antibody and an additional therapeutic agent for the treatment of a tumor, including administering the anti-CD40 antibody and the additional therapeutic agent to the animal as described herein, wherein the animal has a tumor, and determining the inhibitory effects on the tumor. In some embodiments, the animal or mouse further comprises a sequence encoding an additional human or chimeric protein. In some embodiments, the additional human or chimeric protein is PD-1, CTLA-4, LAG-3, BTLA, PD-L1, CD27, CD28, CD47, CD137, CD154, TIGIT, TIM-3, GITR, SIRPα or OX40. In some embodiments, the animal further comprises a sequence encoding a human or chimeric PD-1, PD-L1, or CTLA-4.

In some embodiments, the additional therapeutic agent is an antibody (e.g., human antibody) the specifically binds to PD-1, CTLA-4, LAG-3, BTLA, PD-L1, CD27, CD28, CD47, CD137, CD154, TIGIT, TIM-3, GITR, SIRPα, OX40, CD20, EGFR, or CD319. In some embodiments, the additional therapeutic agent is an anti-PD-1 antibody (e.g., nivolumab), an anti-PD-L1 antibody, an anti-CTLA4 antibody (e.g., ipilimumab), an anti-CD20 antibody (e.g., rituximab), an anti-EGFR antibody (e.g., cetuximab), or an anti-CD319 antibody (e.g., elotuzumab).

In some embodiments, the animal comprises one or more cells (e.g., antigen presenting cells, B cells, macrophages, dendritic cells, or tumor cells) that express CD40. In some embodiments, the animal comprises one or more cells (e.g., T cells) that express CD154. In some embodiments, the tumor comprises one or more tumor cells that express CD40. In some embodiments, the tumor comprises one or more tumor cells that express PD-L1, PD-L2, CD80 or CD86. In some embodiments, the tumor is caused by injection of one or more cancer cells into the animal. In some embodiments, determining the inhibitory effects of the treatment involves measuring the tumor volume in the animal. In some embodiments, the tumor comprises melanoma cells, non-small cell lung carcinoma (NSCLC) cells, small cell lung cancer (SCLC) cells, bladder cancer cells, and/or prostate cancer cells (e.g., metastatic hormone-refractory prostate cancer cells). In some embodiments, the animal has metastatic solid tumors, NSCLC, melanoma, lymphoma (e.g., non-Hodgkin lymphoma), colorectal cancer, or multiple myeloma. In some embodiments, the animal has melanoma, pancreatic carcinoma, mesothelioma, hematological malignancies (e.g., Non-Hodgkin's lymphoma, lymphoma, chronic lymphocytic leukemia), or solid tumors.

In one aspect, the disclosure relates to proteins comprising an amino acid sequence, wherein the amino acid sequence is one of the following: (a) an amino acid sequence set forth in SEQ ID NO: 27; (b) an amino acid sequence that is at least 90% identical to SEQ ID NO: 27; (c) an amino acid sequence that is at least 91%, 92%, 93%, 94%, 95%, 96%, 97%, 98%, or 99% identical to SEQ ID NO: 27; (d) an amino acid sequence that is different from the amino acid sequence set forth in SEQ ID NO: 27 by no more than 10, 9, 8, 7, 6, 5, 4, 3, 2 or 1 amino acid; and (e) an amino acid sequence that comprises a substitution, a deletion and/or insertion of one, two, three, four, five or more amino acids to the amino acid sequence set forth in SEQ ID NO: 27. In some embodiments, provided herein are cells comprising the proteins disclosed herein. In some embodiments, provided herein are animals having the proteins disclosed herein.

In one aspect, the disclosure relates to nucleic acids comprising a nucleotide sequence, wherein the nucleotide sequence is one of the following: (a) a sequence that encodes the protein as described herein; (b) SEQ ID NO: 25; (c) SEQ ID NO: 26; (d) a sequence that is at least 90% identical to SEQ ID NO: 25 or SEQ ID NO: 26; (e) a sequence that is at least 91%, 92%, 93%, 94%, 95%, 96%, 97%, 98%, or 99% identical to SEQ ID NO: 25; and (f) a sequence that is at least 91%, 92%, 93%, 94%, 95%, 96%, 97%, 98%, or 99% identical to SEQ ID NO: 26. In some embodiments, provided herein are cells comprising the nucleic acids disclosed herein. In some embodiments, provided herein are animals having the nucleic acids disclosed herein.

In another aspect, the disclosure also provides a genetically-modified, non-human animal whose genome comprise a disruption in the animal's endogenous CD40 gene, wherein the disruption of the endogenous CD40 gene comprises deletion of exon 1, exon 2, exon 3, exon 4, exon 5, exon 6, exon 7, exon 8, and/or exon 9, or part thereof of the endogenous CD40 gene.

In some embodiments, the disruption of the endogenous CD40 gene comprises deletion of one or more exons or part of exons selected from the group consisting of exon 1, exon 2, exon 3, exon 4, exon 5, exon 6, exon 7, exon 8, and exon 9 of the endogenous CD40 gene.

In some embodiments, the disruption of the endogenous CD40 gene further comprises deletion of one or more introns or part of introns selected from the group consisting of intron 1, intron 2, intron 3, intron 4, intron 5, intron 6, intron 7, and intron 8 of the endogenous CD40 gene.

In some embodiments, wherein the deletion can comprise deleting at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, 300, 350, 400, 450, 500, 550, 600, 650, or more nucleotides.

In some embodiments, the disruption of the endogenous CD40 gene comprises the deletion of at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, or 300 nucleotides of exon 1, exon 2, exon 3, exon 4, exon 5, exon 6, exon 7, exon 8, and/or exon 9 (e.g., deletion of at least 300 nucleotides of exon 2 or exon 7).

In some embodiments, the mice described in the present disclosure can be mated with the mice containing other human or chimeric genes (e.g., chimeric SIRPα, chimeric PD-1, chimeric PD-L1, chimeric CTLA-4, or other immunomodulatory factors), so as to obtain a mouse expressing two or more human or chimeric proteins. The mice can also, e.g., be used for screening antibodies in the case of a combined use of drugs, as well as evaluating the efficacy of the combination therapy.

In another aspect, the disclosure further provides methods of determining toxicity of an agent (e.g., a CD40 antagonist or agonist). The methods involve administering the agent to the animal as described herein; and determining weight change of the animal. In some embodiments, the method further involve performing a blood test (e.g., determining red blood cell count).

In one aspect, the disclosure relates to a targeting vector, including a) a DNA fragment homologous to the 5' end of a region to be altered (5' arm), which is selected from the CD40 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the CD40 gene genomic DNAs in the length of 100 to 10,000 nucleotides.

In some embodiments, a) the DNA fragment homologous to the 5' end of a region to be altered (5' arm/receptor) is selected from the nucleotide sequences that have at least 90% homology to the NCBI accession number NC_000068.7; c) the DNA fragment homologous to the 3' end of the region to be altered (3' arm/receptor) is selected from the nucleotide sequences that have at least 90% homology to the NCBI accession number NC_000068.7.

In some embodiments, a) the DNA fragment homologous to the 5' end of a region to be altered (5' arm/receptor) is selected from the nucleotides from the position 165060750 to the position 165062291 of the NCBI accession number NC_000068.7; c) the DNA fragment homologous to the 3' end of the region to be altered (3' arm/receptor) is selected from the nucleotides from the position 165069646 to the position 165071120 of the NCBI accession number NC_000068.7.

In some embodiments, a length of the selected genomic nucleotide sequence is more than 3 kb, 3.5 kb, 4 kb, 4.5 kb, 5 kb, 5.5 kb, or 6 kb. In some embodiments, the length is about 6329 bp. In some embodiments, the region to be altered is exon 2, exon 3, exon 4, exon 5, exon 6, and/or exon 7 of mouse CD40 gene.

In some embodiments, the sequence of the 5' arm is shown in SEQ ID NO: 28. In some embodiments, the sequence of the 3' arm is shown in SEQ ID NO: 29.

In some embodiments, the targeting vector further includes a selectable gene marker.

In some embodiments, the target region is derived from human. The target region is a part or entirety of the nucleotide sequence of a humanized CD40. In some embodiments, the nucleotide sequence is shown as one or more of exon 2, exon 3, exon 4, exon 5, exon 6, and exon 7 of the human CD40.

In some embodiments, the nucleotide sequence of the human CD40 encodes the human CD40 protein with the NCBI accession number NP_001241.1 (SEQ ID NO: 23). In some emboldens, the nucleotide sequence of the human CD40 is selected from the nucleotides from the position 46121826 to the position 46128154 of NC_000020.11 (SEQ ID NO: 30).

The disclosure also relates to a cell including the targeting vector as described herein.

The disclosure also relates to a method for establishing a genetically-modified non-human animal expressing two human or chimeric (e.g., humanized) genes. The method includes the steps of (a) using the method for establishing a CD40 gene humanized animal model to obtain a CD40 gene genetically modified humanized mouse;

(b) mating the CD40 gene genetically modified humanized mouse obtained in step (a) with another humanized mouse, and then screening to obtain a double humanized mouse model.

In some embodiments, in step (b), the CD40 gene genetically modified humanized mouse obtained in step (a) is mated with a PD-1 or PD-L1 humanized mouse to obtain a CD40 and PD-1 double humanized mouse model or a CD40 and PD-L1 double humanized mouse model.

The disclosure also relates to non-human mammal generated through the methods as described herein.

In some embodiments, the genome thereof contains human gene(s).

In some embodiments, the non-human mammal is a rodent. In some embodiments, the non-human mammal is a mouse.

In some embodiments, the non-human mammal expresses a protein encoded by a humanized CD40 gene.

The disclosure also relates to an offspring of the non-human mammal.

In another aspect, the disclosure relates to a tumor bearing non-human mammal model, characterized in that the non-human mammal model is obtained through the methods as described herein.

In some embodiments, the non-human mammal is a rodent. In some embodiments, the non-human mammal is a mouse.

The disclosure also relates to a cell (e.g., stem cell or embryonic stem cell) or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

In one aspect, the disclosure relates to a CD40 amino acid sequence of a humanized mouse, wherein the amino acid sequence is selected from the group consisting of:

a) an amino acid sequence shown in SEQ ID NO: 27;

b) an amino acid sequence having a homology of at least 90% with the amino acid sequence shown in SEQ ID NO: 27;

c) an amino acid sequence encoded by a nucleic acid sequence, wherein the nucleic acid sequence is able to hybridize to a nucleotide sequence encoding the amino acid shown in SEQ ID NO: 27 under a low stringency condition or a strict stringency condition;

d) an amino acid sequence having a homology of at least 90%, 91%, 92%, 93%, 94%, 95%, 96%, 97%, 98%, or at least 99% with the amino acid sequence shown in SEQ ID NO: 27;

e) an amino acid sequence that is different from the amino acid sequence shown in SEQ ID NO: 27 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 27.

The disclosure also relates to a CD40 nucleic acid sequence of a humanized mouse, wherein the nucleic acid sequence is selected from the group consisting of:

a) a nucleic acid sequence that encodes the CD40 amino acid sequence of a humanized mouse;

b) a nucleic acid sequence that is set forth in SEQ ID NO: 25 or SEQ ID NO: 26;

c) a nucleic acid sequence that can hybridize to the nucleotide sequence as shown in SEQ ID NO: 25 or SEQ ID NO: 26 under a low stringency condition or a strict stringency condition;

d) a nucleic acid sequence that has a homology of at least 90%, 91%, 92%, 93%, 94%, 95%, 96%, 97%, 98%, or at least 99% with the nucleotide sequence as shown in SEQ ID NO: 25 or SEQ ID NO: 26;

f) a nucleic acid sequence that encodes an amino acid sequence, wherein the amino acid sequence has a homology of at least 90% with the amino acid sequence shown in SEQ ID NO: 27;

g) a nucleic acid sequence that encodes an amino acid sequence, wherein the amino acid sequence has a homology of at least 90%, 91%, 92%, 93%, 94%, 95%, 96%, 97%, 98%, or at least 99% with the amino acid sequence shown in SEQ ID NO: 27;

h) a nucleic acid sequence that encodes an amino acid sequence, wherein the amino acid sequence is different from the amino acid sequence shown in SEQ ID NO: 27 by no more than 10, 9, 8, 7, 6, 5, 4, 3, 2 or no more than 1 amino acid; and/or i) a nucleic acid sequence that encodes an amino acid sequence, wherein the amino acid sequence comprises a substitution, a deletion and/or insertion of 1, 2, 3, 4, 5, 6, 7, 8, 9, or more amino acids to the amino acid sequence shown in SEQ ID NO: 27.

The disclosure further relates to a CD40 genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the CD40 gene function, human CD40 antibodies, the drugs or efficacies for human CD40 targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 20 shows the alignment between mouse CD40 amino acid sequence (NP_035741.2; SEQ ID NO: 21) and human CD40 amino acid sequence (NP_001241.1; SEQ ID NO: 23).

DETAILED DESCRIPTION

Figure 1A:
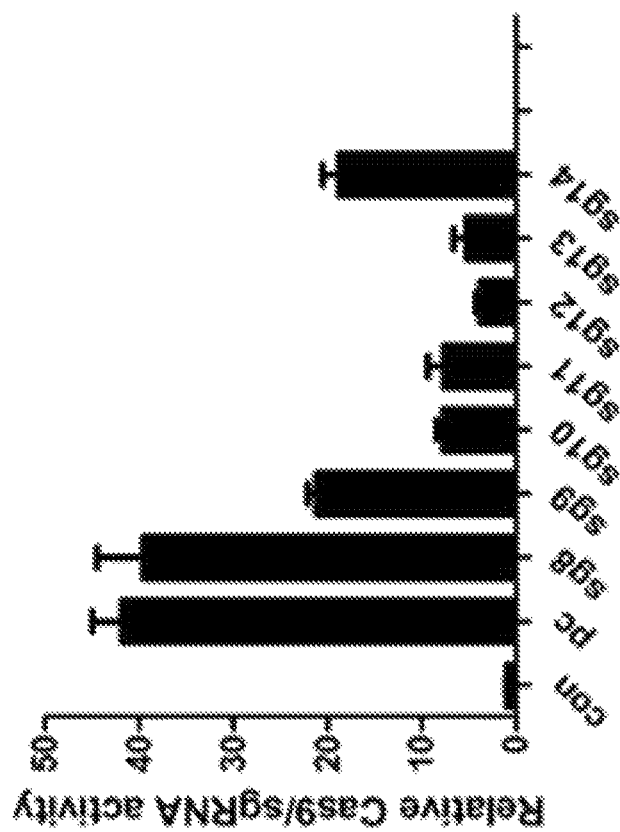
FIG. 1A is a graph showing activity testing results for sgRNA1-sgRNA7 (Con is a negative control; PC is a positive control).

This disclosure relates to transgenic non-human animal with human or chimeric (e.g., humanized) CD40, and methods of use thereof.

CD40 is a member of the TNF-receptor superfamily. It is a costimulatory protein found on antigen presenting cells and is required for their activation. This receptor has been found to be essential in mediating a broad variety of immune and inflammatory responses including T cell-dependent immunoglobulin class switching, memory B cell development, and germinal center formation. The binding of CD154 (CD40 ligand) on T cells to CD40 activates antigen presenting cells and induces a variety of downstream effects. CD154 is expressed primarily by activated T lymphocytes.

Like some other members of the TNF receptor family, CD40 signaling is mediated by adapter molecules rather than by inherent signal-transduction activity of the CD40 cytoplasmic tail. The TNFR-receptor associated factor adaptor proteins TRAF1, TRAF2, TRAF6 and possibly TRAF5 interact with CD40 and serve as mediators of the signal transduction.

CD40 is constitutively expressed by antigen presenting cells, including dendritic cells, B cells, and macrophages. It can also be expressed by endothelial cells, smooth muscle cells, fibroblasts and epithelial cells. Consistent with its widespread expression on normal cells, CD40 is also expressed on a wide range of tumor cells, including non-Hodgkin's and Hodgkin's lymphomas, myeloma and some carcinomas including nasopharynx, bladder, cervix, kidney and ovary.

In the macrophage, the primary signal for activation is IFN-γ from Th1 type CD4 T cells. The secondary signal is CD154 on the T cell which binds CD40 on the macrophage cell surface. As a result, the macrophage expresses more CD40 and TNF receptors on its surface which helps increase the level of activation of macrophages. The increase in activation can e.g., lead to the destruction of ingested microbe or tumor cells. The B cell can present antigens to helper T cells. If an activated T cell recognizes the peptide presented by the B cell, the CD154 on the T cell binds to the B cell's CD40 receptor, causing B cell activation. The T cell also produces IL-2, which directly influences B cells. As a result of this stimulation, the B cell can undergo division, antibody isotype switching, and differentiation to plasma cells. The end-result is a B cell that is able to mass-produce specific antibodies against an antigenic target. Thus, CD40 antibodies can be potentially used as cancer therapies.

Experimental animal models are an indispensable research tool for studying the effects of these antibodies (e.g., CD40 antibodies). Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models have various important applications. For example, due to the presence of human or humanized genes, the animals can express or express in part of the proteins with human functions, so as to greatly reduce the differences in clinical trials between humans and animals, and provide the possibility of drug screening at animal levels.

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered., 1985); Oligonucleotide Synthesis (M. J. Gaited., 1984); Mullis et al U.S. Pat. No. 4,683,195; Nucleic Acid Hybridization (B. D. Hames & S. J. Higginseds. 1984); Transcription And Translation (B. D. Hames & S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calosedes., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N.Y., 1986); each of which is incorporated herein by reference in its entirety.

CD40

CD40 (also known as Tumor Necrosis Factor Receptor Superfamily Member 5 or TNFRSF5) is a tumor necrosis factor receptor superfamily member expressed on antigen presenting cells (APC) such as dendritic cells (DC), macrophages, B cells, and monocytes as well as many non-immune cells and a wide range of tumors. Interaction with its trimeric ligand CD154 on activated T helper cells results in APC activation, leading to the induction of adaptive immunity.

Physiologically, signaling via CD40 on APC is thought to represent a major component of T cell help and mediates in large part the capacity of helper T cells to license APC. Ligation of CD40 on DC, for example, induces increased surface expression of costimulatory and MHC molecules, production of proinflammatory cytokines, and enhanced T cell triggering. CD40 ligation on resting B cells increases antigen-presenting function and proliferation.

In pre-clinical models, rat anti-mouse CD40 mAb show remarkable therapeutic activity in the treatment of CD40+ B-cell lymphomas (with 80-100% of mice cured and immune to re-challenge in a CD8 T-cell dependent manner) and are also effective in various CD40-negative tumors. These mAb are able to clear bulk tumors from mice with near terminal disease. To date, several CD40 mAb have been investigated in clinical trials: CP-870,893 (Pfizer and VLST), dacetuzumab (Seattle Genetics), Chi Lob 7/4 (University of Southampton), and lucatumumab (Novartis). They have been used for treating melanoma, pancreatic carcinoma, mesothelioma, hematological malignancies, especially Non-Hodgkin's lymphoma, lymphoma, chronic lymphocytic leukemia, and advanced solid tumors.

These therapeutic antibodies show diverse activities ranging from strong agonism (CP-870,893) to antagonism (lucatumumab). Currently there is no satisfactory explanation for this heterogeneity. The primary mechanistic rationale invoked for agonistic CD40 mAb is to activate host APC in order to induce clinically meaningful anti-tumor T-cell responses in patients. These include T cell-independent but macrophage-dependent triggering of tumor regression. CD40-activated macrophages can become tumoricidal, and least in pancreatic cancer, may also facilitate the depletion of tumor stroma which induces tumor collapse in vivo. Importantly, these mechanisms do not require expression of CD40 by the tumor, which has justified inclusion of patients with a broad range of tumors in many of the clinical trials. Insofar as these strategies aim to activate DC, macrophages, or both, the goal is not necessarily for the CD40 mAb to kill the cell it binds to, for example, via complement mediated cytotoxicity (CMC) or antibody dependent cellular cytoxicity (ADCC). Thus, by design, the strong agonistic antibody does not mediate CMC or ADCC.

In contrast, other human CD40 mAb can mediate CMC and ADCC against CD40+ tumors, such as nearly all B cell malignancies, a fraction of melanomas, and certain carcinomas. Finally, there is some evidence that ligation of CD40 on tumor cells promotes apoptosis and that this can be accomplished without engaging any immune effector pathway. This has been shown for CD40+ B cell malignancies and certain solid tumors such as CD40+ carcinomas and melanomas.

A detailed description of CD40 and its function can be found, e.g., in Vonderheide et al., "Agonistic CD40 antibodies and cancer therapy." (2013): 1035-1043; Beatty, et al. "CD40 agonists alter tumor stroma and show efficacy against pancreatic carcinoma in mice and humans." Science 331.6024 (2011): 1612-1616; Vonderheide, et al. "Clinical activity and immune modulation in cancer patients treated with CP-870,893, a novel CD40 agonist monoclonal antibody." Journal of Clinical Oncology 25.7 (2007): 876-883; each of which is incorporated by reference in its entirety.

Figure 3:
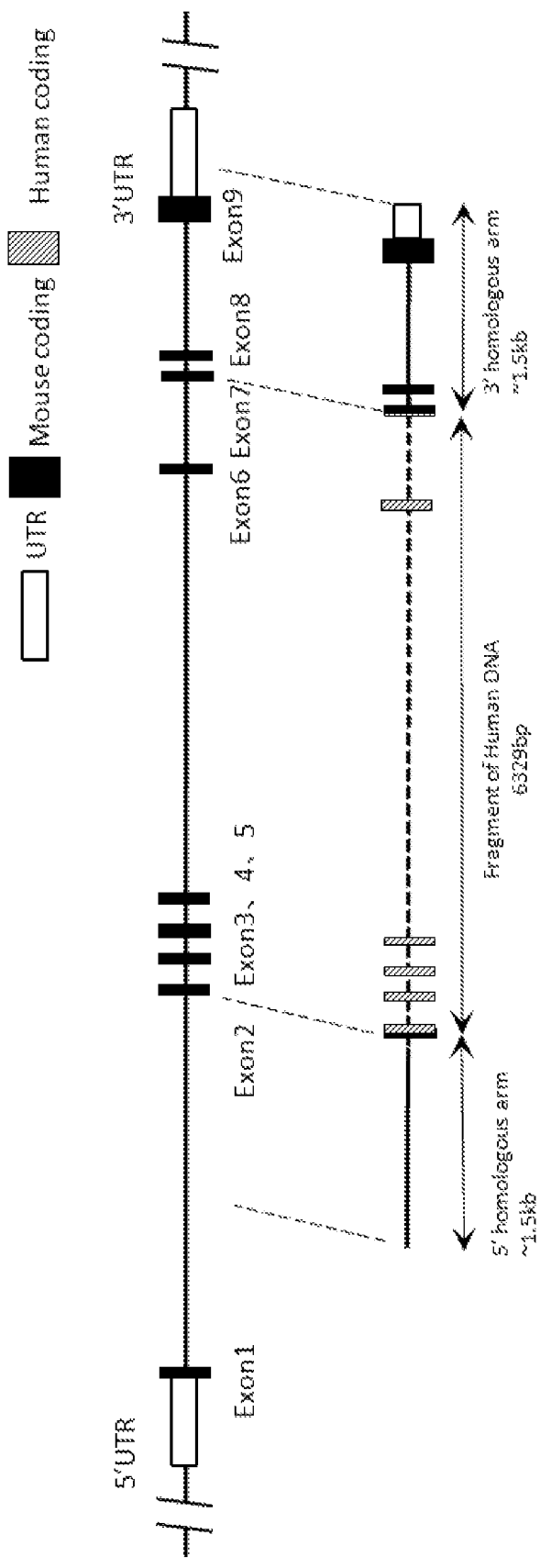
FIG. 3 is a schematic diagram showing a gene targeting strategy.

In human genomes, CD40 gene (Gene ID: 958) locus has nine exons, exon 1, exon 2, exon 3, exon 4, exon 5, exon 6, exon 7, exon 8, and exon 9 (FIG. 3). The CD40 protein also has an extracellular region, a transmembrane region, and a cytoplasmic region, and the signal peptide is located at the extracellular region of CD40. The nucleotide sequence for human CD40 mRNA is NM_001250.5 (SEQ ID NO: 22), and the amino acid sequence for human CD40 is NP_001241.1 (SEQ ID NO: 23). The location for each exon and each region in human CD40 nucleotide sequence and amino acid sequence is listed below:

TABLE 1

| Human CD40 (approximate location) | NM_001250.5 1629 bp (SEQ ID NO: 22) | NP_001241.1 277 aa (SEQ ID NO: 23) |
| --- | --- | --- |
| Exon 1 | 1-141 | 1-17 |
| Exon 2 | 142-220 | 18-43 |

TABLE 1-continued

| Human CD40 (approximate location) | NM_001250.5 1629 bp (SEQ ID NO: 22) | NP_001241.1 277 aa (SEQ ID NO: 23) |
| --- | --- | --- |
| Exon 3 | 221-346 | 44-85 |
| Exon 4 | 347-493 | 86-134 |
| Exon 5 | 494-587 | 135-166 |
| Exon 6 | 588-649 | 167-186 |
| Exon 7 | 650-736 | 187-215 |
| Exon 8 | 737-765 | 216-225 |
| Exon 9 | 766-1629 | 226-277 |
| Signal peptide | 91-150 | 1-20 |
| Extracellular region (excluding signal peptide region) | 151-669 | 21-193 |
| Transmembrane region | 670-735 | 194-215 |
| Cytoplasmic region | 736-921 | 216-277 |
| Donor region in Example | 148-666 | 20-192 |

In mice, CD40 gene locus has nine exons, exon 1, exon 2, exon 3, exon 4, exon 5, exon 6, exon 7, exon 8, and exon 9 (FIG. 3). The mouse CD40 protein also has an extracellular region, a transmembrane region, and a cytoplasmic region, and the signal peptide is located at the extracellular region of CD40. The nucleotide sequence for mouse CD40 cDNA is NM_011611.2 (SEQ ID NO: 20), the amino acid sequence for mouse CD40 is NP_035741.2 (SEQ ID NO: 21). The location for each exon and each region in the mouse CD40 nucleotide sequence and amino acid sequence is listed below:

TABLE 2

| Mouse CD40 (approximate location) | NM_011611.2 1683 bp (SEQ ID NO: 20) | NP_035741.2 289 aa (SEQ ID NO: 21) |
| --- | --- | --- |
| Exon 1 | 1-123 | 1-17 |
| Exon 2 | 124-202 | 18-43 |
| Exon 3 | 203-328 | 44-85 |
| Exon 4 | 329-475 | 86-134 |
| Exon 5 | 476-569 | 135-166 |
| Exon 6 | 570-631 | 167-186 |
| Exon 7 | 632-718 | 187-215 |
| Exon 8 | 719-750 | 216-226 |
| Exon 9 | 751-1683 | 227-289 |
| Signal peptide | 73-129 | 1-19 |
| Extracellular region (excluding signal peptide region) | 130-651 | 20-193 |
| Transmembrane region | 652-717 | 194-215 |
| Cytoplasmic region | 718-939 | 216-289 |
| Replaced region in Example | 130-648 | 20-192 |

The mouse CD40 gene (Gene ID: 21939) is located in in Chromosome 2 of the mouse genome, which is located from 165055608-165071654 of NC_000068.7 (GRCm38.p4 (GCF_000001635.24)). The 5'-UTR is from 165055636 to 165055707, exon 1 is from 165055636 to 165055758, the first intron is from 165055759 to 165062285, exon 2 is from 165062286 to 165062364, the second intron is from 165062365 to 165062660, exon 3 is from 165062661 to 165062786, the third intron is from 165062787 to 165063021, exon 4 is from 165063022 to 165063168, the fourth intron is from 165063169 to 165063467, exon 5 is from 165063468 to 165063561, the fifth intron is from 165063562 to Ser. No. 16/506,502, exon 6 is from 165066503 to 165066564, the sixth intron is from 165066565 to 165069628, exon 7 is from 165069629 to 165069715, the seventh intron is from 165069716 to 165069816, exon 8 is from 165069,817 to 165069848, the eighth intron is from 165069849 to 165070721, exon 9 is from 165070722 to 165072948, the 3'-UTR is from 165070914 to 165072948, based on transcript NM_011611.2. All relevant information for mouse CD40 locus can be found in the NCBI website with Gene ID: 21939, which is incorporated by reference herein in its entirety.

FIG. 20 shows the alignment between mouse CD40 amino acid sequence (NP_035741.2; SEQ ID NO: 21) and human CD40 amino acid sequence (NP_001241.1; SEQ ID NO: 23). Thus, the corresponding amino acid residue or region between human and mouse CD40 can be found in FIG. 20.

CD40 genes, proteins, and locus of the other species are also known in the art. For example, the gene ID for CD40 in *Rattus norvegicus* is 171369, the gene ID for CD40 in *Macaca mulatta* (Rhesus monkey) is 707749, the gene ID for CD40 in *Canis lupus familiaris* (dog) is 403469, and the gene ID for CD40 in *Cavia porcellus* (domestic guinea pig) is 100728791. The relevant information for these genes (e.g., intron sequences, exon sequences, amino acid residues of these proteins) can be found, e.g., in NCBI database, which is incorporated by reference herein in its entirety.

The present disclosure provides human or chimeric (e.g., humanized) CD40 nucleotide sequence and/or amino acid sequences. In some embodiments, the entire sequence of mouse exon 1, exon 2, exon 3, exon 4, exon 5, exon 6, exon 7, exon 8, exon 9, signal peptide, extracellular region, transmembrane region, and/or cytoplasmic region are replaced by the corresponding human sequence. In some embodiments, a "region" or "portion" of mouse exon 1, exon 2, exon 3, exon 4, exon 5, exon 6, exon 7, exon 8, exon 9, signal peptide, extracellular region, transmembrane region, and/or cytoplasmic region are replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 250, 300, 350, 400, 500, or 600 nucleotides, or at least 1, 2, 3, 4, 5, 6, 7, 8, 9, 10, 20, 30, 40, 50, 60, 70, 80, 90, 100, 110, 120, 130, 140, 150, 160, 170, 180, 190, or 200 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, exon 6, exon 7, exon 8, exon 9, signal peptide, extracellular region, transmembrane region, or cytoplasmic region. In some embodiments, a region, a portion, or the entire sequence of mouse exon 1, exon 2, exon 3, exon 4, exon 5, exon 6, exon 7, exon 8, and/or exon 9 (e.g., exon 2, exon 3, exon 4, exon 5, exon 6, exon 7) are replaced by the human exon 1, exon 2, exon 3, exon 4, exon 5, exon 6, exon 7, exon 8, and/or exon 9 (e.g., exon 2, exon 3, exon 4, exon 5, exon 6, exon 7) sequence.

In some embodiments, the present disclosure also provides a chimeric (e.g., humanized) CD40 nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse CD40 mRNA sequence (e.g., SEQ ID NO: 20), mouse CD40 amino acid sequence (e.g., SEQ ID NO: 21), or a portion thereof (e.g., exon 2, exon 3, exon 4, exon 5, exon 6, and exon 7); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human CD40 mRNA sequence (e.g., SEQ ID NO: 22), human CD40 amino acid sequence (e.g., SEQ ID NO: 23), or a portion thereof (e.g., exon 2, exon 3, exon 4, exon 5, exon 6, and exon 7).

In some embodiments, the sequence encoding amino acids 20-192 of mouse CD40 (SEQ ID NO: 21) is replaced. In some embodiments, the sequence is replaced by a sequence encoding a corresponding region of human CD40 (e.g., amino acids 20-192 of human CD40 (SEQ ID NO: 23)).

In some embodiments, the nucleic acids as described herein are operably linked to a promotor or regulatory element, e.g., an endogenous mouse CD40 promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse CD40 nucleotide sequence (e.g., exon 2, exon 3, exon 4, exon 5, exon 6, exon 7, or NM_011611.2 (SEQ ID NO: 20)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse CD40 nucleotide sequence (e.g., exon 2, exon 3, exon 4, exon 5, exon 6, exon 7, or NM_011611.2 (SEQ ID NO: 20)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human CD40 nucleotide sequence (e.g., exon 2, exon 3, exon 4, exon 5, exon 6, exon 7, or NM_001250.5 (SEQ ID NO: 22)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human CD40 nucleotide sequence (e.g., exon 2, exon 3, exon 4, exon 5, exon 6, exon 7, or NM_001250.5 (SEQ ID NO: 22)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse CD40 amino acid sequence (e.g., exon 2, exon 3, exon 4, exon 5, exon 6, exon 7, or NP_035741.2 (SEQ ID NO: 21)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse CD40 amino acid sequence (e.g., exon 2, exon 3, exon 4, exon 5, exon 6, exon 7, or NP_035741.2 (SEQ ID NO: 21)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human CD40 amino acid sequence (e.g., exon 2, exon 3, exon 4, exon 5, exon 6, exon 7, or NP_001241.1 (SEQ ID NO: 23)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human CD40 amino acid sequence (e.g., exon 2, exon 3, exon 4, exon 5, exon 6, exon 7, or NP_001241.1 (SEQ ID NO: 23)).

The present disclosure also provides a humanized CD40 mouse amino acid sequence, wherein the amino acid sequence is selected from the group consisting of:

a) an amino acid sequence shown in SEQ ID NO: 27;

b) an amino acid sequence having a homology of at least 90% with or at least 90% identical to the amino acid sequence shown in SEQ ID NO: 27;

c) an amino acid sequence encoded by a nucleic acid sequence, wherein the nucleic acid sequence is able to hybridize to a nucleotide sequence encoding the amino acid shown in SEQ ID NO: 27 under a low stringency condition or a strict stringency condition;

d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 27;

e) an amino acid sequence that is different from the amino acid sequence shown in SEQ ID NO: 27 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 27.

The present disclosure also relates to a CD40 nucleic acid (e.g., DNA or RNA) sequence, wherein the nucleic acid sequence can be selected from the group consisting of:

a) a nucleic acid sequence as shown in SEQ ID NO: 25, or a nucleic acid sequence encoding a homologous CD40 amino acid sequence of a humanized mouse;

b) a nucleic acid sequence that is shown in SEQ ID NO: 26;

c) a nucleic acid sequence that is able to hybridize to the nucleotide sequence as shown in SEQ ID NO: 25 or SEQ ID NO: 26 under a low stringency condition or a strict stringency condition;

d) a nucleic acid sequence that has a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the nucleotide sequence as shown in SEQ ID NO: 25 or SEQ ID NO: 26;

e) a nucleic acid sequence that encodes an amino acid sequence, wherein the amino acid sequence has a homology of at least 90% with or at least 90% identical to the amino acid sequence shown in SEQ ID NO: 27;

f) a nucleic acid sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 27;

g) a nucleic acid sequence that encodes an amino acid sequence, wherein the amino acid sequence is different from the amino acid sequence shown in SEQ ID NO: 27 by no more than 10, 9, 8, 7, 6, 5, 4, 3, 2 or no more than 1 amino acid; and/or h) a nucleic acid sequence that encodes an amino acid sequence, wherein the amino acid sequence comprises a substitution, a deletion and/or insertion of one or more amino acids to the amino acid sequence shown in SEQ ID NO: 27.

The present disclosure further relates to a CD40 genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 25 or SEQ ID NO: 26.

The disclosure also provides an amino acid sequence that has a homology of at least 90% with, or at least 90% identical to the sequence shown in SEQ ID NO: 27, and has protein activity. In some embodiments, the homology with the sequence shown in SEQ ID NO: 27 is at least about 90%, 91%, 92%, 93%, 94%, 95%, 96%, 97%, 98%, or at least 99%. In some embodiments, the foregoing homology is at least about 60%, 61%, 62%, 63%, 64%, 65%, 66%, 67%, 68%, 69%, 70%, 71%, 72%, 73%, 74%, 75%, 80%, or 85%.

In some embodiments, the percentage identity with the sequence shown in SEQ ID NO: 27 is at least about 90%, 91%, 92%, 93%, 94%, 95%, 96%, 97%, 98%, or at least 99%. In some embodiments, the foregoing percentage identity is at least about 60%, 61%, 62%, 63%, 64%, 65%, 66%, 67%, 68%, 69%, 70%, 71%, 72%, 73%, 74%, 75%, 80%, or 85%.

The disclosure also provides a nucleotide sequence that has a homology of at least 90%, or at least 90% identical to the sequence shown in SEQ ID NO: 25 or SEQ ID NO: 26, and encodes a polypeptide that has protein activity. In some embodiments, the homology with the sequence shown in SEQ ID NO: 25 or SEQ ID NO: 26 is at least about 90%, 91%, 92%, 93%, 94%, 95%, 96%, 97%, 98%, or at least 99%. In some embodiments, the foregoing homology is at least about 50%, 55%, 60%, 65%, 66%, 67%, 68%, 69%, 70%, 71%, 72%, 73%, 74%, 75%, 80%, or 85%.

In some embodiments, the percentage identity with the sequence shown in SEQ ID NO: 25 or SEQ ID NO: 26 is at least about 90%, 91%, 92%, 93%, 94%, 95%, 96%, 97%, 98%, or at least 99%. In some embodiments, the foregoing percentage identity is at least about 50%, 55%, 60%, 65%, 66%, 67%, 68%, 69%, 70%, 71%, 72%, 73%, 74%, 75%, 80%, or 85%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, or 200 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The percentage of residues conserved with similar physicochemical properties (percent homology), e.g. leucine and isoleucine, can also be used to measure sequence similarity. Families of amino acid residues having similar physicochemical properties have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The homology percentage, in many cases, is higher than the identity percentage.

Cells, tissues, and animals (e.g., mouse) are also provided that comprise the nucleotide sequences as described herein, as well as cells, tissues, and animals (e.g., mouse) that express human or chimeric (e.g., humanized) CD40 from an endogenous non-human CD40 locus.

Genetically Modified Animals

As used herein, the term "genetically-modified non-human animal" refers to a non-human animal having exogenous DNA in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the exogenous DNA in its genome. The cell having exogenous DNA can be various kinds of cells, e.g., an endogenous cell, a somatic cell, an immune cell, a T cell, a B cell, an antigen presenting cell, a macrophage, a dendritic cell, a germ cell, a blastocyst, or an endogenous tumor cell. In some embodiments, genetically-modified non-human animals are provided that comprise a modified endogenous CD40 locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wildtype nucleic acid in the animal. In some embodiments, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wildtype amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized CD40 gene or a humanized CD40 nucleic acid. In some embodiments, at least one or more portions of the gene or the nucleic acid is from the human CD40 gene, at least one or more portions of the gene or the nucleic acid is from a non-human CD40 gene. In some embodiments, the gene or the nucleic acid comprises a sequence that encodes a CD40 protein. The encoded CD40 protein is functional or has at least one activity of the human CD40 protein or the non-human CD40 protein, e.g., binding with human or non-human CD40L (CD154), increasing the level of activation of macrophages, activating B cell (e.g., inducing B cell division, antibody isotype switching, differentiation to plasma cells, production of antibodies), inducing expression of costimulatory and MHC molecules on dendritic cells, increasing production of proinflammatory cytokines, increasing antigen-presenting function, inducing activation and proliferation of immune cells (e.g., B cells, macrophages, dendritic cells), increasing the production of cytokines, and/or upregulating the immune response.

In some embodiments, the chimeric protein or the chimeric polypeptide is a humanized CD40 protein or a humanized CD40 polypeptide. In some embodiments, at least one or more portions of the amino acid sequence of the protein or the polypeptide is from a human CD40 protein, and at least one or more portions of the amino acid sequence of the protein or the polypeptide is from a non-human CD40 protein. The humanized CD40 protein or the humanized CD40 polypeptide is functional or has at least one activity of the human CD40 protein or the non-human CD40 protein.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable embryonic stem (ES) cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, *Malagasy* rats and mice), Platacanthomyidae (e.g., spiny dormice), and Spalacidae (e.g., mole rats, bamboo rats, and zokors). In some embodiments, the genetically modified rodent is selected from a true mouse or rat (family Muridae), a gerbil, a spiny mouse, and a crested rat. In some embodiments, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/01a. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10: 836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiments, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized CD40 animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NOD/SCID mice, IL2Rγ knockout mice, NOD/SCID/γcnull mice (Ito, M. et al., NOD/SCID/γcnull mouse: an excellent recipient mouse model for engraftment of human cells, Blood 100(9): 3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human CD40 locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/γc null mice, nude mice, Rag1 and/or Rag2 knockout mice, and a combination thereof. These genetically modified animals are described, e.g., in US20150106961, which is incorporated herein by reference in its entirety. In some embodiments, the mouse can include a replacement of all or part of mature CD40 coding sequence with human mature CD40 coding sequence.

Genetically modified non-human animals that comprise a modification of an endogenous non-human CD40 locus. In some embodiments, the modification can comprise a human nucleic acid sequence encoding at least a portion of a mature CD40 protein (e.g., at least 10%, 20%, 30%, 40%, 50%, 60%, 70%, 80%, 90%, 95%, 96%, 97%, 98%, or 99% identical to the mature CD40 protein sequence). Although genetically modified cells are also provided that can comprise the modifications described herein (e.g., ES cells, somatic cells), in many embodiments, the genetically modified non-human animals comprise the modification of the endogenous CD40 locus in the germline of the animal.

Genetically modified animals can express a human CD40 and/or a chimeric (e.g., humanized) CD40 from endogenous mouse loci, wherein the endogenous mouse CD40 gene has been replaced with a human CD40 gene and/or a nucleotide sequence that encodes a region of human CD40 sequence or an amino acid sequence that is at least 10%, 20%, 30%, 40%, 50%, 60%, 70&, 80%, 90%, 95%, 96%, 97%, 98%, or 99% identical to the human CD40 sequence. In various embodiments, an endogenous non-human CD40 locus is modified in whole or in part to comprise human nucleic acid sequence encoding at least one protein-coding sequence of a mature CD40 protein.

In some embodiments, the genetically modified mice express the human CD40 and/or chimeric CD40 (e.g., humanized CD40) from endogenous loci that are under control of mouse promoters and/or mouse regulatory elements. The replacement(s) at the endogenous mouse loci provide non-human animals that express human CD40 or chimeric CD40 (e.g., humanized CD40) in appropriate cell types and in a manner that does not result in the potential pathologies observed in some other transgenic mice known in the art. The human CD40 or the chimeric CD40 (e.g., humanized CD40) expressed in animal can maintain one or more functions of the wildtype mouse or human CD40 in the animal. For example, human or non-human CD40 ligands (e.g., CD154) can bind to the expressed CD40, upregulate immune response, e.g., upregulate immune response by at least 10%, 20%, 30%, 40%, or 50%. Furthermore, in some embodiments, the animal does not express endogenous CD40. As used herein, the term "endogenous CD40" refers to CD40 protein that is expressed from an endogenous CD40 nucleotide sequence of the non-human animal (e.g., mouse) before any genetic modification.

The genome of the animal can comprise a sequence encoding an amino acid sequence that is at least 70%, 75%, 80%, 85%, 90%, 95%, 99%, or 100% identical to human CD40 (NP_001241.1) (SEQ ID NO: 23). In some embodiments, the genome comprises a sequence encoding an amino acid sequence that is at least 70%, 75%, 80%, 85%, 90%, 95%, 99%, or 100% identical to SEQ ID NO: 27.

The genome of the genetically modified animal can comprise a replacement at an endogenous CD40 gene locus of a sequence encoding a region of endogenous CD40 with a sequence encoding a corresponding region of human CD40. In some embodiments, the sequence that is replaced is any sequence within the endogenous CD40 gene locus, e.g., exon 1, exon 2, exon 3, exon 4, exon 5, exon 6, exon 7, exon 8, exon 9, 5'-UTR, 3'-UTR, the first intron, the second intron, and the third intron, the fourth intron, the fifth intron, the sixth intron, the seventh intron, the eighth intron etc. In some embodiments, the sequence that is replaced is within the regulatory region of the endogenous CD40 gene. In some embodiments, the sequence that is replaced is exon 2, exon 3, exon 4, exon 5, exon 6, exon 7 or part thereof, of an endogenous mouse CD40 gene locus.

The genetically modified animal can have one or more cells expressing a human or chimeric CD40 (e.g., humanized CD40) having an extracellular region and a cytoplasmic region, wherein the extracellular region comprises a sequence that is at least 50%, 60%, 70%, 80%, 90%, 95%, 99% identical to the extracellular region of human CD40. In some embodiments, the extracellular region of the humanized CD40 has a sequence that has at least 10, 20, 30, 40, 50, 60, 70, 80, 90, 100, 110, 120, 130, 140, 150, 160, 170, or 180 amino acids (e.g., contiguously or non-contiguously) that are identical to human CD40. Because human CD40 and non-human CD40 (e.g., mouse CD40) sequences, in many cases, are different, antibodies that bind to human CD40 will not necessarily have the same binding affinity with non-human CD40 or have the same effects to non-human CD40. Therefore, the genetically modified animal having a human or a humanized extracellular region can be used to better evaluate the effects of anti-human CD40 antibodies in an animal model. In some embodiments, the genome of the genetically modified animal comprises a sequence encoding an amino acid sequence that corresponds to part or the entire sequence of exon 2, exon 3, exon 4, exon 5, exon 6, and/or exon 7 of human CD40, part or the entire sequence of extracellular region of human CD40 (with or without signal peptide), or part or the entire sequence of amino acids 20-192 of SEQ ID NO: 23.

In some embodiments, the non-human animal can have, at an endogenous CD40 gene locus, a nucleotide sequence encoding a chimeric human/non-human CD40 polypeptide, wherein a human portion of the chimeric human/non-human CD40 polypeptide comprises a portion of human CD40 extracellular domain, and wherein the animal expresses a functional CD40 on a surface of a cell of the animal. The human portion of the chimeric human/non-human CD40 polypeptide can comprise a portion of exon 2, exon 3, exon 4, exon 5, exon 6, and/or exon 7 of human CD40. In some embodiments, the human portion of the chimeric human/non-human CD40 polypeptide can comprise a sequence that is at least 80%, 85%, 90%, 95%, or 99% identical to amino acids 20-192 of SEQ ID NO: 23.

In some embodiments, the non-human portion of the chimeric human/non-human CD40 polypeptide comprises transmembrane and/or cytoplasmic regions of an endogenous non-human CD40 polypeptide. There may be several advantages that are associated with the transmembrane and/or cytoplasmic regions of an endogenous non-human CD40 polypeptide. For example, once a CD40 ligand (e.g., CD154) or an anti-CD40 antibody binds to CD40, they can properly transmit extracellular signals into the cells and initiate the downstream pathway. A human or humanized transmembrane and/or cytoplasmic regions may not function properly in non-human animal cells. In some embodiments, a few extracellular amino acids that are close to the transmembrane region of CD40 are also derived from endogenous sequence. These amino acids can also be important for transmembrane signal transmission.

Furthermore, the genetically modified animal can be heterozygous with respect to the replacement at the endogenous CD40 locus, or homozygous with respect to the replacement at the endogenous CD40 locus.

In some embodiments, the humanized CD40 locus lacks a human CD40 5'-UTR. In some embodiment, the humanized CD40 locus comprises a rodent (e.g., mouse) 5'-UTR. In some embodiments, the humanization comprises a human 3'-UTR. In appropriate cases, it may be reasonable to presume that the mouse and human CD40 genes appear to be similarly regulated based on the similarity of their 5'-flanking sequence. As shown in the present disclosure, humanized CD40 mice that comprise a replacement at an endogenous mouse CD40 locus, which retain mouse regulatory elements but comprise a humanization of CD40 encoding sequence, do not exhibit pathologies. Both genetically modified mice that are heterozygous or homozygous for humanized CD40 are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized CD40 gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human or humanized CD40 in the genome of the animal.

Figure 2:
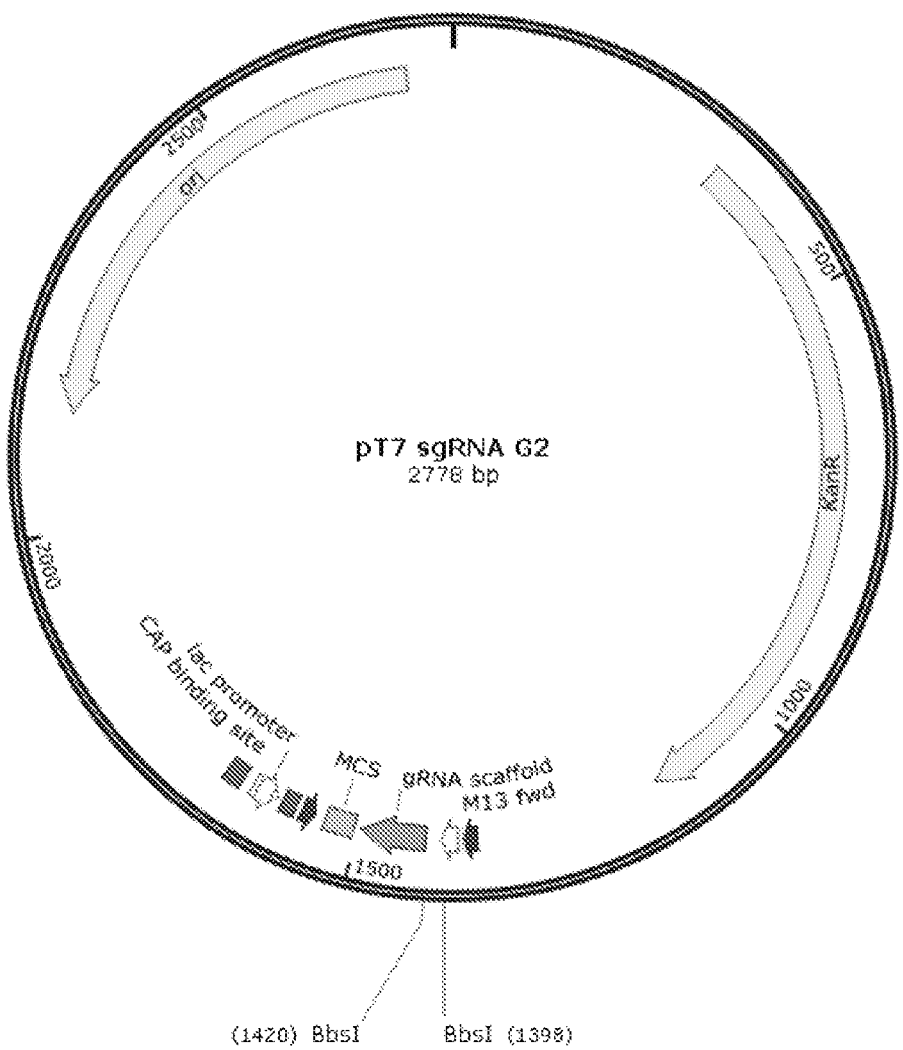
FIG. 2 is a schematic diagram showing the structure of pT7-sgRNA-G2 plasmid.

In some embodiments, the non-human mammal comprises the genetic construct as described herein (e.g., gene construct as shown in FIG. 2 or FIG. 3). In some embodiments, a non-human mammal expressing human or humanized CD40 is provided. In some embodiments, the tissue-specific expression of human or humanized CD40 protein is provided.

In some embodiments, the expression of human or humanized CD40 in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human CD40 protein can be detected by a variety of methods.

There are many analytical methods that can be used to detect exogenous DNA, including methods at the level of nucleic acid (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human or humanized CD40 protein.

Vectors

The present disclosure relates to a targeting vector, comprising: a) a DNA fragment homologous to the 5' end of a region to be altered (5' arm), which is selected from the CD40 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the CD40 gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000068.7; c) the DNA fragment homologous to the 3' end of the region to be altered (3' arm) is selected from the nucleotide sequences that have at least 90% homology to the NCBI accession number NC_000068.7.

In some embodiments, a) the DNA fragment homologous to the 5' end of a region to be altered (5' arm) is selected from the nucleotides from the position 165060750 to the position 165062291 of the NCBI accession number NC_000068.7; c) the DNA fragment homologous to the 3' end of the region to be altered (3' arm) is selected from the nucleotides from the position 165069646 to the position 165071120 of the NCBI accession number NC_000068.7.

In some embodiments, the length of the selected genomic nucleotide sequence in the targeting vector can be more than about 3 kb, about 3.5 kb, about 4 kb, about 4.5 kb, about 5 kb, about 5.5 kb, or about 6 kb.

In some embodiments, the region to be altered is exon 1, exon 2, exon 3, exon 4, exon 5, exon 6, exon 7, exon8, and/or exon 9 of CD40 gene (e.g., exon 2, exon 3, exon 4, exon 5, exon 6, and/or exon 7 of mouse CD40 gene).

The targeting vector can further include a selected gene marker.

In some embodiments, the sequence of the 5' arm is shown in SEQ ID NO: 28; and the sequence of the 3' arm is shown in SEQ ID NO: 29.

In some embodiments, the sequence is derived from human (e.g., 46121826-46128154 of NC_000020.11). For example, the target region in the targeting vector is a part or entirety of the nucleotide sequence of a human CD40, preferably exon 2, exon 3, exon 4, exon 5, exon 6, and/or exon 7 of the human CD40. In some embodiments, the nucleotide sequence of the humanized CD40 encodes the entire or the part of human CD40 protein with the NCBI accession number NP_001241.1 (SEQ ID NO: 23).

The disclosure also relates to a cell comprising the targeting vectors as described above.

In addition, the present disclosure further relates to a non-human mammalian cell, having any one of the foregoing targeting vectors, and one or more in vitro transcripts of the construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., "Delivery technologies for genome editing," Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous CD40 gene locus, a sequence encoding a region of an endogenous CD40 with a sequence encoding a corresponding region of human or chimeric CD40. In some embodiments, the replacement occurs in a germ cell, a somatic cell, a blastocyst, or a fibroblast, etc. The nucleus of a somatic cell or the fibroblast can be inserted into an enucleated oocyte.

FIG. 3 shows a humanization strategy for a mouse CD40 locus. In FIG. 3, the targeting strategy involves a vector comprising the 5' end homologous arm, human CD40 gene fragment, 3' homologous arm. The process can involve replacing endogenous CD40 sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous CD40 sequence with human CD40 sequence.

Thus, in some embodiments, the methods for making a genetically modified, humanized animal, can include the step of replacing at an endogenous CD40 locus (or site), a nucleic acid encoding a sequence encoding a region of endogenous CD40 with a sequence encoding a corresponding region of human CD40. The sequence can include a region (e.g., a part or the entire region) of exon 1, exon 2, exon 3, exon 4, exon 5, exon 6, exon 7, exon 8, and/or exon 9 of a human CD40 gene. In some embodiments, the sequence includes a region of exon 2, exon 3, exon 4, exon 5, exon 6, and exon 7 of a human CD40 gene (e.g., amino acids 20-192 of SEQ ID NO: 23). In some embodiments, the region is located within the extracellular region of CD40. In some embodiments, the endogenous CD40 locus is exon 2, exon 3, exon 4, exon 5, exon 6, and/or exon 7 of mouse CD40.

In some embodiments, the methods of modifying a CD40 locus of a mouse to express a chimeric human/mouse CD40 peptide can include the steps of replacing at the endogenous mouse CD40 locus a nucleotide sequence encoding a mouse CD40 with a nucleotide sequence encoding a human CD40, thereby generating a sequence encoding a chimeric human/mouse CD40.

In some embodiments, the nucleotide sequence encoding the chimeric human/mouse CD40 can include a first nucleotide sequence encoding an extracellular region of mouse CD40 (with or without the mouse or human signal peptide sequence); a second nucleotide sequence encoding an extracellular region of human CD40; a third nucleotide sequence encoding a transmembrane and a cytoplasmic region of a mouse CD40.

In some embodiments, the nucleotide sequences as described herein do not overlap with each other (e.g., the first nucleotide sequence, the second nucleotide sequence, and/or the third nucleotide sequence do not overlap). In some embodiments, the amino acid sequences as described herein do not overlap with each other.

The present disclosure further provides a method for establishing a CD40 gene humanized animal model, involving the following steps:

(a) providing the cell (e.g. a fertilized egg cell) based on the methods described herein;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the non-human mammal in the foregoing method is a mouse (e.g., a C57BL/6 mouse).

In some embodiments, the non-human mammal in step (c) is a female with pseudo pregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the methods described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate in the context of the humanized animal's physiology.

Genetically modified animals that express human or humanized CD40 protein, e.g., in a physiologically appropriate manner, provide a variety of uses that include, but are not limited to, developing therapeutics for human diseases and disorders, and assessing the toxicity and/or the efficacy of these human therapeutics in the animal models.

In various aspects, genetically modified animals are provided that express human or humanized CD40, which are useful for testing agents that can decrease or block the interaction between CD40 and CD40 ligands (e.g., CD154) or the interaction between CD40 and anti-human CD40 antibodies, testing whether an agent can increase or decrease the immune response, and/or determining whether an agent is an CD40 agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of an anti-CD40 antibody for the treatment of cancer. The methods involve administering the anti-CD40 antibody (e.g., anti-human CD40 antibody) to the animal as described herein, wherein the animal has a tumor; and determining the inhibitory effects of the anti-CD40 antibody to the tumor. The inhibitory effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, MRI or CT.

In some embodiments, the tumor comprises one or more cancer cells (e.g., human or mouse cancer cells) that are injected into the animal. In some embodiments, the anti-CD40 antibody or anti-CD154 antibody prevents CD154 from binding to CD40. In some embodiments, the anti-CD40 antibody or anti-CD154 antibody does not prevent CD154 from binding to CD40.

In some embodiments, the genetically modified animals can be used for determining whether an anti-CD40 antibody is a CD40 agonist or antagonist. In some embodiments, the methods as described herein are also designed to determine the effects of the agent (e.g., anti-CD40 antibodies) on CD40, e.g., whether the agent can stimulate immune cells or inhibit immune cells (e.g., macrophages, B cells, or DC), whether the agent can increase or decrease the production of cytokines, whether the agent can activate or deactivate immune cells (e.g., macrophages, B cells, or DC), whether the agent can upregulate the immune response or downregulate immune response, and/or whether the agent can induce complement mediated cytotoxicity (CMC) or antibody dependent cellular cytotoxicity (ADCC). In some embodiments, the genetically modified animals can be used for determining the effective dosage of a therapeutic agent for treating a disease in the subject, e.g., cancer, or autoimmune diseases.

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the anti-CD40 antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the anti-CD40 antibody is designed for treating melanoma (e.g., advanced melanoma), non-small cell lung carcinoma (NSCLC), small cell lung cancer (SCLC), B-cell non-Hodgkin lymphoma, bladder cancer, and/or prostate cancer (e.g., metastatic hormone-refractory prostate cancer). In some embodiments, the anti-CD40 antibody is designed for treating hepatocellular, ovarian, colon, or cervical carcinomas. In some embodiments, the anti-CD40 antibody is designed for treating advanced breast cancer, advanced ovarian cancer, and/or advanced refractory solid tumor. In some embodiments, the anti-CD40 antibody is designed for treating metastatic solid tumors, NSCLC, melanoma, non-Hodgkin lymphoma, colorectal cancer, and multiple myeloma. In some embodiments, the anti-CD40 antibody is designed for treating melanoma, pancreatic carcinoma, mesothelioma, hematological malignancies (e.g., Non-Hodgkin's lymphoma, lymphoma, chronic lymphocytic leukemia), or solid tumors (e.g., advanced solid tumors). In some embodiments, the anti-CD40 antibody is designed for treating carcinomas (e.g., nasopharynx carcinoma, bladder carcinoma, cervix carcinoma, kidney carcinoma or ovary carcinoma).

In some embodiments, the anti-CD40 antibody is designed for treating various autoimmune diseases. Thus, the methods as described herein can be used to determine the effectiveness of an anti-CD40 antibody in inhibiting immune response.

The present disclosure also provides methods of determining toxicity of an antibody (e.g., anti-CD40 antibody). The methods involve administering the antibody to the animal as described herein. The animal is then evaluated for its weight change, red blood cell count, hematocrit, and/or hemoglobin. In some embodiments, the antibody can decrease the red blood cells (RBC), hematocrit, or hemoglobin by more than 20%, 30%, 40%, or 50%. In some embodiments, the animals can have a weight that is at least 5%, 10%, 20%, 30%, or 40% smaller than the weight of the control group (e.g., average weight of the animals that are not treated with the antibody).

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the methods as described herein in the screening, verifying, evaluating or studying the CD40 gene function, human CD40 antibodies, drugs for human CD40 targeting sites, the drugs or efficacies for human CD40 targeting sites, the drugs for immune-related diseases and antitumor drugs.

Genetically Modified Animal Model with Two or More Human or Chimeric Genes

The present disclosure further relates to methods for generating genetically modified animal model with two or more human or chimeric genes. The animal can comprise a human or chimeric CD40 gene and a sequence encoding an additional human or chimeric protein.

In some embodiments, the additional human or chimeric protein can be programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD47, CD137, CD154, T-Cell Immunoreceptor With Ig And ITIM Domains (TIGIT), T-cell
Immunoglobulin and Mucin-Domain Containing-3 (TIM-3), Glucocorticoid-Induced TNFR-Related Protein (GITR), Signal regulatory protein α (SIRPα) or TNF Receptor Superfamily Member 4 (TNFRSF4 or OX40).

The methods of generating genetically modified animal model with two or more human or chimeric genes (e.g., humanized genes) can include the following steps:

(a) using the methods of introducing human CD40 gene or chimeric CD40 gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric PD-1, CTLA-4, LAG-3, BTLA, PD-L1, CD27, CD28, CD47, CD137, CD154, TIGIT, TIM-3, GITR, SIRPα, or OX40. Some of these genetically modified non-human animal are described, e.g., in PCT/CN2017/090320, PCT/CN2017/099577, PCT/CN2017/099575, PCT/CN2017/099576, PCT/CN2017/099574, PCT/CN2017/106024, PCT/CN2017/110494, PCT/CN2017/110435, PCT/CN2017/120388, PCT/CN2018/081628, PCT/CN2018/081629; each of which is incorporated herein by reference in its entirety.

In some embodiments, the CD40 humanization is directly performed on a genetically modified animal having a human or chimeric PD-1, CTLA-4, BTLA, PD-L1, CD27, CD28, CD47, CD137, CD154, TIGIT, TIM-3, GITR, SIRPα, or OX40 gene.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-CD40 antibody and an additional therapeutic agent for the treatment of cancer. The methods include administering the anti-CD40 antibody and the additional therapeutic agent to the animal, wherein the animal has a tumor; and determining the inhibitory effects of the combined treatment to the tumor. In some embodiments, the additional therapeutic agent is an antibody that specifically binds to PD-1, CTLA-4, BTLA, PD-L1, CD27, CD28, CD47, CD137, CD154, TIGIT, TIM-3, GITR, SIRPa, or OX40. In some embodiments, the additional therapeutic agent is an anti-CTLA4 antibody (e.g., ipilimumab), an anti-PD-1 antibody (e.g., nivolumab), or an anti-PD-L1 antibody.

In some embodiments, the animal further comprises a sequence encoding a human or humanized PD-1, a sequence encoding a human or humanized PD-L1, or a sequence encoding a human or humanized CTLA-4. In some embodiments, the additional therapeutic agent is an anti-PD-1 antibody (e.g., nivolumab, pembrolizumab), an anti-PD-L1 antibody, or an anti-CTLA-4 antibody. In some embodiments, the tumor comprises one or more tumor cells that express CD80, CD86, PD-L1, and/or PD-L2.

In some embodiments, the combination treatment is designed for treating various cancer as described herein, e.g., melanoma, non-small cell lung carcinoma (NSCLC), small cell lung cancer (SCLC), bladder cancer, prostate cancer (e.g., metastatic hormone-refractory prostate cancer), advanced breast cancer, advanced ovarian cancer, and/or advanced refractory solid tumor. In some embodiments, the combination treatment is designed for treating metastatic solid tumors, NSCLC, melanoma, B-cell non-Hodgkin lymphoma, colorectal cancer, and multiple myeloma. In some embodiments, the combination treatment is designed for treating melanoma, carcinomas (e.g., pancreatic carcinoma), mesothelioma, hematological malignancies (e.g., Non-Hodgkin's lymphoma, lymphoma, chronic lymphocytic leukemia), or solid tumors (e.g., advanced solid tumors).

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.
Materials and Methods
The following materials were used in the following examples.

C57BL/6 mice were purchased from the China Food and Drugs Research Institute National Rodent Experimental Animal Center.

EcoRI, BamHI, HpaI, SalI, XhoI, KpnI, SpeI, BstBI, ApaI, StuI restriction enzymes were purchased from NEB (Catalog numbers: R3101M, R3136M, R0105S, R3138M, R0146S, R0142S, R3133M, R0159S, R0114S, R0187M).

Ambion in vitro transcription kit was purchased from Ambion (Catalog number: AM1354).

UCA kit was obtained from Beijing Biocytogen Co., Ltd. (Catalog number: BCG-DX-001).

TOP10 competent cells were purchased from the Tiangen Biotech (Beijing) Co. (Catalog number: CB104-02).

Cas9 mRNA was purchased from SIGMA (Catalog number: CAS9MRNA-1EA).

AIO kit was obtained from Beijing Biocytogen Co., Ltd. (Catalog number: BCG-DX-004).

The pHSG299 was purchased from Takara (Catalog number: 3299).

BAC clone library was purchased from Invitrogen (Catalog number: RPCI23.C and RPCI11.C).

Purified NA/LE Hamster Anti-Mouse CD3e (mCD3) antibody was purchased from BD (Catalog number: 553057).

PE anti-mouse CD40 antibody (mCD40PE) was purchased from Biolegend (Catalog number: 124610).

FITC anti-mouse CD19 antibody (mCD19 FITC) was purchased from Biolegend (Catalog number: 115506).

APC anti-human CD40 antibody (hCD40APC) was purchased from Biolegend (Catalog number: 313008).

PerCP/Cy5.5 anti-mouse TCR β chain (mTcR β PerCP) was purchased from Biolegend (Catalog number: 109228).

PE anti-mouse CD279 (PD-1) antibody (mPD-1 PE) was purchased from Biolegend (Catalog number: 109104).

FITC anti-human CD279 (PD-1) antibody (hPD-1 FITC) was purchased from Biolegend (Catalog number: 329904).

Example 1: Design of sgRNA for CD40 Gene

The 5'-terminal targeting sites (sgRNA1 to sgRNA7) and the 3'-terminal targeting sites (sgRNA8 to sgRNA14) were designed and synthesized.

The 5'-terminal targeting sites were located in exon 2 of mouse CD40 gene. The 3'-terminal targeting sites were located in exon 7 of mouse CD40 gene. The targeting site sequences on CD40 for each sgRNA are shown below:

```
sgRNA-1 target sequence (SEQ ID NO: 1):
5'-gacaaacagtacctccacgatgg-3' sgRNA-2 target sequence (SEQ ID NO: 2):
5'-cgggacagcttggggtattctgg-3' sgRNA-3 target sequence (SEQ ID NO: 3):
5'-acgtaacacactgccctagatgg-3' sgRNA-4 target sequence (SEQ ID NO: 4):
5'-gggtcttggtacggggcaggagg-3' sgRNA-5 target sequence (SEQ ID NO: 5):
5'-gcatccaccagcaatccaagagg-3' sgRNA-6 target sequence (SEQ ID NO: 6):
5'-tctcagaccctacacgagtaagg-3' sgRNA-7 target sequence (SEQ ID NO: 7):
5'-acagactgtgtcacaacccaggg-3' sgRNA-8 target sequence (SEQ ID NO: 8):
5'-cgcatccgggactttaaacctgg-3' sgRNA-9 target sequence (SEQ ID NO: 9):
5'-tgaccagcagggctcgcatccgg-3' sgRNA-10 target sequence (SEQ ID NO: 10):
5'-ccaatggagtgtgctcccactgg-3' sgRNA-11 target sequence (SEQ ID NO: 11):
5'-actgcttaaaagctctgacctgg-3' sgRNA-12 target sequence (SEQ ID NO: 12):
5'-tgtgggtaatgtggtcactaggg-3' sgRNA-13 target sequence (SEQ ID NO: 13):
5'-tggagtgtgctcccactggcagg-3' sgRNA-14 target sequence (SEQ ID NO: 14):
5'-cattgggagcaccgccagtggg-3'
```

Example 2: Testing sgRNA Activity

Figure 1B:
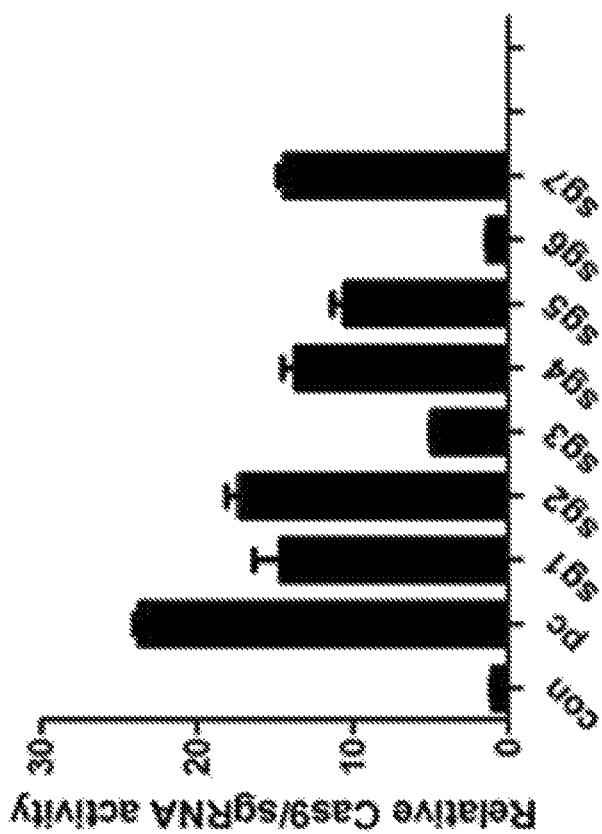
FIG. 1B is a graph showing activity testing results for sgRNA8-sgRNA14 (Con is a negative control; PC is a positive control).

The UCA kit was used to detect the activities of sgRNAs (FIGS. 1A-1B and Table 4). The results show that the guide sgRNAs had different activities. Two of them sgRNA1 (SEQ ID NO: 1) and sgRNA8 (SEQ ID NO: 8) were selected for further experiments.

The synthesized sgRNA sequences based on sgRNA1 and sgRNA8 target sequences are listed in the following table:

TABLE 3 sgRNA1 and sgRNA8 sequences sgRNA1 sequences

SEQ ID NO: 15   Upstream:
                5'-acaaacagtacctccacga-3'
SEQ ID NO: 16   Downstream:
                5'-tcgtggaggtactgtttgt-3' sgRNA8 sequences

SEQ ID NO: 17   Upstream:
                5'-catccgggactttaaacc-3'
SEQ ID NO: 18   Downstream:
                5'-ggtttaaagtcccggatg-3'

TABLE 4

Activities of sgRNAs

| 5'-terminal targeting sites | | 3'-terminal targeting sites | |
| --- | --- | --- | --- |
| sgRNAs | Normalized Activities | sgRNAs | Normalized Activities |
| Negative control (con) | 1.00 | Negative control (con) | 1.00 |
| Positive control (pc) | 23.66 | Positive control (pc) | 41.79 |
| sgRNA-1 | 14.61 | sgRNA-8 | 39.58 |
| sgRNA-2 | 17.26 | sgRNA-9 | 21.17 |
| sgRNA-3 | 4.89 | sgRNA-10 | 7.75 |
| sgRNA-4 | 13.69 | sgRNA-11 | 7.65 |
| sgRNA-5 | 10.52 | sgRNA-12 | 3.87 |
| sgRNA-6 | 1.30 | sgRNA-13 | 5.29 |
| sgRNA-7 | 14.36 | sgRNA-14 | 18.83 |

Example 3: Constructing pT7-sgRNA G2 Plasmids

A map of pT7-sgRNA G2 vector is shown in FIG. 2. The plasmid backbone was obtained from Takara (Catalog No. 3299).

The DNA fragment containing T7 promoter and sgRNA scaffold was synthesized, and linked to the backbone vector by restriction enzyme digestion (EcoRI and BamHI) and ligation. The target plasmid was confirmed by the sequencing results.

The DNA fragment containing the T7 promoter and sgRNA scaffold (SEQ ID NO: 19) is shown below:

```
GAATTCTAATACGACTCACTATAGGGGGTCTTCGAGAAGACCTGTTTTAG
AGCTAGAAATAGCAAGTTAAAATAAGGCTAGTCCGTTATCAACTTGAAAA
AGTGGCACCGAGTCGGTGCTTTTAAAGGATCC
```

Example 4: Constructing Recombinant Expression Vectors pT7-CD40-1 and pT7-CD40-8

TAGG was added to the 5' end of SEQ ID NO: 15 and SEQ ID NO: 17 to obtain a forward oligonucleotide sequence, and AAAC was added to the 5' end of the complementary strand (SEQ ID NO: 16 and SEQ ID NO: 18) to obtain a reverse oligonucleotide sequence.

```
sgRNA-1 forward oligonucleotide:
                                (SEQ ID NO: 59)
5'-TAGGACAAACAGTACCTCCACGA-3' sgRNA-1 reverse oligonucleotide:
                                (SEQ ID NO: 60)
5'-AAACTCGTGGAGGTACTGTTTGT-3' sgRNA8 forward oligonucleotide:
                                (SEQ ID NO: 61)
5'-TAGGCATCCGGGACTTTAAACC-3' sgRNA8 reverse oligonucleotide:
                                (SEQ ID NO: 57)
5'-AAACGGTTTAAAGTCCCGGATG-3'
```

After annealing, they were respectively ligated to pT7-sgRNA plasmid (linearized with BbsI) to obtain the expression vectors pT7-CD40-1 and pT7-CD40-8. The ligation reaction was set up as follows:

TABLE 5

| The ligation reaction mix (10 μL) | |
|---|---|
| sgRNA after annealing | 1 μL (0.5 μM) |
| pT7-sgRNA G2 vector | 1 μL (10 ng) |
| T4 DNA Ligase | 1 μL (5U) |
| 10× T4 DNA Ligase buffer | 1 μL |
| 50% PEG4000 | 1 μL |
| H₂O | Add to 10 μL |

The ligation reaction was carried out at room temperature for 10 to 30 minutes. The ligation product was then transferred to 30 μL of TOP10 competent cells. The cells were then plated on a petri dish with Kanamycin, and then cultured at 37° C. for at least 12 hours and then two clones were selected and added to LB medium with Kanamycin (5 ml), and then cultured at 37° C. at 250 rpm for at least 12 hours.

Clones were randomly selected and sequenced to verify their sequences. The vectors with correct sequences were selected for subsequent experiments.

Example 5: Sequence Design for Humanized CD40

Figure 4:
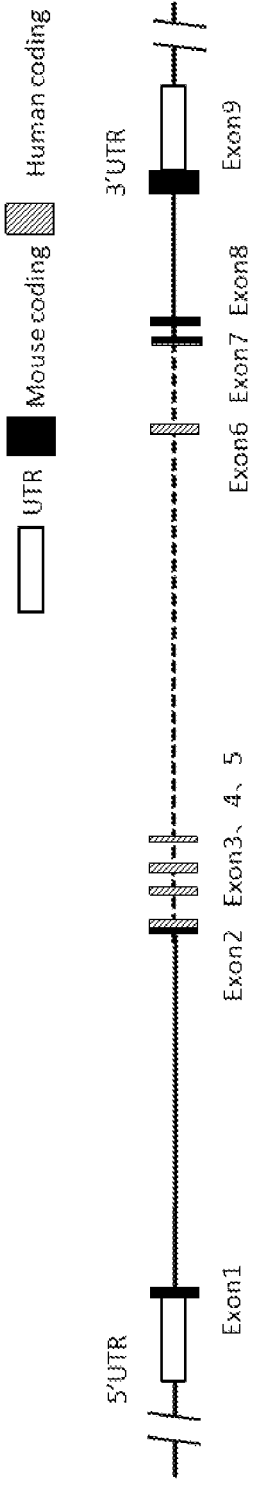
FIG. 4 is a schematic diagram showing a map of an example of humanized CD40 gene in mouse.

A partial coding sequence of the mouse CD40 gene (Gene ID: 21939) from exons 2-7 (based on the transcript of NCBI accession number NM_011611.2→NP_035741.2 whose mRNA sequence is shown in SEQ ID NO: 20, and the corresponding protein sequence is shown in SEQ ID NO: 21) was replaced with a corresponding coding sequence of human homologous CD40 gene (Gene ID: 958) (based on the transcript of NCBI accession number NM_001250.5→NP_001241.1, whose mRNA sequence was shown in SEQ ID NO: 22, and the corresponding protein sequence is shown in SEQ ID NO: 23). The comparison between the mouse CD40 and human CD40 is shown in FIG. 20, and the finally obtained humanized CD40 gene is shown in FIG. 4. The humanized mouse CD40 gene DNA sequence (chimeric CD40 gene DNA) is shown in SEQ ID NO: 24.

```
gagcactgaagagtcctgtgcatctgttcggattagagggttctgcgttcttgctttggtagatggcagtaagacgatgtga caacagagtaaaaaaaaaatagacctcacactctgggggctcacttttctgctttggatttccacatcagctacagcctgc gtcttggctaactttcaacatgccggtggaagatcccttccagctgtccacttctgttttaggtccatccagaaccaccca ctgcatgcagagaaaaacagtacctaataaacagtcagtgctgttctttgtgccagccaggtgagatgccaaccctctagcc ccatcatggagtccccctttgctttggtggcagacgcagaccccatatgttaactgtaaactcaaatctgaaacgacccatt tcccagccctgcttcactgtcagaatgttctggttccctctctaccaggtaaaactctgtctaccctgaactagggatccca gcttctccatcttcctcgcctgattatgaaggatccaagacttttcatcttttgaatcccctaccctaaagcctggcctgatca ttgtgtggttagtgtctgactcatggagttggccagagccctccctcatttcctgatgttttccaggacagaaactggtgag tgactgcacagagttcactgaaacggaatgccttccttgcggtgaaagcgaattcctagacacctggaacagagagacacac tgccaccagcacaaatactgcgacccagtgcgtgcgctgttgggaagggacgcttgggaaccgggctgatattcccgaca atgcagccattctaattttatgtagccagggtctgctctgattggttggagtccgggctgtactgatcattaaatgatttga ttgccatctctacttggaagagggtctgaggaagaaagagcaggcaatgtgggagtgaggctcagagcatggcccagcagg gggttccatccttcctgcccttctcttctcagacctagggcttcgggtccagcagaagggcacctcagaaacagacaccat ctgcacctgtgaagaaggctggcactgtacgagtgaggcctgtgagagctgtgtcctgcaccgctcatgctcgcccggcttt ggggtcaagcagattggtaagtggctcatctgggaatcagttttggaggggacagaggagcttagggcccaaggtgagggg ctgggcagtgggcacttagcccagaggcagaggaagcagaggctccaacctatgtcggtatcccactggagtgagctgca gacgggaccttgttcattctgccttctgccatggggatctgcctttgaagggcaatgggagaagtcctcctggggactgcag ctgtcgggggcagtaccacatcgggggaagagtgctcaaggcaggagctcttcccgtcctgcctggccactggctgccttgt gagccggacaggtggtccactgtgatggttaatgtccccctcccacccactcccagctacaggggtttctgataccatctg cgagccctgcccagtcggcttcttctccaatgtgtcatctgctttcgaaaaatgtcacccttggacaaggtataagcactca tcccttgtgtttcctgctctaagagtggcatggagctgcctccattctctccagccacctgtcctgtccctgctcccagagg tccacacacactcatgtacttgtgaagcatctgcagagtggcctcatggccaaccagacaggcacatttccacattttttt
```

-continued

```
gcctgctgtctctttgaggtaatagacactgttgatctctcgcttcatgagagcctcctatcttgggggtattgggacactt attttagctttccttctgcccctcctgcttctcctcagttccaacatgagcgttcgacagtttctttcaaatcatgacactc tcctatttgagatgcttcctgtctctctgttggaactaagactccttagcatggcacccaaccttcctgttgcatttcctgc tctctttcctgcatcgcatagcttcatgctacttgcaatcctctgaacacactgttcattctcttccatcaaactcatctgc ctggaatccttaaacatgggccccaggccaggcgcggtggctcttgcctgtaatctcagcactttggatgccaaggcgggt ggatcacttgaggtcaggagttcaagaccagccagcacaacatggtaaaaacccatctctactaaaaataccaaaaaatta gctgggtgtggtggtgggcgcctgtaatcccagctcctcgggaggctgaggcaggagaatcacttgaacccggaaggtggag tttgcagtgagccaagatagcgccactgcactccagcctgggcaacagagcgacattctgtctcaaaaaacaaacacctgcc ccattaacttttttgcatttgattttaaaaatgggcaagataggcacatgggacagaaggcacaaaagagccaaagtgatgt cttctcccatccctgcccctaggctcccagttctttctggagggagccattgttccttgcatatccttccagagattcta catataaacaaaccaacacacacacacacacacaaacacacacaaaatttccctccttttacttttgcacaaataggagt atacattttatttgttaactgtctgcctttccctaatagattgaaaattccttaaatgtagaaacttggcctttttttttc ttccattgatacatcccctatacctggaacagtacctgacgcatggtaggtgcttaaattttactgataaatgttgactga taatctggaggcaccactggtatagtttttttttttttttttttttttttttttgagacagagtctcactctgtcgcc caggctggagtgcagtggcgcaatctcggctcactgcaagctctgcctcccaggttcacgccattctcctgcctcagcctcc tgagtagctgggactataggcgcccgccaccacacccggctaatttttttgtattttagtagagacggcgtttcaccgtgt tagccaggatggtcttgatctcctgacctcgtgatccgtctgccttggcctcccaaagtgctgggattacaggcgtgagcca ccgtgcccggccaccagtggtatagtattaatggaatcagtgcattggcttacgtatctgattacagctcagtaagtgtgtg accctcactgagcctcagtctcctcatctgaaaaatgggaatgaccttcatttcacaaggcttgagctaaaaacatgtaaag tgtattgtaaattcctgaatgctctactcatgtaagactaaagtaggccgggcgtggtggctcacacctgtaattgcagcac tttgggaggccgaggagggcagatcatgaggtcaagagatcgagaccatcctggctaatatggtaaaaccctgtctctacta aaaatacaaaaattagctgggcgtggtggcgcacatctgtagtcccagctactcaggaggcggaggcaggagaattgcttga acctgggaggtggaggttgcagtgagctgagatcgcgccactgcattccagccagtctggcgaaagagcaagactctgtctc aaaaaaaaaaaaaaaaaaaaaaaaactaaagtacatggtttcttcaaagcttctctctttctcccaccttagatgattttc ctttgcaatgtcctgtgtccattccgcccactcctcctggggccacctggaccaggtcttcatcatctcatatctatatgt ttgctgtgtctcctggctggccactcttctgtaatttctcctcctctgagctctctgggcagctgaatcttctcactagtga agtcgcctggttggatgctgatgagactgaccagctgaatccagttgaaaacttcacacttggcagtgatctggttctaaag acacaattttccatagtttcctaacaccatcctgcatgccacctgccttatttcccacatcacatcgtcccacttagcggg actgcactgctgatccaaattttacatcctttaggggccactcaggtcatatgtcctcagggaagtcttctggaagaacct taaaccagaggttctcaacagggggcagttttgctccctgtggaacgtttgccaatgtctggacacatttcattcgtcacac aaacggagaggggatgctacagggatctggcggatagaggccagggatgctgctgaacatctgcaatgcataggacagccc accccaccccacaccccagtaaataatgatccagcccaagtgtcactggtgctgacgttgagtaaccctatcttaagct gaactcatcatctctccattccagcccttggtggattctgtctcctctgaaccattcccatctcactttagcctacctagatc acaaagcttggcactcattatagactcccctatttattactccttcaagatgtgcaagaatcttttctctgcactttaagt tctgtaagaagagtctgtgtcgttcctataataaccagcataggacgttgcacgtgttgtgtgctcagtgaacctggatttg ttgattgttgactgactcactctagagttggaaatcttatgcttggggaaacttaatatctctttctttctctgtgtgtgtg catttgtgcacgtgtctgtgcatagctgtgagaccaaagacctggttgtgcaacaggcaggcacaaacaagactgatgttgt ctgtggtgagtcctggacaatgggccctggagaaaagcctaggaaggtgggaactgaaggggagatgaggcacacaggaaca ctggatgggaaaaggggaggggaggcagtttgggggtgtggtatcacagctctgccacttatcttgggagtctgggcaaat cacttcccctctcttagcctcagtttcttcatctgtaaaatgggatgataacagcacttccttagtaggttttgatttaga
```

-continued

*gtgagaaggttggcctacagtaaagatcagataatgtaaatcagtgaaaaaggtcaggggtaagaaaattacattctcttta*

*cctaacgctaaatgaccagttaatgggtgcagcacaccaacatggtacatgtatacatatgtaacaaacctgcacattatgc*

*acatgtaccctaaagcttaaagtataataataataaaatttaaaaaaacgaaaaatacattctctttgcttttctcaaaat*

*gtactttcctctttgtagggctgggactagaatgaggtgagcaaggcacttgccctcgggcgcaatatttaagaaggtgcca*

*taaaagtgtagtaatcaaggtaaattcattttgatgcaatattttaaaaataaaaattaatgcaaagaaatccatgatgag*

*caagatagcaacattttaaataaagaacaggatccgaccctgtgtttgcatgaccctgcctcactcacctcaccctaatcct*

*ggccctggttccagtaaaaggaataggcagccagcctgcaggccgtagtttgctgacttggtgtccgcctgatgattttcaa*

*aatatggcattaaaagaatgtttaccttgatgactgagtgttttggacatccttttcaatttttgtcctgaaacaatttcatc*

*ccttgcctcacgctagtctccgccctgccttttggtctttcttttattttcccactttgaaaaaaaaattcggcatgagaaa*

*tactttacctttcccctccactcttctataccaaaagcaacatgcagacatgaatcatgctagacctcggcattgggcagag*

*agcagggagtggcggggagcatggtgagcaggtggtgacagccactgccaccactcgcttctagatggttcccaggtgggga*

*ggctgccaactggaacccagtcttcccagtttgtaagagaaatcagatgtctaggtttgaatatgtgatctcccagtttaaa*

*aatgtcggcaaatatttccaaacgttaagaaaatgttctggctccttttaaagacatctgccagccacatttccccaaggacc*

*gcggtttgaaccttctgatgtagatgagctctgacattggaagattctggagtctgacaagtcacagcaggttgagggtagg*

*gagaaactgcaggtgaggggtgcatgctgaagtcctgatttctccaggtccccaggatcggctgc*gagccctgctggtcatt cctgtcgtgatgggcatcctcatcaccatttcggggtgtttctctatatcagtgagtgctcaggagaggaaagggagggag ggttcagccctgtcgaaccagcctcctgactcaccctcgcaatgtcccacaccccttcttcttctcactagaaaaggtggtc aagaaaccaaaggataatgaggtaagccatccctgagggagagatgctggaaagagtgactggtgggcagggagggaggctc acggcgtagggagacagactcagtaagcagagagctt SEQ ID NO: 24 shows only the modified portion of DNA sequence, wherein the italicized underlined region is from human CD40.

The coding region sequence, mRNA sequence and the encoded protein sequence thereof of the modified humanized CD40 are respectively shown in SEQ ID NO: 25, SEQ ID NO: 26, and SEQ ID NO: 27.

To the extent that either human CD40 or mouse CD40 has more than one isoforms or transcripts, the methods as described herein can be applied to other isoforms or transcripts.

Example 6: pClon-2G-CD40 Plasmids

Based on the sequences, a targeting strategy for generating the humanized CD40 mouse model is shown in FIG. 3.

The 5' homologous arm comprises nucleic acid 165060750-165062291 of NCBI Accession No. NC_000068.7 (SEQ ID NO: 28). The 3' homologous arm comprises nucleic acid 165069646-165071120 of NCBI Accession No. NC_000068.7 (SEQ ID NO: 29). The human sequence corresponds to 46121826-46128154 of NCBI Accession No. NC_000020.11 (SEQ ID NO: 30).

Primers for amplifying the 5 recombination fragments (LR, A1, A2, A3, RR) and related sequences were designed. Among them, the LR fragment corresponds to the 5' homologous arm, the RR fragment corresponds to the 3' homologous arm, the A1+A2+A3 fragments correspond to the human CD40 sequence.

The primers are shown in the table below.

TABLE 6

Primers for recombination fragments

| Fragment | Length (bp) | | Primer sequence |
|---|---|---|---|
| LR | 1575 bp | F: | 5'-ctagctcgagctgctggacaaacctcagagagtggctgc-3' (SEQ ID NO: 31) |
| | | R: | 5'-ctgcatgcagtgggtggttctggatggacctaaaaacagaagtggacagc-3' (SEQ ID NO: 32) |
| A1 | 1425 bp | F: | 5'-gctgtccacttctgtttttaggtccatccagaaccacccactgcatgcagag-3' (SEQ ID NO: 33) |
| | | R: | 5'-ctagggtaccatcgactagtatctttcgaaagcagatgacacattgg-3' (SEQ ID NO: 34) |
| A2 | 2627 bp | F: | 5'-ccaatgtgtcatctgctttcgaaaaatg-3' (SEQ ID NO: 35) |
| | | R: | 5'-ggcgacttcactagtgagaagattcag-3' (SEQ ID NO: 36) |

TABLE 6-continued

Primers for recombination fragments

| Fragment | Length (bp) | | Primer sequence |
|---|---|---|---|
| A3 | 2401 bp | F: | ctgaatcttctcactagtgaatcgcc-3'<br>(SEQ ID NO: 37) |
| | | R: | 5'-acaggaatgaccagcagggctcgcagccgatcctggggacctggag-3'<br>(SEQ ID NO: 38) |
| RR | 1507 bp | F: | 5'-tccaggtcccaggatcggctgcgagccctgctggtcattcctgtc-3'<br>(SEQ ID NO: 39) |
| | | R: | 5'-ctagggtaccttggtaggtatcactgtggaccccc-3'<br>(SEQ ID NO: 40) |

KOD-plus DNA polymerase was used to amplify the recombination fragments from Bacterial Artificial Chromosome (BAC) clones. Among them, BAC clones with mouse CD40 (Catalog number: RP23-89H6) were used as a template for LR and RR recombination fragments, and BAC clones with human CD40 (Catalog number: RP11-177B15) were used as a template for A1, A2, and A3 recombination fragments. The conditions for the PCR amplification were shown in the tables below.

TABLE 7

The PCR reaction system (20 µL)

| Composition | Amount |
|---|---|
| 10× buffer for KOD-plus DNA polymerase | 2 µl |
| dNTP (2 mM) | 2 µL |
| MgSO$_4$ (25 mM) | 0.8 µL |
| Upstream primer F (10 µM) | 0.6 µL |
| Downstream primer R (10 µM) | 0.6 µL |
| BAC DNA templates | 50 ng |
| KOD-Plus DNA polymerase (1 U/µL) | 0.6 µL |
| H$_2$O | Add to 20 µL |

TABLE 8

The PCR reaction conditions

| Temperature | Time | Cycles |
|---|---|---|
| 94° C. | 5 min | 1 |
| 94° C. | 30 sec | 15 |
| 67° C. (−0.7° C./cycle) | 30 sec | |
| 68° C. | 1 kb/min | |
| 94° C. | 30 sec | 25 |
| 57° C. | 30 sec | |
| 68° C. | 1 kb/min | |
| 68° C. | 10 min | 1 |
| 4° C. | 10 min | 1 |

The PCR products (DNA fragments) LR, A1, A2, A3, and RR were collected and were used to construct targeting vectors. The targeting vectors were obtained by the following steps:

(1). Fragments LR and A1 were ligated by overlap PCR (Phusion DNA Polymerases). Fragment A3 and RR were also ligated by overlap PCR. The conditions for ligation were shown in the tables below. The sequences of LR-A1 and A3-RR were verified by sequencing.

(2). Fragments were ligated to the pClon-2G plasmid in the AIO kit by restriction enzymes in the following order: LR-A1 (XhoI+KpnI), A3-RR (SpeI+KpnI), A2 (BstBI+SpeI) to obtain pClon-2G-CD40 vector.

TABLE 9

The PCR reaction system (20 µL)

| Composition | Amount |
|---|---|
| 5× Phusion HF Buffer | 4 µL |
| dNTP (10 mM) | 0.4 µL |
| Primer F (10 µM) | 1 µL |
| Primer R (10 µM) | 1 µL |
| DNA template | 5 ng |
| Phusion DNA polymerase (2 U/µL) | 0.2 µL |
| H$_2$O | Add to 20 µL |

TABLE 10

The PCR reaction conditions

| Temperature | Time | Cycles |
|---|---|---|
| 98° C. | 30 sec | 1 |
| 98° C. | 10 sec | 35 |
| 58° C. | 25 sec | |
| 72° C. | 30 sec/kb | |
| 72° C. | 5-10 min | 1 |
| 4° C. | 10 min | 1 |

When fragments LR and A1 were ligated, Primer F in Table 9 was SEQ ID NO: 31, Primer R was SEQ ID NO: 34, and the DNA template was the recovered PCR amplification product of the LR fragment and A1 fragment. When fragments A3 and RR were ligated, Primer F was SEQ ID NO: 37, primer R was SEQ ID NO: 40, and the DNA template was the recovered PCR amplification product of the A3 fragment and RR fragment.

Example 7. Verification of pClon-2G-CD40 Vectors

Figure 5:
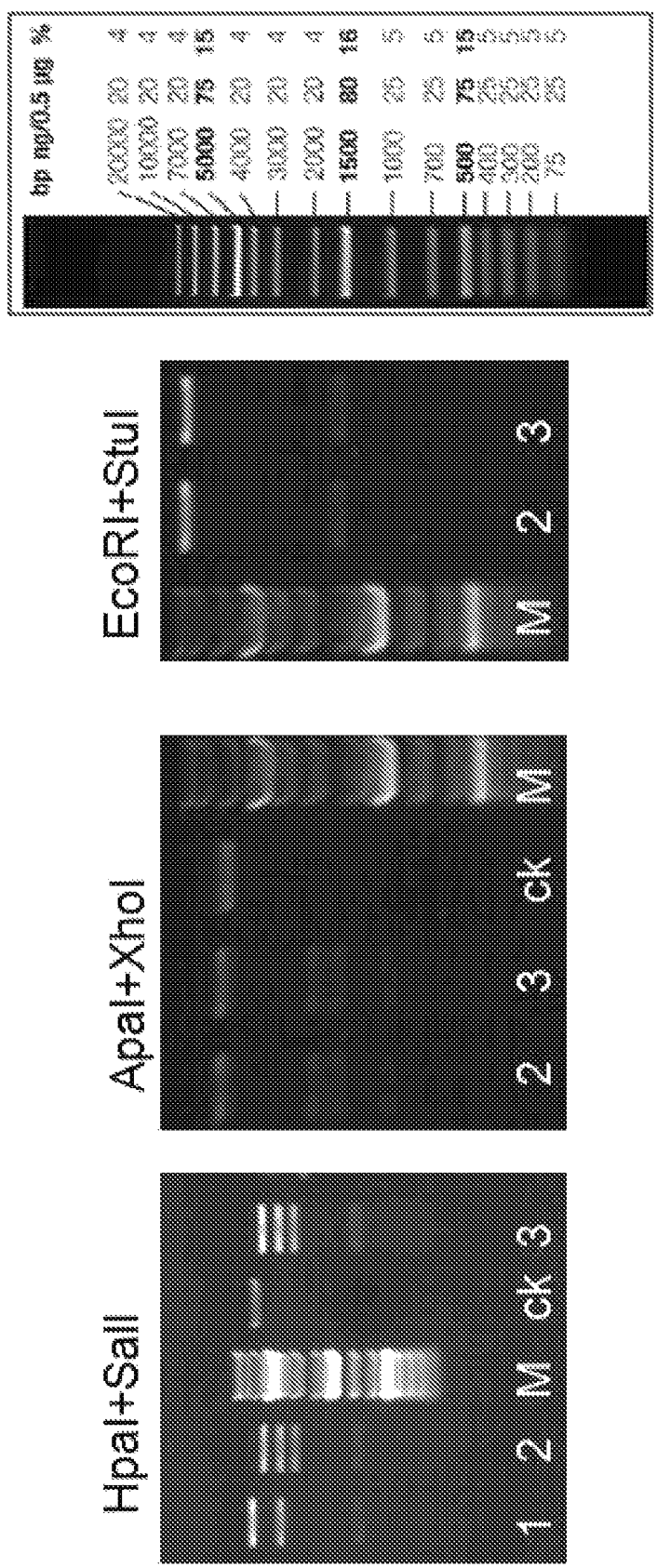
FIG. 5 shows the restriction enzymes digestion results of the targeting plasmid pClon-2G-CD40 by three sets of restriction enzymes.

Two pClon-2G-CD40 clones were randomly selected and tested by three sets of restriction enzymes. Among them, HpaI+SalI should generate 839 bp+2608 bp+3578 bp+5072 bp fragments; ApaI+XhoI should generate 1203 bp+1985 bp+2532 bp+6377 bp fragments; EcoRI+StuI should generate 201 bp+398 bp+1825 bp+9673 bp fragments. Plasmids 2 and 3 had the expected results (FIG. 5). The sequences of Plasmid 3 were further confirmed by sequencing.

Example 8: Microinjection and Embryo Transfer Using C57BL/6 Mice

The pre-mixed Cas9 mRNA, pClon-2G-CD40 plasmid and in vitro transcription products of pT7-CD40-1, pT7-CD40-8 plasmids were injected into the cytoplasm or nucleus of mouse fertilized eggs (C57BL/6 background)

with a microinjection instrument (using Ambion in vitro transcription kit to carry out the transcription according to the method provided in the product instruction). The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice (F0 generation). The mouse population was further expanded by cross-mating and self-mating to establish stable mouse lines. These humanized mice were named as B-hCD40.

Example 9: Verification of Genetic Modification

1. Genotype Determination for F0 Generation Mice

PCR analysis was performed using mouse tail genomic DNA of F0 generation mice. Primer L-GT-F is located on the left side of 5' homologous arm, Primer R-GT-R is located on the right side of 3' homologous arm, and both R-GT-F and L-GT-R are located within the fifth intron.

```
5' end primers:
Upstream: L-GT-F
                              (SEQ ID NO: 41)
5'-GAAGTGTTACAGCTCCGCTCTGAGG-3';

Downstream: L-GT-R
                              (SEQ ID NO: 42)
5'-AGCTCAAGCCTTGTGAAATGAAGGT-3'

3' end primers:
Upstream: R-GT-F
                              (SEQ ID NO: 43)
5'-AATGGAATCAGTGCATTGGCTTACG-3';

Downstream: R-GT-R
                              (SEQ ID NO: 44)
5'-TTTGGGCAGCAAGCTCCTTTACTCA-3'
```

Figure 6A:
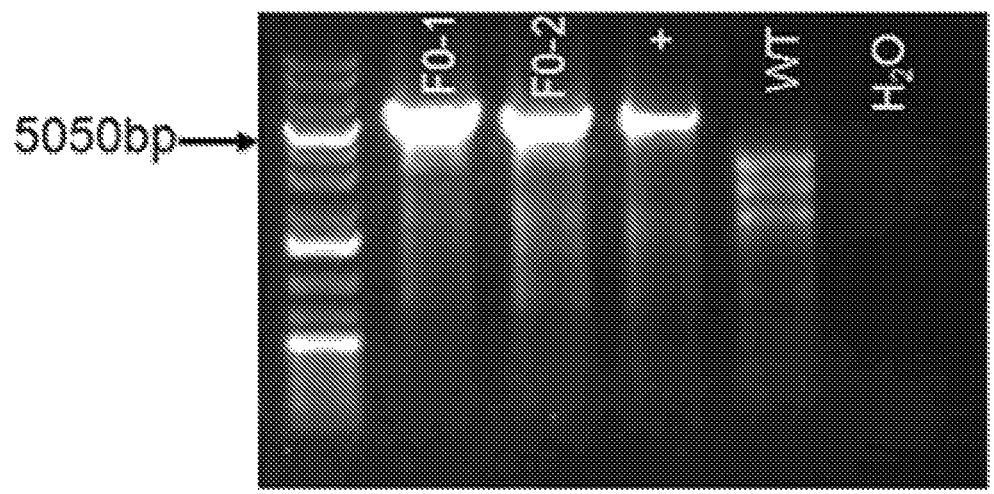
FIGS. 6A-6B show PCR identification results of samples collected from tails of F0 generation mice. WT is wildtype; + is positive control. Mice labeled with F0-1 and F0-2 are positive.
Figure 6B:
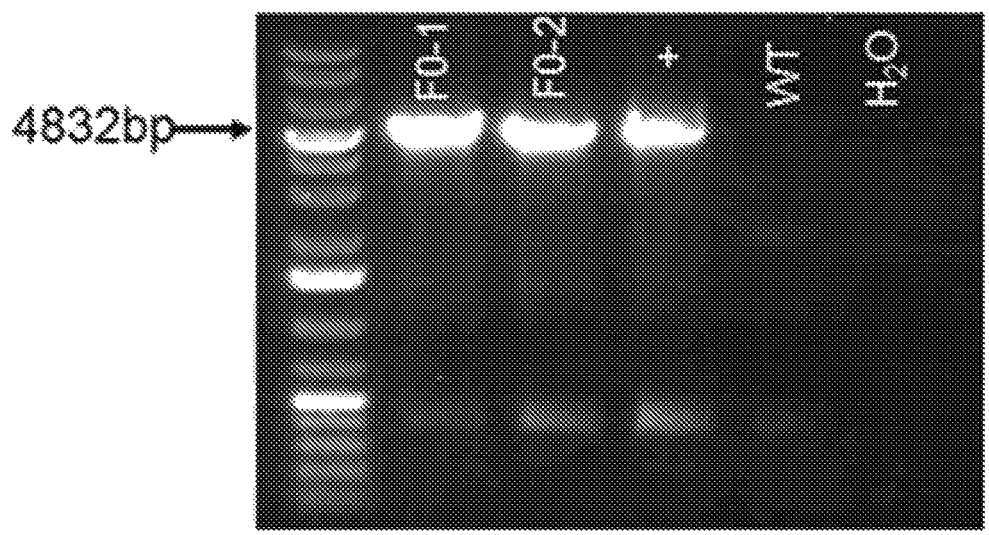

If the desired human sequence was inserted into the correct positions in the genome, PCR experiments using the above primers should generate only one band. The 5' end PCR experiment should produce a band at about 5050 bp, and the 3' end PCR experiment should produce a band at about 4832 bp. The results for F0 generation mice are shown in FIGS. 6A-6B.

TABLE 11

| The PCR reaction (20 μL) | |
|---|---|
| 10× buffer | 2 μL |
| dNTP (2 mM) | 2 μL |
| MgSO$_4$ (25 mM) | 0.8 μL |
| Upstream primer (10 μM) | 0.6 μL |
| Downstream primer (10 μM) | 0.6 μL |
| Mouse tail genomic DNA | 200 ng |
| KOD-Plus-(1 U/μL) | 0.6 μL |
| ddH$_2$O | Add to 20 μL |

TABLE 12

| The PCR reaction conditions | | |
|---|---|---|
| Temperature | Time | Cycles |
| 94° C. | 5 min | 1 |
| 94° C. | 30 sec | 15 |

TABLE 12-continued

| The PCR reaction conditions | | |
|---|---|---|
| Temperature | Time | Cycles |
| 67° C. (−0.7° C./cycle) | 30 sec | |
| 68° C. | 1 kb/min | |
| 94° C. | 10 sec | 25 |
| 56° C. | 30 sec | |
| 68° C. | 1 kb/min | |
| 68° C. | 10 min | 1 |
| 4° C. | 10 min | 1 |

2. Expression Level Analysis in Humanized Mice

One humanized F1 heterozygous mouse was selected. One wildtype mouse in the same background was used as the control.

7.5 μg of anti-mCD3 antibody was injected intraperitoneally to the mice. The spleens were collected 24 hours after the injection, and the spleen samples were grinded. The samples were then passed through 70 μm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed with PBS and tested in FACS.

Figure 7:
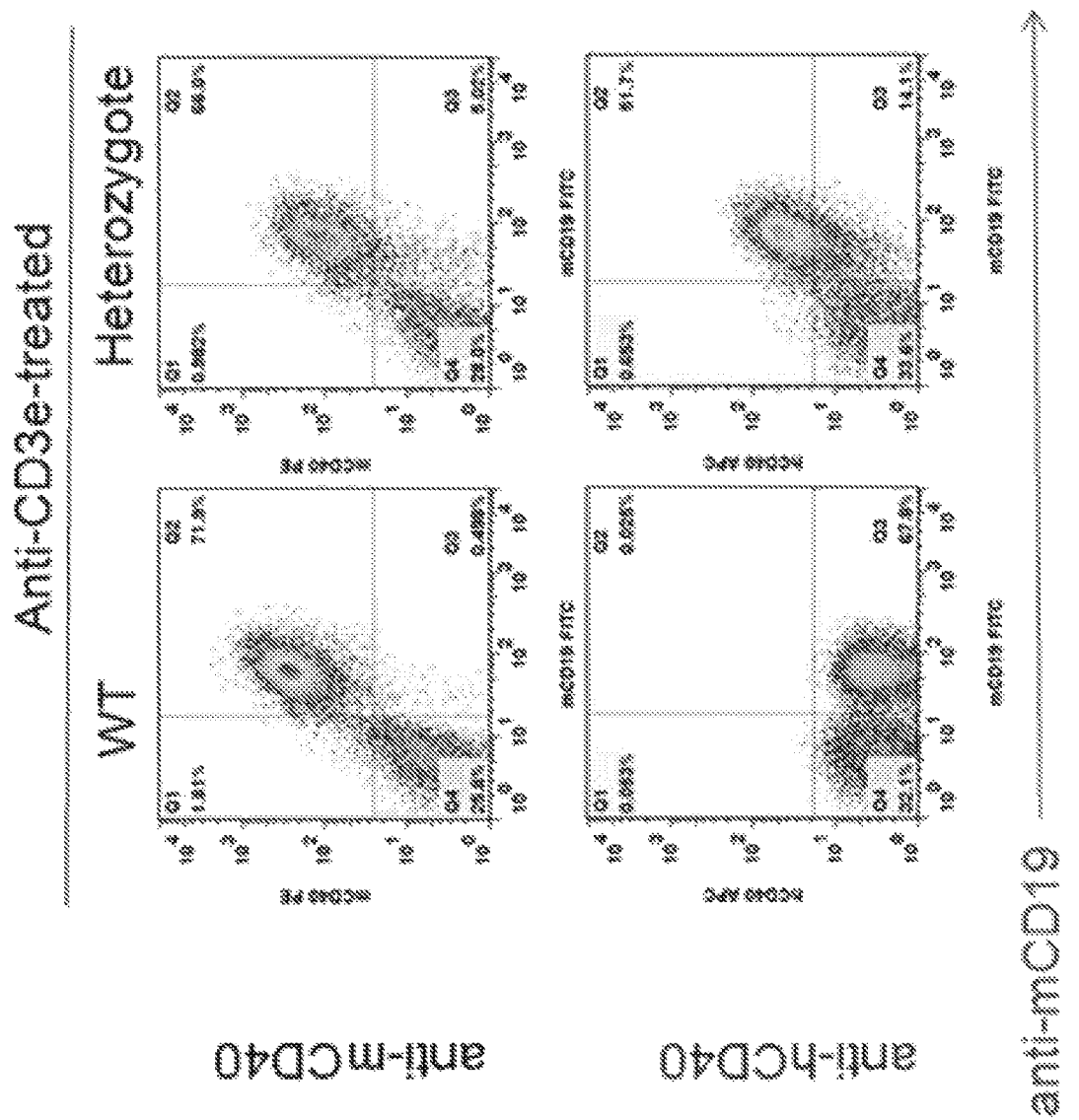
FIG. 7 is flow cytometry results of wildtype mice and heterozygous humanized CD40 mice. Anti-mCD3 antibody was used to activate spleen cells. Flow cytometry was performed with 1) antibody against mouse CD40 (mCD40PE) and antibody against mouse CD19 (mCD19 FITC); and 2) antibody against human CD40 (hCD40 APC), and antibody against mouse CD19 (mCD19 FITC). In the control groups, spleen cells that express human or humanized CD40 were not detected. Humanized CD40 was detected on spleen cells in heterozygous humanized CD40 mice.

Flow cytometry was performed with wildtype mice and F1 generation humanized CD40 mice (FIG. 7). In the control groups, no spleen cells stained with hCD40 APC were observed; in humanized CD40 groups, spleen cells stained with hCD40 APC were observed in heterozygous humanized CD40 mice.

The F1 generation humanized CD40 heterozygotes with the same background were mated with each other to produce humanized CD40 homozygotes. The same experiments described above were performed on these humanized CD40 homozygous mice.

One humanized CD40 homozygous mouse (7 weeks old) was selected. Two wildtype mice in the same background was used as the controls.

7.5 μg of anti-mCD3 antibody was injected intraperitoneally to the mice. The spleens were collected 24 hours after the injection, and the spleen samples were grinded. The samples were then passed through 70 μm cell mesh. The filtered cell suspensions were centrifuged and the supernatants were discarded. Erythrocyte lysis solution was added to the sample, which was lysed for 5 min and neutralized with PBS solution.

Figures 8A, 8B, 8C, 8D, 8E, 8F:
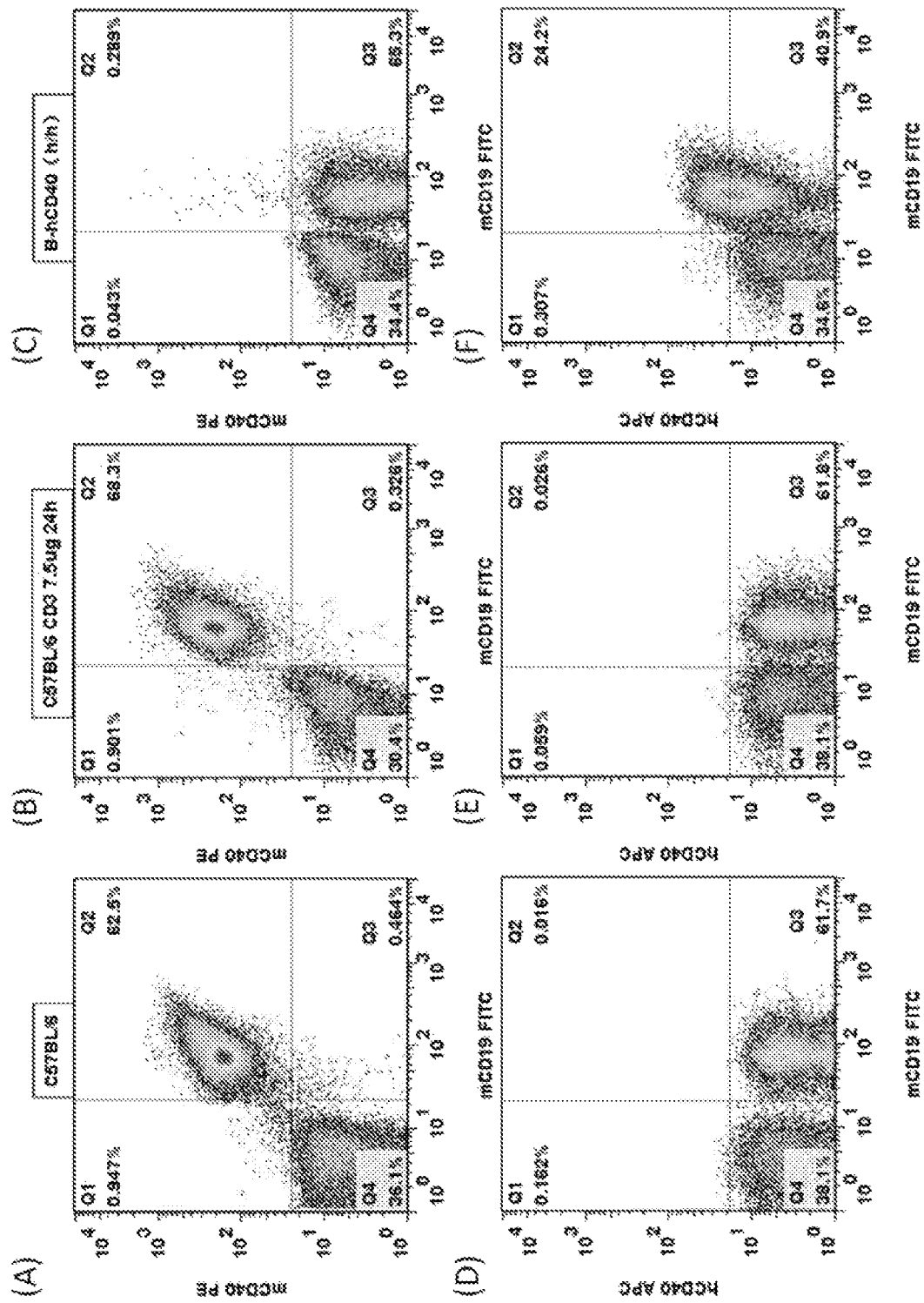
FIGS. 8A-8F are flow cytometry results of wildtype mice (FIGS. 8A, 8B, 8D, and 8E) and humanized CD40 homozygous mice (FIGS. 8C, 8F). CD3 antibody was used to activate spleen cells in FIGS. 8B, 8C, 8E and 8F. Flow cytometry was performed with 1) antibody against mouse CD40 (mCD40PE) and antibody against mouse CD19 (mCD19 FITC) (FIGS. 8A-8C); and 2) antibody against human CD40 (hCD40 APC), and antibody against mouse CD19 (mCD19 FITC) (FIGS. 8D-8F). In the control groups, spleen cells that express human or humanized CD40 were not detected. Humanized CD40 was detected on spleen cells in the homozygous humanized CD40 mice (FIG. 8F).

FACS was performed. The results were shown in FIGS. 8A-8F. In the control groups, no spleen cells stained with hCD40 APC were detected (FIGS. 8D and 8E); in contrast, spleen cells stained with hCD40 APC were observed in homozygous humanized CD40 mice (FIG. 8F).

Example 10: CD40 Knockout Mice

Since the cleavage of Cas9 results in DNA double strands break, and the homologous recombination repair may result in insertion/deletion mutations, it is possible to obtain CD40 knockout mice by the methods described herein. A pair of primers was thus designed to target the left side of the 5' target site and the right side of the 3' target site:

F:

(SEQ ID NO: 45)
5'-GCATCAAGCTTGGTACCGATGTTCTGCGTTCTTGCTTTGGTAGAT G-3'

R:

(SEQ ID NO: 46)
5'-ACTTAATCGTGGAGGATGATCTCATTATCCTTTGGTTTCTTGACC ACC-3'

For wildtype mice, there should be no PCR band, and there should be only one band (about 500 bp) for CD40 knockout mice.

The PCR reaction systems and conditions are shown in the tables below.

TABLE 13

| | |
|---|---|
| 2× PCR buffer | 10 μL |
| dNTP (2 mM) | 4 μL |
| Upstream primer (10 μM) | 0.6 μL |
| Downstream primer (10 μM) | 0.6 μL |
| Genomic DNA from mouse tail | 100 ng |
| KOD-FX (1 U/μL) | 0.4 μL |
| H₂O | Add to 20 μL |

TABLE 14

| Temperature | Duration | Cycles |
|---|---|---|
| 94° C. | 5 min | 1 |
| 98° C. | 30 sec | 35 |
| 62° C. | 30 sec | |
| 68° C. | 30 sec | |
| 68° C. | 10 min | 1 |
| 4° C. | 10 min | 1 |

Figure 9:
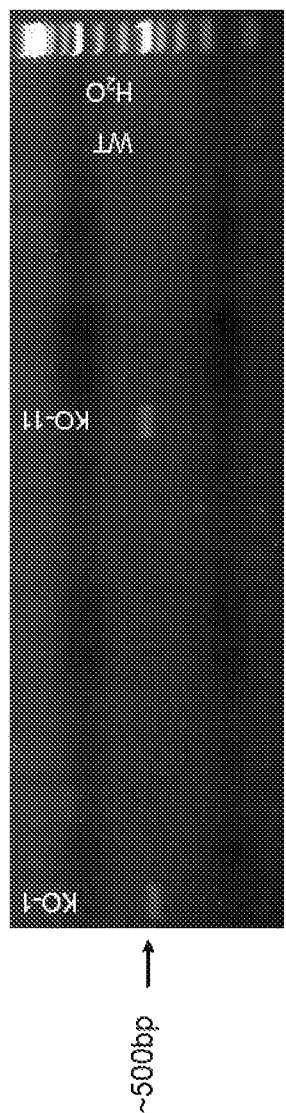
FIG. 9 shows PCR results for CD40 knockout mice. KO-1 and KO-11 were CD40 knockout mice. WT indicates wildtype.

FIG. 9 shows the PCR results. KO-1 and KO-11 were CD40 knockout mice.

Example 11. Pharmacological Validation of B-hCD40 Humanized Animal Model

B-hCD40 heterozygous mice (4 weeks) were subcutaneously injected with mouse colon cancer cell MC38 (5×10⁵/100 μl PBS), and when the tumor volume grew to about 100 mm³, the mice were divided to a control group and six treatment groups based on tumor size (n=5/group). The treatment group were randomly selected for anti-human CD40 antibodies (AB1, AB2, AB3, AB4, AB5, AB6) treatment (3mg/kg); the control group was injected with an equal volume of blank solvent. The frequency of administration was twice a week (6 times of administrations in total). The tumor volume was measured twice a week and the body weight of the mice was weighed as well. Euthanasia was performed when the tumor volume of the mouse reached 3000 mm³. The tested antibodies were generated by immunizing mice with human CD40 proteins. A detailed description of these methods can be found in Murphy, et al., Janeway's immunobiology. Garland Science, 2016 (9$^{th}$ edition), which is incorporated herein by reference in its entirety.

Figure 10:
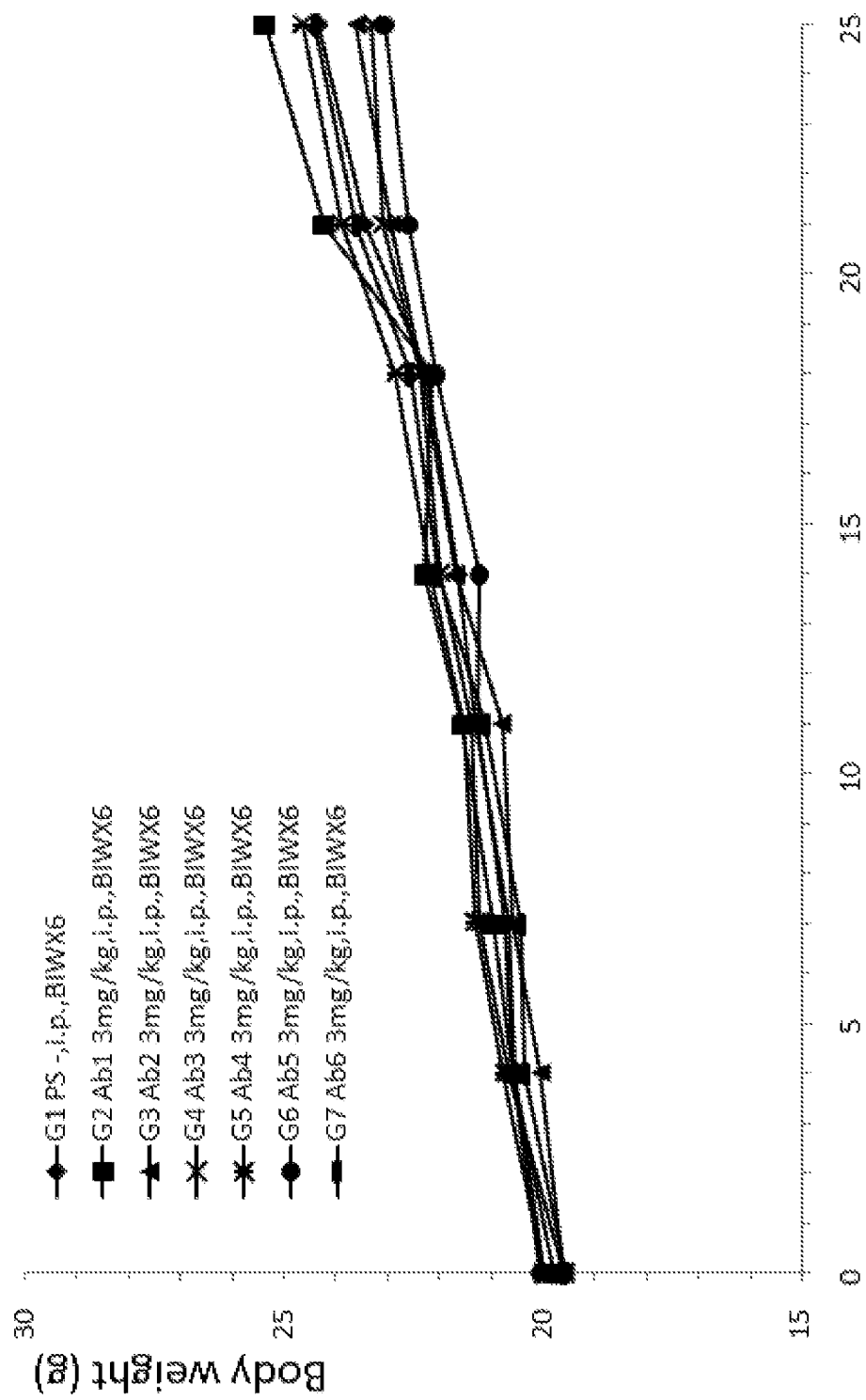
FIG. 10. The average weight of the different groups of humanized CD40 heterozygous mice that were injected with mouse colon cancer cells MC38, and were treated with 6 different anti-human CD40 antibodies (3 mg/kg).
Figure 11:
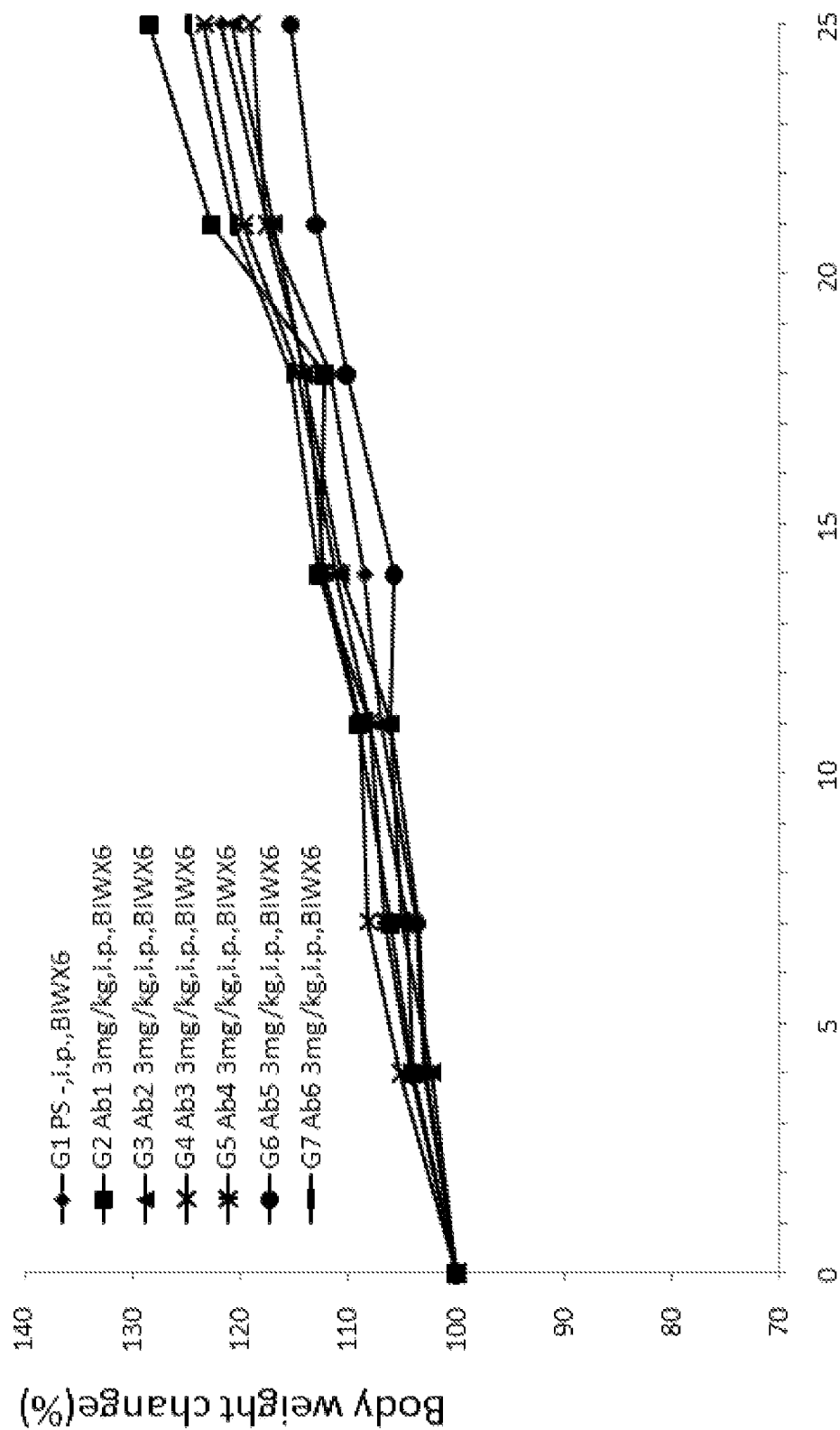
FIG. 11. The percentage change of average weight of the different groups of humanized CD40 heterozygous mice that were injected with mouse colon cancer cells MC38, and were treated with 6 different anti-human CD40 antibodies (3 mg/kg).
Figure 12:
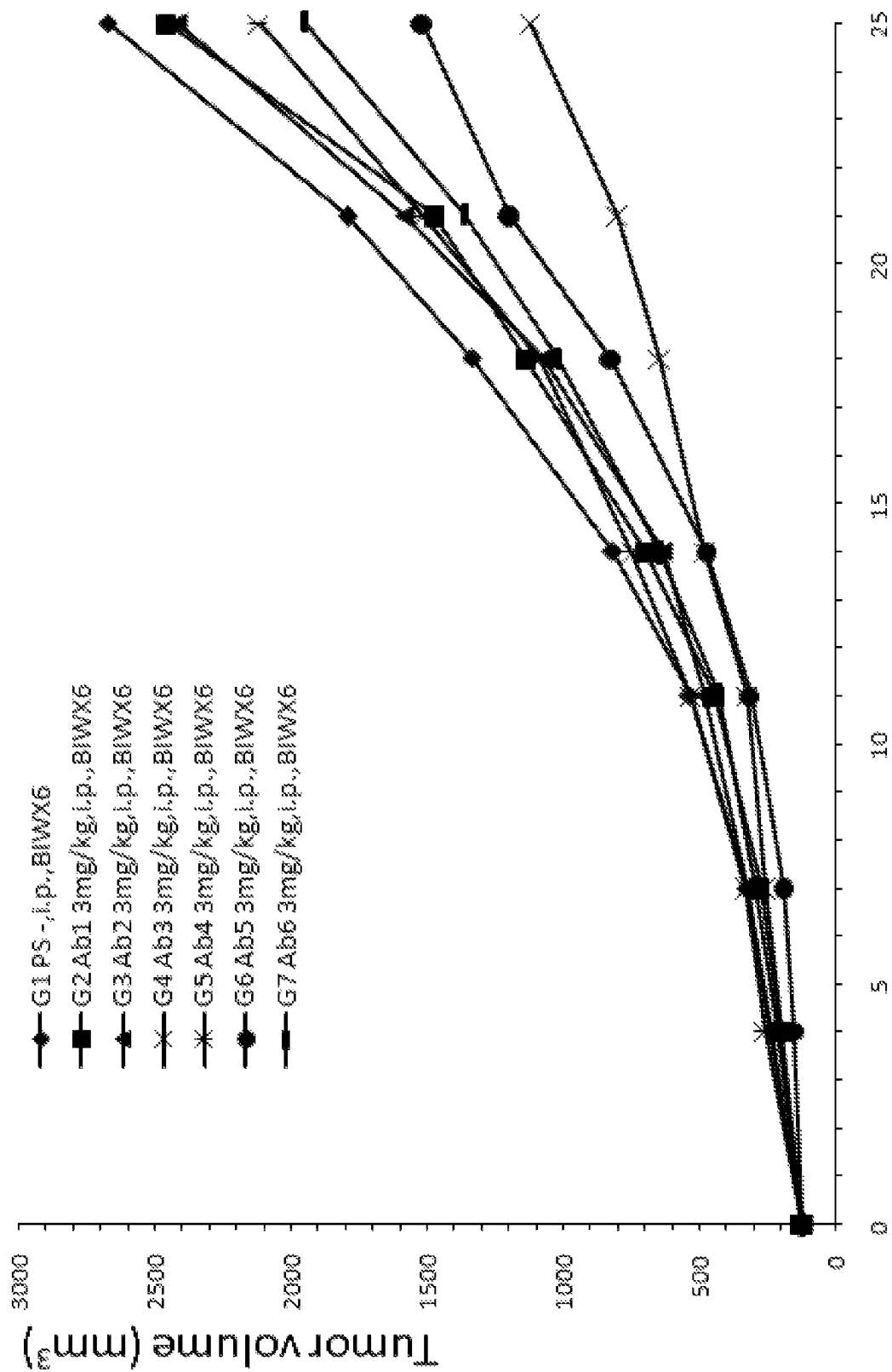
FIG. 12. The average tumor volume in different groups of humanized CD40 heterozygous mice that were injected with mouse colon cancer cells MC38, and were treated with 6 different anti-human CD40 antibodies (3 mg/kg).

Overall, the animals in each group were healthy, and the body weights of all the treatment and control group mice increased, and were not significantly different from each other (FIGS. 10 and 11). The tumor in the control group continued growing during the experimental period (FIG. 12); when compared with the control group mice, the tumor volumes in the treatment groups were smaller than the control group (FIG. 12). Thus, the anti-CD40 antibodies were well tolerated, and the antibodies inhibited the tumor growth in mice.

Table 15 shows results for this experiment, including the tumor volumes at the day of grouping, 14 days after the grouping, and at the end of the experiment (day 25), the survival rate of the mice, the Tumor Growth Inhibition value (TGI$_{TV}$), and the statistical differences (P value) in mouse body weights and tumor volume between the treatment and control groups.

TABLE 15

| | | Tumor volume (mm³) | | | Survival | TGI$_{TV}$ % | P value | |
|---|---|---|---|---|---|---|---|---|
| | | Day 0 | Day 14 | Day 25 | | | Body weight | Tumor Volume |
| Control | G1 | 123 ± 10 | 819 ± 187 | 2677 ± 844 | 5/5 | N/A | N/A | N/A |
| Treatment groups | G2(AB1) | 124 ± 14 | 699 ± 119 | 2460 ± 387 | 5/5 | 8.5 | 0.610 | 0.821 |
| | G3(AB2) | 121 ± 10 | 634 ± 211 | 2424 ± 754 | 5/5 | 9.8 | 0.719 | 0.829 |
| | G4(AB3) | 121 ± 14 | 481 ± 124 | 1124 ± 247 | 5/5 | 60.7 | 0.636 | 0.115 |
| | G5(AB4) | 121 ± 9 | 748 ± 80 | 2121 ± 254 | 5/5 | 21.7 | 0.888 | 0.546 |
| | G6(AB5) | 122 ± 11 | 472 ± 161 | 1522 ± 411 | 5/5 | 45.2 | 0.553 | 0.254 |
| | G7(AB6) | 122 ± 15 | 643 ± 100 | 1954 ± 333 | 5/5 | 28.3 | 0.969 | 0.449 |

At the end of the experiment (day 25), the body weight of each group increased and there was no significant difference between the groups (p>0.05), indicating that the animals tolerated the six anti-hCD40 antibodies well. With respect to the tumor volume, in the control group (G1), the average tumor volume was 2677±844 mm³. The average tumor volumes in the treatment groups were 2460±387 mm³ (G2), 2424±754 mm³ (G3), 1124±247 mm³ (G4), 2121±254 mm³ (G5), 1522±411 mm³ (G6), and 1954±333 mm³ (G7).

The tumor volumes in all treatment groups (G2-G7) were smaller than those in the control group (G1). The results show that anti-human CD40 antibody AB1, AB2, AB3, AB4, AB5, AB6 had different tumor inhibitory effects in B-hCD40 mice. Under the same condition, the inhibitory effects of AB3 (G4) were better than other CD40 antibodies (>60%). These antibodies had no obvious toxic effects in mice.

Figure 13:
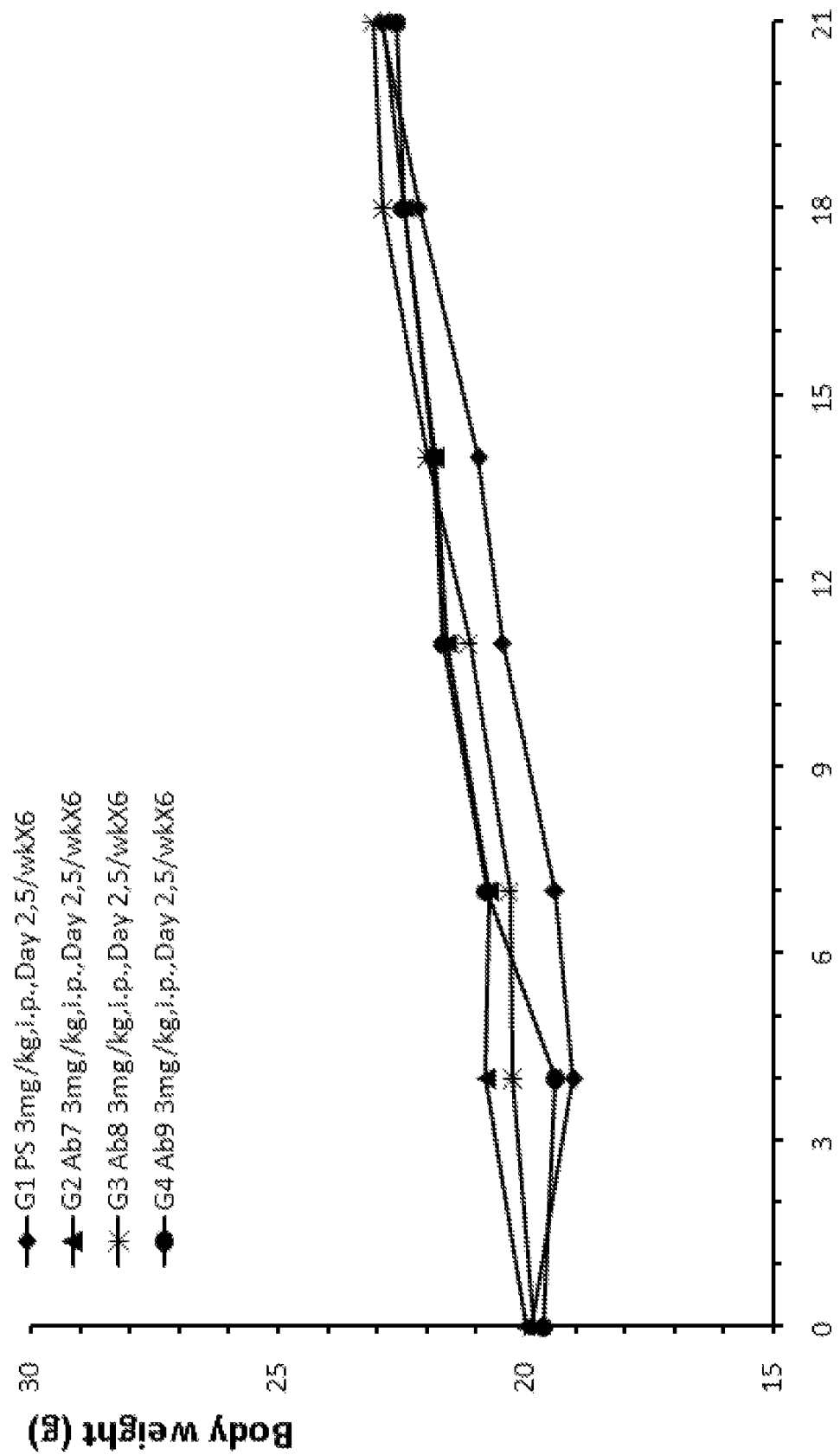
FIG. 13. The average weight of the different groups of humanized CD40 homozygous mice that were injected with mouse colon cancer cells MC38, and were treated with 3 different anti-human CD40 antibodies (3 mg/kg).
Figure 14:
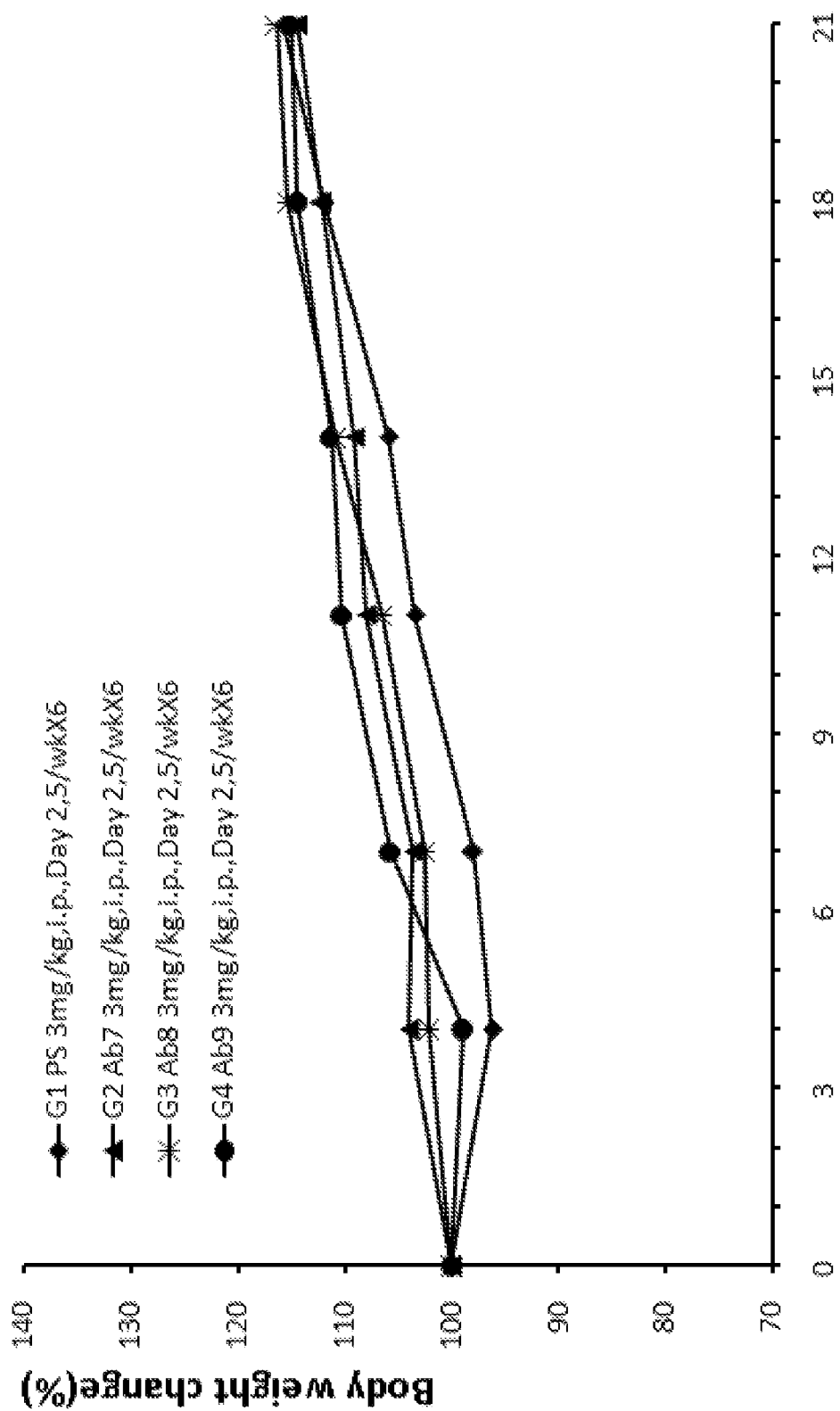
FIG. 14. The percentage change of average weight of the different groups of humanized CD40 homozygous mice that were injected with mouse colon cancer cells MC38, and were treated with 3 different anti-human CD40 antibodies (3 mg/kg).
Figure 15:
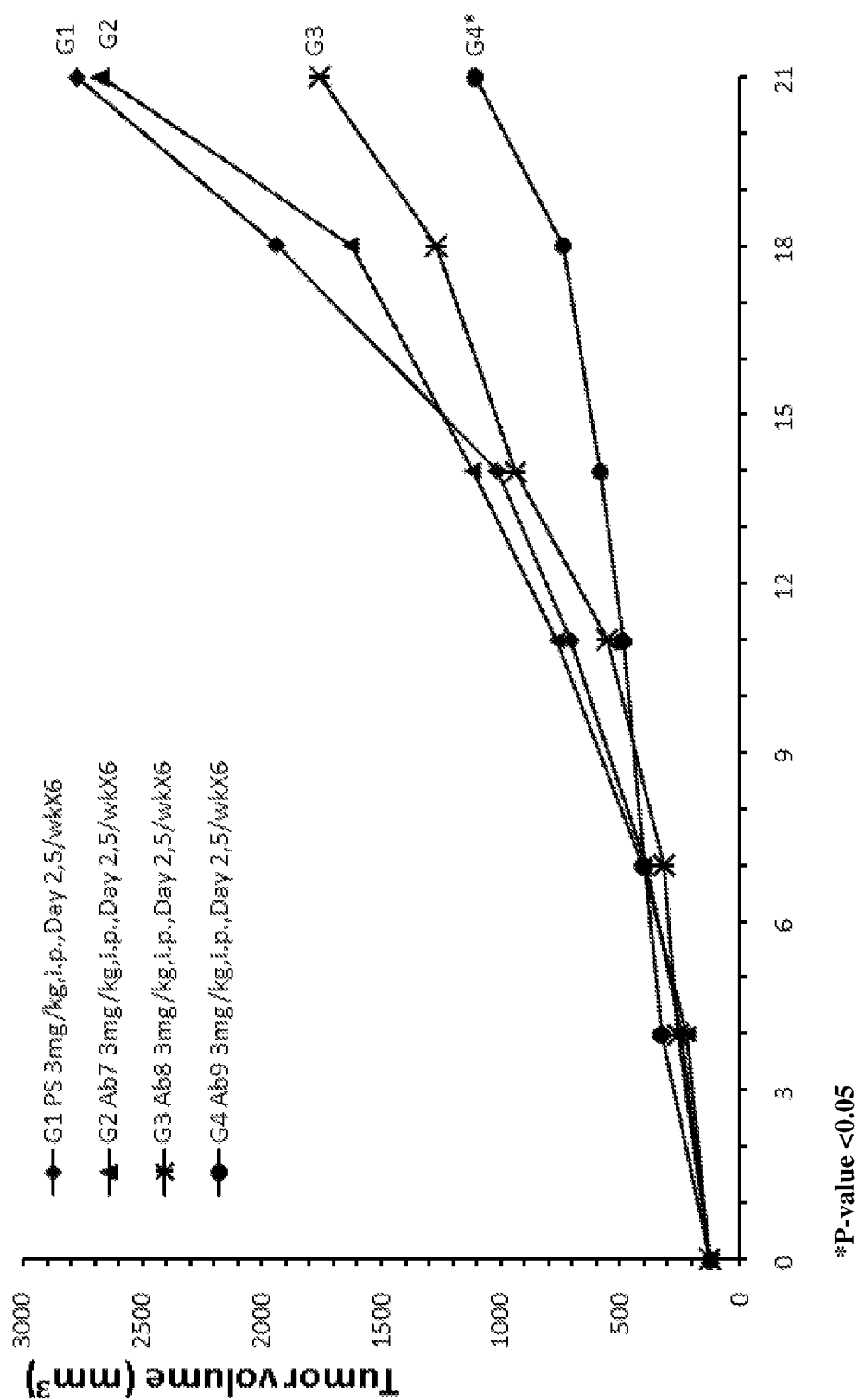
FIG. 15. The average tumor volume in different groups of humanized CD40 homozygous mice that were injected with mouse colon cancer cells MC38, and were treated with 3 different anti-human CD40 antibodies (3 mg/kg).

In another experiment, three additional anti-hCD40 antibodies (AB7, AB8, and AB9) were tested in B-hCD40 homozygous mice. The methods were the same as described above. The body weight of mice and the percentage changes during the experimental period are shown in FIGS. 13 and 14. The results of tumor volumes are shown in FIG. 15. The results of the experiments are also summarized in the table below.

TABLE 16

| | | Tumor volume (mm³) | | | | P value | |
|---|---|---|---|---|---|---|---|
| | | Day 0 | Day 14 | Day 21 | Survival | $TGI_{TV}$% | Body weight | Tumor Volume |
| Control | G1 | 126 ± 5 | 1014 ± 142 | 2779 ± 425 | 5/5 | N/A | N/A | N/A |
| Treatment groups | G2(AB7) | 125 ± 7 | 1121 ± 171 | 26780 ± 453 | 5/5 | 3.62 | 0.97 | 0.875 |
| | G3(AB8) | 125 ± 7 | 938 ± 165 | 1759 ± 340 | 5/5 | 36.7 | 0.76 | 0.098 |
| | G4(AB9) | 125 ± 7 | 583 ± 60 | 1107 ± 153 | 5/5 | 60.7 | 0.74 | 0.006 |

The above examples have demonstrated that the B-hCD40 mouse model can be used as an in vivo animal model for screening, evaluating human CD40 signaling pathway regulators, and testing the efficacy of multiple anti-human CD40 antibodies.

Example 12: Mice with Two or More Humanized Genes

Figures 16A, 16B, 16C, 16D:
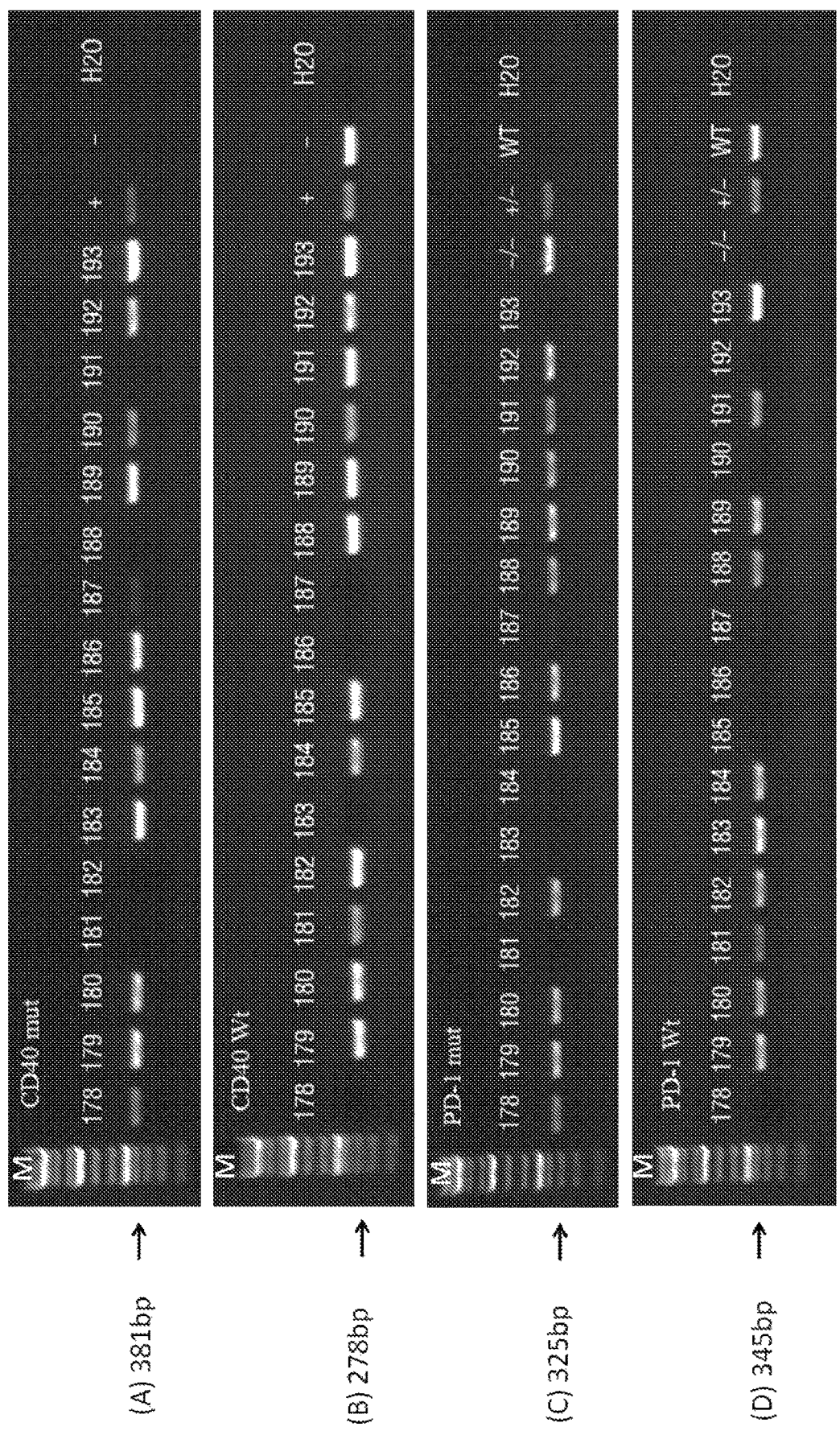
FIGS. 16A-16B show identification results from PCR. − indicates wildtype. + is the humanized CD40 heterozygous mouse positive control.
FIGS. 16C-16D show identification results from PCR. WT indicates wildtype, +/− is the humanized PD-1 heterozygous mouse positive control, −/− is the humanized PD-1 homozygous mouse positive control.

Mice with the humanized CD40 gene (e.g., animal model with humanized CD40 prepared using the methods as described in the present disclosure) can also be used to prepare an animal model with double-humanized or multi-humanized genes. For example, in Example 8, the embryonic stem cell used in the microinjection and embryo transfer process can be selected from the embryos of other genetically modified mice, so as to obtain double- or multiple-gene modified mouse models. The fertilized eggs of mice. Four pairs of primers were used. The specific sequences, the product lengths, the reaction conditions are shown in the tables below. The results for a number of humanized CD40/PD-1 mice are shown in FIGS. 16A-16D, wherein FIGS. 16A and 16B show that the mice numbered 178, 183, 186, and 187 were homozygous for humanized CD40. Mice numbered 179, 180, 184, 185, 189, 190, 192, and 193 were heterozygous for humanized CD40. FIGS. 16C and 16D show that the mice numbered 178, 185, 186, 190, and 192 were homozygous for humanized PD-1, and mice numbered 179, 180, 182, 187, 188, 189 and 191 were heterozygous for humanized PD-1. The results show that the mice numbered 178 and 186 were homozygous for both humanized CD40 and humanized PD-1 ($CD40^{H/H}$/$PD-1^{H/H}$). Mice numbered 179, 180, and 189 were heterozygous for both humanized CD40 and humanized PD-1 ($CD40^{H/+}$/$PD-1^{H/+}$).

In the case of generating double humanized CD40/PD-1 mice, since the mouse CD40 gene and PD-1 gene are located on different chromosomes, the double humanized CD40/PD-1 mouse model was obtained by crossing the CD40 humanized mice with PD-1 humanized mice (e.g., B-hPD-1 mice).

PCR analysis was performed on the genomic DNA collected from mouse tails of double humanized CD40/PD-1

TABLE 17

Primer sequences

| Primer | Sequence | Product length |
|---|---|---|
| CD40 WT F: | 5'-acatgccggtggaagatccc-3' (SEQ ID NO: 47) | WT: 278 bp |
| R: | 5'-gagacgggacagcttggggt-3' (SEQ ID NO: 48) | |
| CD40 MUT F: | 5'-agacatctgccagccacatttccc-3' (SEQ ID NO: 49) | Mut: 381 bp |
| R: | 5'-ctcattatcctttggtttcttgaccacc-3' (SEQ ID NO: 50) | |
| PD-1 MUT F: | 5'-cttccacatgagcgtggtcagggcc-3' (SEQ ID NO: 51) | Mut: 325 bp |
| R: | 5'-ccaagggactattttagatgggcag-3' (SEQ ID NO: 52) | |
| PD-1 WT F: | 5'-gaagctacaagctcctaggtaggggg-3' (SEQ ID NO: 53) | WT: 345 bp |
| R: | 5'-acgggttggctcaaaccattaca-3' (SEQ ID NO: 54) | |

B-hCD40 mice can also be further genetically engineered to produce mouse lines with one or more humanized or otherwise genetically modified mouse models. In addition, the humanized CD40 animal model homozygote or heterozygote can be mated with other genetically modified homozygous or heterozygous animal models (or through IVF), and the progeny can be screened. According to the Mendelian law, there is a chance to obtain the double-gene or multiple-gene modified heterozygous animals, and then the heterozygous animals can be mated with each other to finally obtain the double-gene or multiple-gene modified homozygotes.

TABLE 18

PCR reaction system

| Composition | Volume |
|---|---|
| 2x Master Mix | 10 μL |
| Upstream primer (10 μM) | 0.5 μL |
| Downstream primer (10 μM) | 0.5 μL |

TABLE 18-continued

| PCR reaction system | |
|---|---|
| Composition | Volume |
| Mouse tail genomic DNA (100-200 ng/20 ml) | 2 µL |
| ddH$_2$O | Add to 20 µL |

TABLE 19

| PCR amplification reaction condition | | |
|---|---|---|
| Temperature | Time | Cycles |
| 95° C. | 5 min | 1 |
| 95° C. | 30 sec | 30 |
| 59° C. | 30 sec | |
| 72° C. | 30 sec | |
| 72° C. | 10 min | 1 |
| 4° C. | 10 min | 1 |

Figures 17A, 17B, 17C, 17D, 17E, 17F:
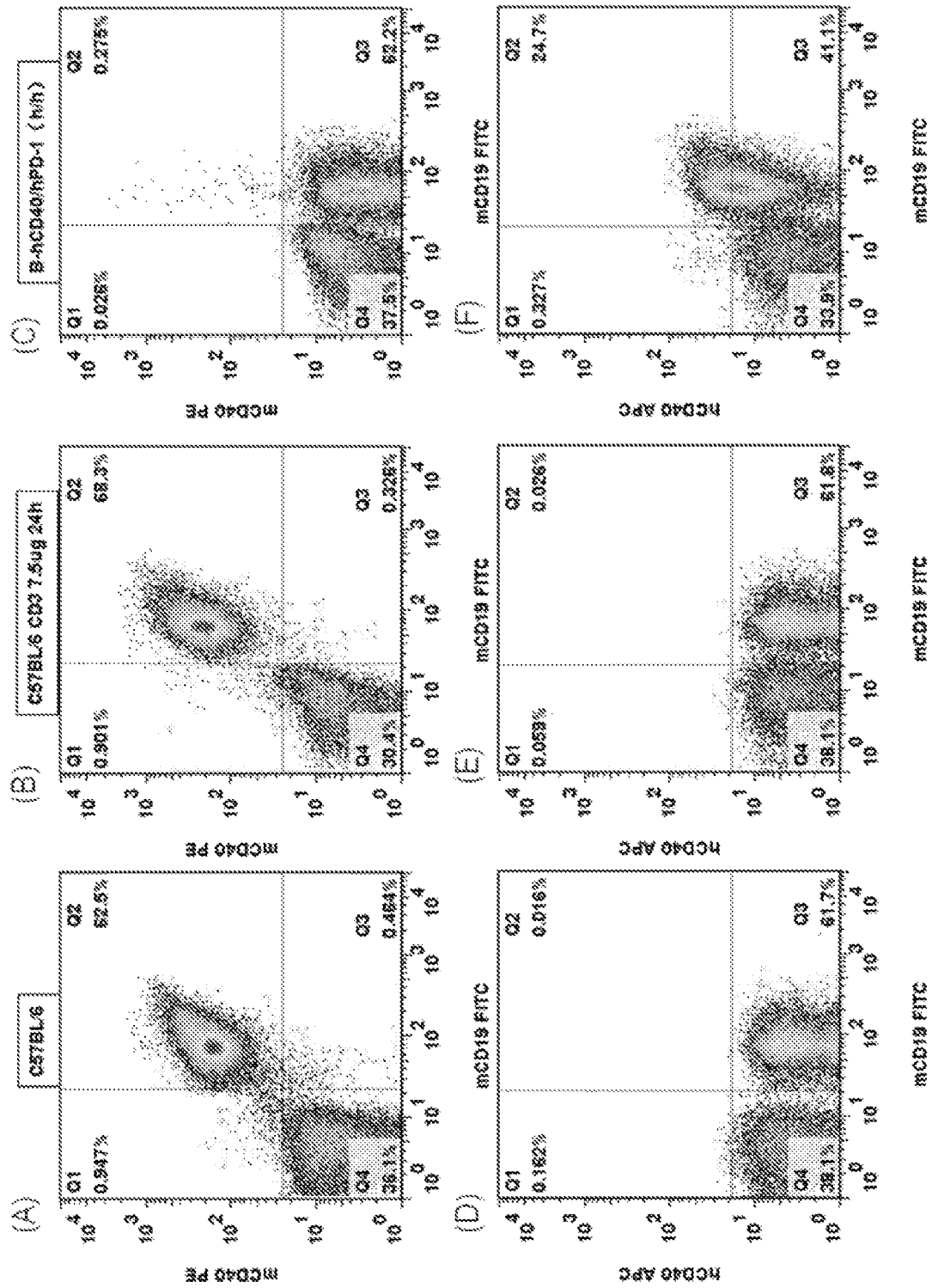
FIGS. 17A-17F are flow cytometry results of wildtype C57BL/6 mice (FIGS. 17A, 17B, 17D, and 17E) and double humanized homozygous $CD40^{H/H}/PD-1^{H/H}$ mice (FIGS. 17C, 17F). Mouse CD3 antibody was used to activate spleen cells in FIGS. 17B, 17C, 17E and 17F. Flow cytometry was performed with antibody against mouse CD40 (mCD40 PE) and antibody against human CD40 (hCD40 APC).
Figures 18A, 18B, 18C, 18D, 18E, 18F:
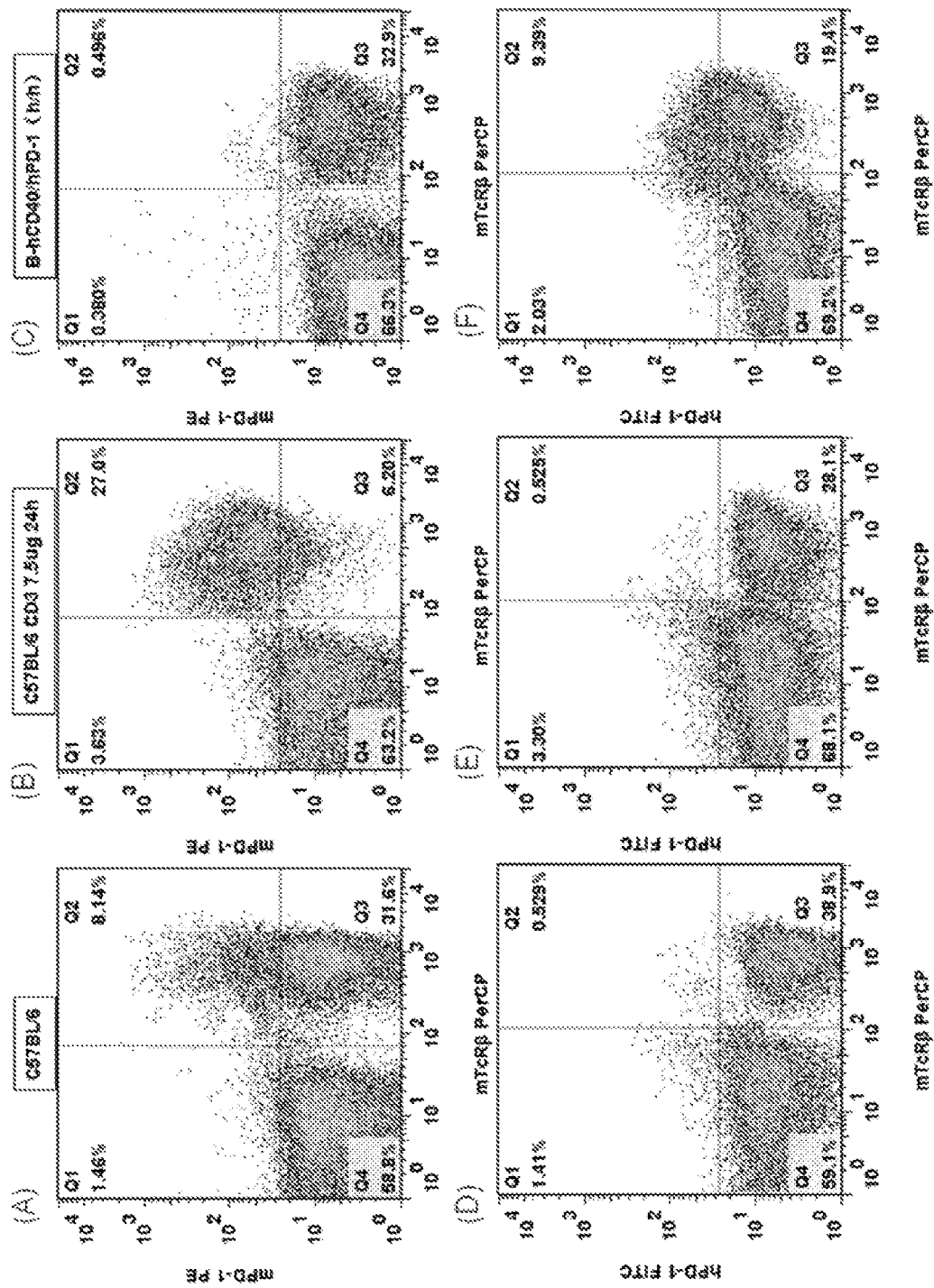
FIGS. 18A-18F are flow cytometry results of wildtype C57BL/6 mice (FIGS. 18A, 18B, 18D, and 18E) and double humanized homozygous $CD40^{H/H}/PD-1^{H/H}$ mice (FIGS. 18C, 18F). Mouse CD3 antibody was used to activate spleen cells in FIGS. 18B, 18C, 18E and 18F. Flow cytometry was performed with antibody against mouse PD-1 (mPD-1 PE) and antibody against human PD-1 (hPD-1 FITC).

Protein expression in the double humanized CD40/PD-1 mice was further examined. A double humanized CD40/PD-1 homozygote was selected for the study. As shown in FIGS. 17A-17F and FIGS. 18A-18F, anti-hCD40 APC and anti-hPD-1 FITC antibodies detected the expression of humanized CD40 and humanized PD-1 on the spleen cells of the double humanized CD40/PD-1 homozygous mouse (FIGS. 17F and 18F). Anti-hCD40 APC and anti-hPD-1 FITC antibodies did not detect the expression of humanized CD40 or humanized PD-1 on the spleen cells of the wildtype mice.

Example 13: Double Humanized CD40/PD-L1 Mice

Since the mouse CD40 gene is located on chromosome 2 and PD-L1 gene is located on chromosome 19, the double humanized CD40/PD-L1 mouse model was obtained by crossing the CD40 humanized mice with PD-L1 humanized mice.

Figures 19A, 19B, 19C, 19D:
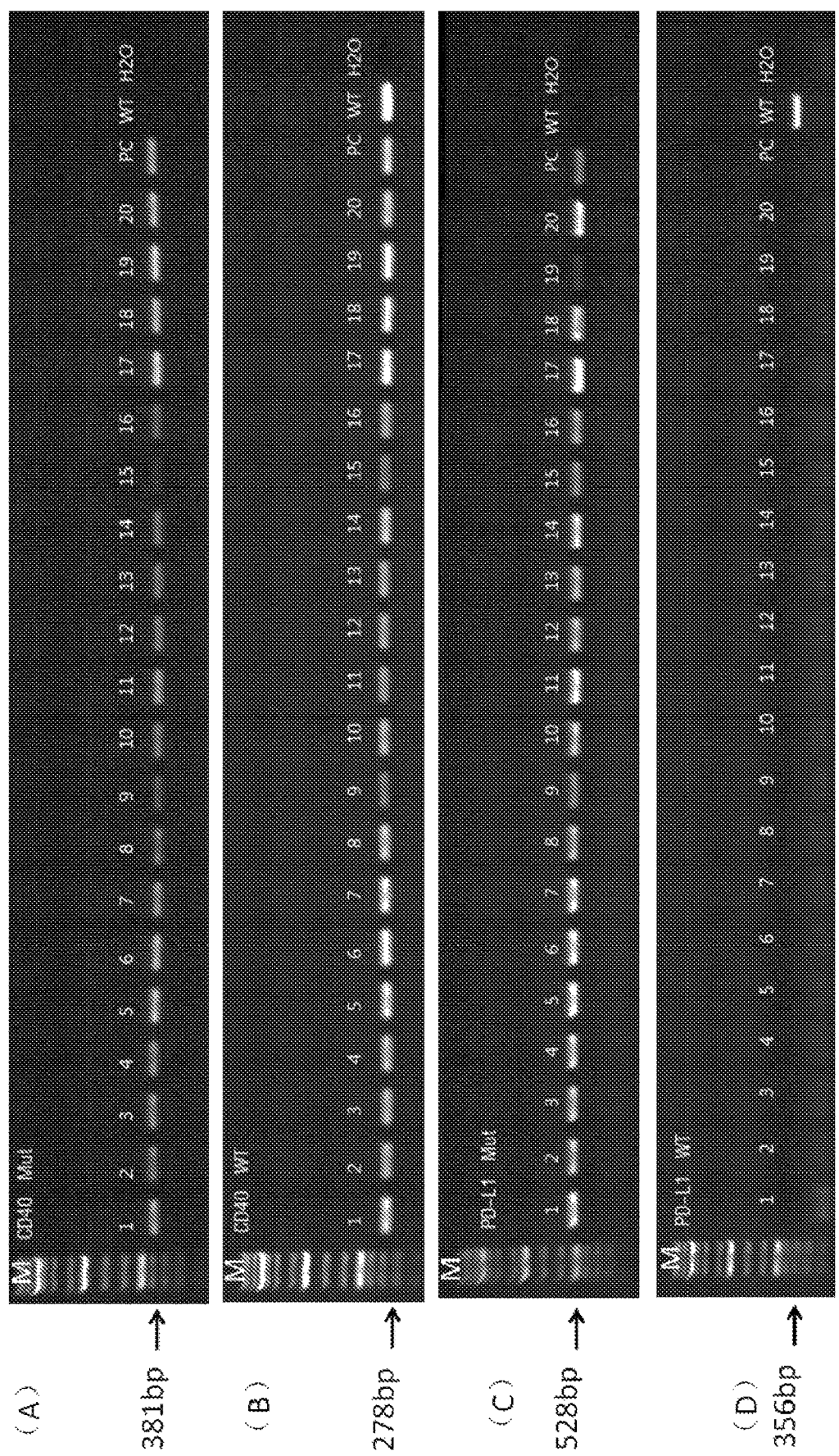
FIGS. 19A-19B show PCR identification results. WT is wildtype; PC is the humanized CD40 heterozygous mouse positive control.
FIGS. 19C-19D show PCR identification results. WT is wildtype; PC is the humanized PD-L1 homozygous mouse positive control.

PCR analysis was performed on the genomic DNA collected from mouse tails of double humanized CD40/PD-L1 mice. Four pairs of primers were used. The specific sequences, the product lengths, and the reaction conditions are shown in tables below. The results for a number of humanized CD40/PD-L1 mice are shown in FIGS. 19A-19D. FIGS. 19A and 19B show that the mice numbered 1-20 were heterozygous for humanized CD40. FIGS. 19C and 19D show that the mice numbered 1-20 were homozygous for humanized PD-L1. Thus, the mice numbered 1-20 were CD40$^{H/+}$/PD-L1$^{H/H}$ mice.

Example 14. Methods Based on Embryonic Stem Cell Technologies

The non-human mammals described herein can also be prepared through other gene editing systems and approaches, including but not limited to: gene homologous recombination techniques based on embryonic stem cells (ES), zinc finger nuclease (ZFN) techniques, transcriptional activator-like effector factor nuclease (TALEN) technique, homing endonuclease (megakable base ribozyme), or other techniques.

Figure 21:
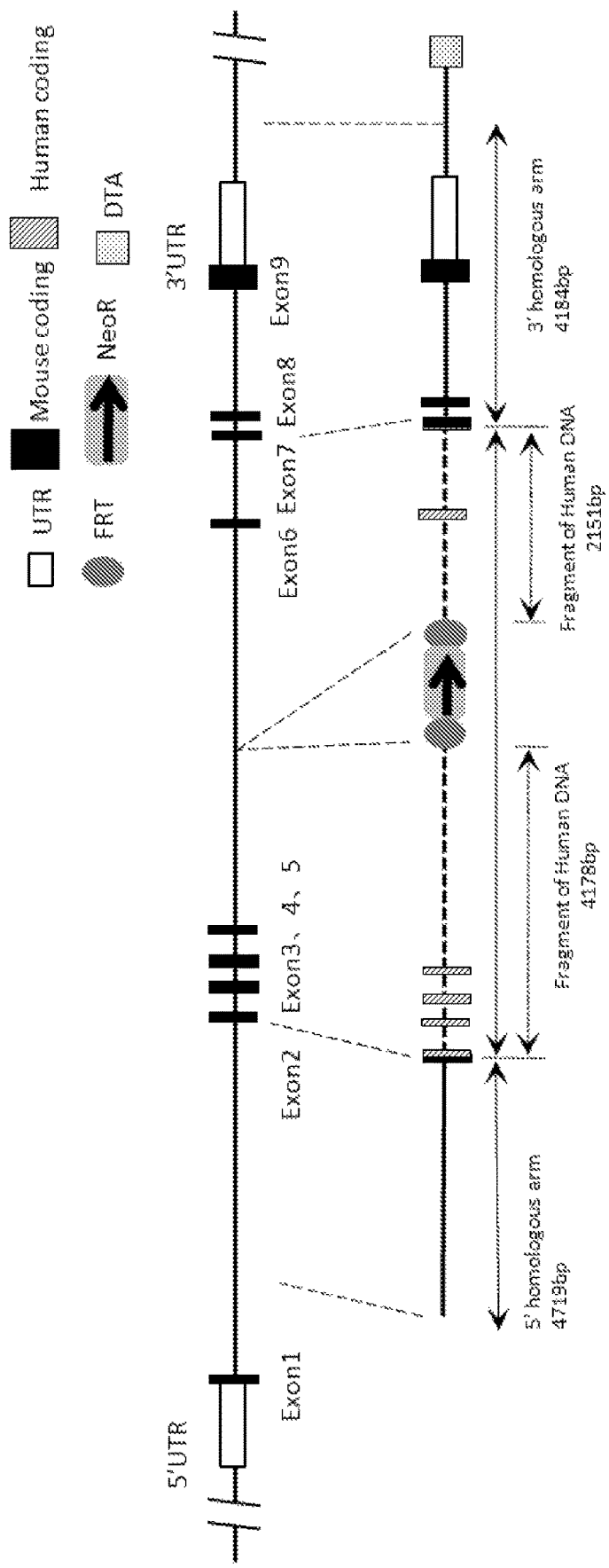
FIG. 21 is a schematic diagram showing gene targeting strategy based on embryonic stem cells.

Based on the CD40 transcript and the corresponding protein sequence and the humanized CD40 mouse gene map as shown in FIG. 4, a targeting strategy for generating the humanized CD40 mouse model with Embryonic Stem Cell Technologies is developed (FIG. 21). Since the objective is to replace exons 2-7 of the mouse CD40 gene in whole or in part with the corresponding sequence in human CD40 gene, a recombinant vector that contains a 5' homologous arm (4719 bp), a 3' homologous arm (4184 bp) and sequence fragment from human CD40 (total 6329 bp) is designed. The vector can also contain a resistance gene for positive clone screening, such as neomycin phosphotransferase coding sequence Neo. On both sides of the resistance gene, two site-specific recombination systems in the same orientation, such as Frt or LoxP, can be added. Furthermore, a coding gene with a negative screening marker, such as the diphtheria toxin A subunit coding gene (DTA), can be constructed downstream of the recombinant vector 3' homologous arm.

Vector construction can be carried out using methods known in the art, such as enzyme digestion and so on. The recombinant vector with correct sequence can be next transfected into mouse embryonic stem cells, such as C57BL/6 mouse embryonic stem cells, and then the recombinant vector can be screened by positive clone screening gene. The cells transfected with the recombinant vector are next screened by using the positive clone marker gene, and Southern Blot technique can be used for DNA recombination identification. For the selected correct positive clones, the positive clonal cells (black mice) are injected into the isolated blastocysts (white mice) by microinjection according to the method described in the book A. Nagy, et al., "Manipulating the Mouse Embryo: A Laboratory Manual (Third Edition)," Cold Spring Harbor Laboratory Press, 2003. The resulting chimeric blastocysts formed following the injection are transferred to the culture medium for a short time culture and then transplanted into the fallopian tubes of the recipient mice (white mice) to produce F0 generation chimeric mice (black and white). The F0 generation chime-

TABLE 20

| Primer sequences | | | | |
|---|---|---|---|---|
| Primer | | Sequence | | Product length |
| CD40 WT | F: | (SEQ ID NO: 47) | | WT: 278 bp |
| | R: | (SEQ ID NO: 48) | | |
| CD40 MUT | F: | (SEQ ID NO: 49) | | Mut: 381 bp |
| | R: | (SEQ ID NO: 50) | | |
| PD-L1 MUT | F: | 5'-ccagggaggtggcccactgataata-3' | (SEQ ID NO: 55) | Mut: 528 bp |
| | R: | 5'-actaacgcaagcaggtccagctccc-3' | (SEQ ID NO: 56) | |
| PD-L1 WT | F: | 5'-ccagggaggtggcccactgataata-3' | (SEQ ID NO: 55) | WT: 356 bp |
| | R: | 5'-cacccctgcatcctgcaatttcaca-3' | (SEQ ID NO: 58) | | ric mice with correct gene recombination are then selected by extracting the mouse tail genome and detecting by PCR for subsequent breeding and identification. The F1 generation mice are obtained by mating the F0 generation chimeric mice with wildtype mice. Stable gene recombination positive F1 heterozygous mice are selected by extracting rat tail genome and PCR detection. Next, the F1 heterozygous mice are mated to each other to obtain genetically recombinant positive F2 generation homozygous mice. In addition, the F1 heterozygous mice can also be mated with Flp or Cre mice to remove the positive clone screening marker gene (e.g., neo), and then the CD40 gene humanized homozygous mice can be obtained by mating these mice with each other. The methods of genotyping and using the F1 heterozygous mice or F2 homozygous mice are similar to the methods as described in the examples above.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified mouse whose genome comprises a sequence encoding a humanized CD40 at the endogenous CD40 gene locus under the control of endogenous regulatory elements, wherein the humanized CD40 comprises the amino acid sequence as set forth in SEQ ID NO: 27, wherein the mouse expresses a humanized CD40 comprising a humanized extracellular region and an endogenous cytoplasmic region.

2. The mouse of claim 1, wherein the mouse comprises a homozygous deletion of the endogenous mouse CD40 gene, and the mouse does not express mouse CD40.

3. A method of determining effectiveness of an anti-CD40 antibody for treating cancer, comprising:
 administering the anti-CD40 antibody to the mouse of claim 1, wherein the mouse has a tumor; and
 determining inhibitory effects of the anti-CD40 antibody to the tumor.

4. The mouse of claim 1, wherein the mouse further comprises a sequence encoding a human or chimeric Programmed Cell Death Protein 1 (PD-1) or a human or chimeric Programmed Cell Death 1 Ligand 1 (PD-L1).

* * * * *

```
                        SEQUENCE LISTING

<160> NUMBER OF SEQ ID NOS: 61

<210> SEQ ID NO 1
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 1
gacaaacagt acctccacga tgg                                             23

<210> SEQ ID NO 2
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 2
cgggacagct tggggtattc tgg                                             23

<210> SEQ ID NO 3
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 3
acgtaacaca ctgccctaga tgg                                             23

<210> SEQ ID NO 4
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 4
gggtcttggt acggggcagg agg                                             23

<210> SEQ ID NO 5
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 5
gcatccacca gcaatccaag agg                                             23
```

```
<210> SEQ ID NO 6
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 6
tctcagaccc tacacgagta agg                                              23

<210> SEQ ID NO 7
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 7
acagactgtg tcacaaccca ggg                                              23

<210> SEQ ID NO 8
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 8
cgcatccggg actttaaacc tgg                                              23

<210> SEQ ID NO 9
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 9
tgaccagcag ggctcgcatc cgg                                              23

<210> SEQ ID NO 10
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 10
ccaatggagt gtgctcccac tgg                                              23

<210> SEQ ID NO 11
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 11
actgcttaaa agctctgacc tgg                                              23

<210> SEQ ID NO 12
<211> LENGTH: 23
<212> TYPE: DNA
<213> ORGANISM: Artificial Sequence
<220> FEATURE:
<223> OTHER INFORMATION: sgRNA target sequence
```

```
<400> SEQUENCE: 12
tgtgggtaat gtggtcacta ggg                                              23

<210> SEQ ID NO 13
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 13
tggagtgtgc tcccactggc agg                                              23

<210> SEQ ID NO 14
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 14
cattgggagc acccgccagt ggg                                              23

<210> SEQ ID NO 15
<211> LENGTH: 19
<212> TYPE: DNA
<213> ORGANISM: Artificial Sequence
<220> FEATURE:
<223> OTHER INFORMATION: sgRNA sequence

<400> SEQUENCE: 15
acaaacagta cctccacga                                                   19

<210> SEQ ID NO 16
<211> LENGTH: 19
<212> TYPE: DNA
<213> ORGANISM: Artificial Sequence
<220> FEATURE:
<223> OTHER INFORMATION: sgRNA sequence

<400> SEQUENCE: 16
tcgtggaggt actgtttgt                                                   19

<210> SEQ ID NO 17
<211> LENGTH: 18
<212> TYPE: DNA
<213> ORGANISM: Artificial Sequence
<220> FEATURE:
<223> OTHER INFORMATION: sgRNA sequence

<400> SEQUENCE: 17
catccgggac tttaaacc                                                    18

<210> SEQ ID NO 18
<211> LENGTH: 18
<212> TYPE: DNA
<213> ORGANISM: Artificial Sequence
<220> FEATURE:
<223> OTHER INFORMATION: sgRNA sequence

<400> SEQUENCE: 18
ggtttaaagt cccggatg                                                    18

<210> SEQ ID NO 19
```

```
<211> LENGTH: 132
<212> TYPE: DNA
<213> ORGANISM: Artificial Sequence
<220> FEATURE:
<223> OTHER INFORMATION: Synthesized sequence

<400> SEQUENCE: 19
gaattctaat acgactcact atagggggtc ttcgagaaga cctgttttag agctagaaat      60
agcaagttaa aataaggcta gtccgttatc aacttgaaaa agtggcaccg agtcggtgct     120
tttaaaggat cc                                                         132

<210> SEQ ID NO 20
<211> LENGTH: 1683
<212> TYPE: DNA
<213> ORGANISM: Mus musculus

<400> SEQUENCE: 20
agcagggact ttggagtgac ttgtggcttc agcaggagcc ctgtgatttg gctcttctga      60
tctcgccctg cgatggtgtc tttgcctcgg ctgtgcgcgc tatggggctg cttgttgaca     120
gcggtccatc tagggcagtg tgttacgtgc agtgacaaac agtacctcca cgatggccag     180
tgctgtgatt tgtgccagcc aggaagccga ctgacaagcc actgcacagc tcttgagaag     240
acccaatgcc acccatgtga ctcaggcgaa ttctcagccc agtggaacag ggagattcgc     300
tgtcaccagc acagacactg tgaacccaat caagggcttc gggttaagaa ggagggcacc     360
gcagaatcag acactgtctg tacctgtaag gaaggacaac actgcaccag caaggattgc     420
gaggcatgtg ctcagcacac gccctgtatc cctggctttg gagttatgga gatggccact     480
gagaccactg ataccgtctg tcatccctgc ccagtcggct tcttctccaa tcagtcatca     540
cttttcgaaa agtgttatcc ctggacaagc tgtgaggata gaacttggaa ggtcctacag     600
aaaggaacga gtcagactaa tgtcatctgt ggtttaaagt cccggatgcg agccctgctg     660
gtcattcctg tcgtgatggg catcctcatc accattttcg gggtgtttct ctatatcaaa     720
aaggtggtca agaaaccaaa ggataatgag atcttacccc ctgcggctcg acggcaagat     780
ccccaggaga tggaagatta tcccggtcat aacaccgctg ctccagtgca ggagacgctg     840
cacgggtgtc agcctgtcac acaggaggat ggtaaagaga gtcgcatctc agtgcaggag     900
cggcaggtga cagacagcat agccttgagg ccctggtct gaaccctgga actgctttgg      960
aggcgatggc tcggctcggg agcaggggcc tggctctgag gactgcttgc tgacctttga    1020
agtttgagat gagccaagac agagcccagt gcagctaact ctcatgcctg ccccctatca    1080
tttctcaact tgctttttaa ggatggaggg agagctcggg catcggggt ccacagtgat     1140
acctaccaag tgcagcagtg caggacccag agtcgtcttg ctgcggcgtt cactgtaagg    1200
agtcatggac acaggagtcc gtggcccaca gcttgtgctg ctagagggca cctggttgcc    1260
catcagcagg gtactggcta aataaatctg taattattta tacaatgaca tctcagaaac    1320
tctagcaggt ggggcagaaa acaggtagta gaatgatggg tagagaaata gcttttaaaa    1380
cacattccaa ggcaggtaag atggcttttg tgagtaaagg agcttgctgc caaacccgg     1440
ttacctgatt tgatccctg ggacttcatg gtaaaaggga gagaaccaaa tccagagggt     1500
tgtcatttga cctccatgtg tgctctgtgg taatgtaccc cgtgtgtgca catgtgcaca    1560
tatcctaaaa tggatgtggt ggtgtattgt agaaattatt taatcccgcc ctggggtttc    1620
tacctgtgtg ttaccattta gttcttgaat aaaagacaca ctcaaccttt atatttacaa    1680
taa                                                                  1683
```

<210> SEQ ID NO 21
<211> LENGTH: 289
<212> TYPE: PRT
<213> ORGANISM: Mus musculus

<400> SEQUENCE: 21

Met Val Ser Leu Pro Arg Leu Cys Ala Leu Trp Gly Cys Leu Leu Thr
1               5                   10                  15
Ala Val His Leu Gly Gln Cys Val Thr Cys Ser Asp Lys Gln Tyr Leu
            20                  25                  30
His Asp Gly Gln Cys Cys Asp Leu Cys Gln Pro Gly Ser Arg Leu Thr
        35                  40                  45
Ser His Cys Thr Ala Leu Glu Lys Thr Gln Cys His Pro Cys Asp Ser
    50                  55                  60
Gly Glu Phe Ser Ala Gln Trp Asn Arg Glu Ile Arg Cys His Gln His
65                  70                  75                  80
Arg His Cys Glu Pro Asn Gln Gly Leu Arg Val Lys Lys Glu Gly Thr
                85                  90                  95
Ala Glu Ser Asp Thr Val Cys Thr Cys Lys Glu Gly Gln His Cys Thr
            100                 105                 110
Ser Lys Asp Cys Glu Ala Cys Ala Gln His Thr Pro Cys Ile Pro Gly
        115                 120                 125
Phe Gly Val Met Glu Met Ala Thr Glu Thr Thr Asp Thr Val Cys His
    130                 135                 140
Pro Cys Pro Val Gly Phe Phe Ser Asn Gln Ser Ser Leu Phe Glu Lys
145                 150                 155                 160
Cys Tyr Pro Trp Thr Ser Cys Glu Asp Lys Asn Leu Glu Val Leu Gln
                165                 170                 175
Lys Gly Thr Ser Gln Thr Asn Val Ile Cys Gly Leu Lys Ser Arg Met
            180                 185                 190
Arg Ala Leu Leu Val Ile Pro Val Val Met Gly Ile Leu Ile Thr Ile
        195                 200                 205
Phe Gly Val Phe Leu Tyr Ile Lys Lys Val Val Lys Lys Pro Lys Asp
    210                 215                 220
Asn Glu Ile Leu Pro Pro Ala Ala Arg Arg Gln Asp Pro Gln Glu Met
225                 230                 235                 240
Glu Asp Tyr Pro Gly His Asn Thr Ala Ala Pro Val Gln Glu Thr Leu
                245                 250                 255
His Gly Cys Gln Pro Val Thr Gln Glu Asp Gly Lys Glu Ser Arg Ile
            260                 265                 270
Ser Val Gln Glu Arg Gln Val Thr Asp Ser Ile Ala Leu Arg Pro Leu
        275                 280                 285
Val

<210> SEQ ID NO 22
<211> LENGTH: 1629
<212> TYPE: DNA
<213> ORGANISM: Homo sapiens

<400> SEQUENCE: 22
tttcctgggc ggggccaagg ctggggcagg ggagtcagca gaggcctcgc tcgggcgccc      60
agtggtcctg ccgcctggtc tcacctcgct atggttcgtc tgcctctgca gtgcgtcctc     120
tggggctgct tgctgaccgc tgtccatcca gaaccaccca ctgcatgcag agaaaaacag     180

```
tacctaataa acagtcagtg ctgttctttg tgccagccag gacagaaact ggtgagtgac    240
tgcacagagt tcactgaaac ggaatgcctt ccttgcggtg aaagcgaatt cctagacacc    300
tggaacagag agacacactg ccaccagcac aaatactgcg accccaacct agggcttcgg    360
gtccagcaga agggcacctc agaaacagac accatctgca cctgtgaaga aggctggcac    420
tgtacgagtg aggcctgtga gagctgtgtc ctgcaccgct catgctcgcc cggcttcggg    480
gtcaagcaga ttgctacagg ggtttctgat accatctgcg agccctgccc agtcggcttc    540
ttctccaatg tgtcatctgc tttcgaaaaa tgtcacccct ggacaagctg tgagaccaaa    600
gacctggttg tgcaacaggc aggcacaaac aagactgatg ttgtctgtgg tccccaggat    660
cggctgagag ccctggtggt gatccccatc atcttcggga tcctgtttgc catcctcttg    720
gtgctggtct ttatcaaaaa ggtggccaag aagccaacca ataaggcccc cacccccaag    780
caggaacccc aggagatcaa ttttcccgac gatcttcctg ctccaacac tgctgctcca    840 gtgcaggaga ctttacatgg atgccaaccg gtcacccagg aggatggcaa agagagtcgc    900
atctcagtgc aggagagaca gtgaggctgc acccacccag gagtgtggcc acgtgggcaa    960
acaggcagtt ggccagagag cctggtgctg ctgctgctgt ggcgtgaggg tgaggggctg   1020
gcactgactg ggcatagctc cccgcttctg cctgcacccc tgcagtttga dacaggagac   1080
ctggcactgg atgcagaaac agttcacctt gaagaacctc tcacttcacc ctggagccca   1140
tccagtctcc caacttgtat taaagacaga ggcagaagtt tggtggtggt ggtgttgggg   1200
tatggtttag taatatccac cagaccttcc gatccagcag tttggtgccc agagaggcat   1260
catggtggct tccctgcgcc caggaagcca tatacagca tgcccattgc agcattgttt    1320
gtgatagtga caactggaa gctgcttaac tgtccatcag caggagactg gctaaataaa   1380
attagaatat atttatacaa cagaatctca aaaacactgt tgagtaagga aaaaaggca   1440 tgctgctgaa tgatgggtat ggaacttttt aaaaaagtac atgctttat gtatgtatat   1500 tgcctatgga tatatgtata aatacaatat gcatcatata ttgatataac aagggttctg   1560
gaagggtaca cagaaaaccc acagctcgaa gagtggtgac gtctggggtg gggaagaagg   1620
gtctgggggg                                                          1629
```

<210> SEQ ID NO 23
<211> LENGTH: 277
<212> TYPE: PRT
<213> ORGANISM: Homo sapiens

<400> SEQUENCE: 23

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110
```

Ser Glu Ala Cys Glu Ser Cys Val Leu His Arg Ser Cys Ser Pro Gly
                115                 120                 125

Phe Gly Val Lys Gln Ile Ala Thr Gly Val Ser Asp Thr Ile Cys Glu
        130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275

<210> SEQ ID NO 24
<211> LENGTH: 6863
<212> TYPE: DNA
<213> ORGANISM: Artificial Sequence
<220> FEATURE:
<223> OTHER INFORMATION: Homo sapiens and Mus musculus

<400> SEQUENCE: 24
gagcactgaa gagtcctgtg catctgttcg gattagaggg ttctgcgttc ttgctttggt      60
agatggcagt aagacgatgt gacaacagag taaaaaaaaa aatagacctc acactctggg     120
ggctcacttt tctgctttgg atttccacat cagctacagc ctgcgtcttg gctaactttc     180
aacatgccgg tggaagatcc cttccagctg tccacttctg tttttaggtc catccagaac     240
cacccactgc atgcagagaa aaacagtacc taataaacag tcagtgctgt tctttgtgcc     300
agccaggtga gatgccaacc tctagcccca tcatggagt ccccctttgc tttggtggca     360
gacgcagacc ccatatgtta actgtaaact caaatctgaa acgacccatt tcccagccct     420
gcttcactgt cagaatgttc tggttccctc tctaccaggt aaaactctgt ctaccctgaa     480
ctagggatcc cagcttctcc atcttcctcg cctgattatg aaggatccaa gactttcatc     540
tttgaatccc ctaccctaaa gcctggcctg atcattgtgt ggttagtgtc tgactcatgg     600
agttggccag agccctccct catttcctga tgttttccag acagaaact ggtgagtgac      660 tgcacagagt tcactgaaac ggaatgcctt ccttgcggtg aaagcgaatt cctagacacc     720
tggaacagag agacacactg ccaccagcac aaatactgcg accccagtgc gtgcgctgtt     780
gggaaaggga cgcttgggaa ccgggctgat attcccgaca atgcagccat tctaattta      840 tgtagccagg gtctgctctg attggttgga gtccgggctg tactgatcat taaatgattt     900
gattgccatc tctacttgga agagggtctg aggaagaaag agcaggcaat gtggggagtg     960
aggctcagag catggcccag caggggttc ccatccttcc tgcccttctc ttctcagacc    1020
tagggcttcg ggtccagcag aagggcacct cagaaacaga caccatctgc acctgtgaag    1080

```
aaggctggca ctgtacgagt gaggcctgtg agagctgtgt cctgcaccgc tcatgctcgc    1140
ccggctttgg ggtcaagcag attggtaagt ggctcatctg ggaatcagtt ttggaggggg    1200
acagaggagc ttagggccca aggtgagggg ctgggcagtg ggcacttagc cccagaggca    1260
gaggaagcag aggctccaac ctatgtcggt atccccactg gagtgagctg cagacgggac    1320
cttgttcatt ctgccttctg ccatggggat ctgcctttga agggcaatgg gagaagtcct    1380
cctggggact gcagctgtcg ggggcagtac cacatcgggg gaagagtgct caaggcagga    1440
gctcttcccg tcctgcctgg ccactggctg ccttgtgagc cggacaggtg gtccactgtg    1500
atggttaatg tccccctccc cacccactcc cagctacagg ggtttctgat accatctgcg    1560
agccctgccc agtcggcttc ttctccaatg tgtcatctgc tttcgaaaaa tgtcacccct    1620
ggacaaggta taagcactca tcccttgtgt ttcctgctct aagagtggca tggagctgcc    1680
tccattctct ccagccacct gtcctgtccc tgctcccaga ggtccacaca cactcatgta    1740
cttgtgaagc atctgcagag tggcctcatg gccaaccaga caggcacatt tccacatttt    1800
ttttgcctgc tgtctctttg aggtaataga cactgttgat ctctcgcttc atgagagcct    1860
cctatcttgg gggtattggg acacttattt tagctttcct tctgcccctc ctgcttctcc    1920
tcagttttcc tcgtcttgct ttcacccttac ctggcttttct agggctttct gggctctggg    1980
tgctcaccct gagggcctcc ctctcttacc tccaactcca aacccacacc aggtcctgcc    2040
actggctgtc tacgtgtttt gggaacttac tgtctccact gttgtcactt tagtttgggc    2100
ctcatcactg tggtctgggt gatgcctttt ctgcctcctg gcctccctgc ctctgtctct    2160
cccctcctgc tggttctgtc tccatcctct tgccaacatg agcgttcgac agtttctttc    2220
aaatcatgac actctcctat ttgagatgct tcctgtctct ctgttggaac taagactcct    2280
tagcatggca cccaaccttc ctgttgcatt tcctgctctc tttcctgcat cgcatagctt    2340
catgctactt gcaatcctct gaacacactg ttcattctct tccatcaaac tcatctgcct    2400
ggaataccct aaacatgggc cccaggccag gcgcggtggc tcttgcctgt aatctcagca    2460
ctttggatgc caaggcgggt ggatcacttg aggtcaggag ttcaagacca gccagcacaa    2520
catggtaaaa acccatctct actaaaaata ccaaaaaatt agctgggtgt ggtggtgggc    2580
gcctgtaatc ccagctcctc gggaggctga ggcaggagaa tcacttgaac ccggaaggtg    2640
gagtttgcag tgagccaaga tagcgccact gcactccagc ctgggcaaca gagcgacatt    2700
ctgtctcaaa aaacaaacac ctgccccatt aacttttgc atttgatttt taaaaatggg    2760
caagataggc acatgggaca gaaggcacaa aagagccaaa gtgatgtctt tctcccatcc    2820
ctgcccctta ggctcccagt tctttctgga gggagccatt gttccttgca tatccttcca    2880
gagattctac atataaacaa accaacacac acacacacac acacaaacac acacaaaatt    2940
tccctccttt tactttttgca caaataggag tatacatttt atttgttaac tgtctgcctt    3000
tccctaatag attgaaaatt ccttaaatgt agaaacttgg cctttttttt ttcttccatt    3060
gatacatccc ctatacctgg aacagtacct gacgcatggt aggtgcttaa attttttactg    3120 ataaatgttg actgataact ggaggcacca ctggtatagt ttttttttttt ttttttttt    3180 ttttttttt ttgagacaga gtctcactct gtcgcccagg ctggagtgca gtggcgcaat    3240
ctcggctcac tgcaagctct gcctcccagg ttcacgccat tctcctgcct cagcctcctg    3300
agtagctggg actataggcg cccgccacca cacccggcta atttttttgt atttttagta    3360
gagacggcgt ttcaccgtgt tagccaggat ggtcttgatc tcctgacctc gtgatccgtc    3420
tgccttggcc tcccaaagtg ctgggattac aggcgtgagc caccgtgccc ggccaccagt    3480
```

```
ggtatagtat taatggaatc agtgcattgg cttacgtatc tgattacagc tcagtaagtg   3540
tgtgaccctc actgagcctc agtctcctca tctgaaaaat gggaatgacc ttcatttcac   3600
aaggcttgag ctaaaaacat gtaaagtgta ttgtaaattc ctgaatgctc tactcatgta   3660
agactaaagt aggccgggcg tggtggctca cacctgtaat gcagcactt tgggaggccg    3720 aggagggcag atcatgaggt caagagatcg agaccatcct ggctaatatg gtaaaaccct   3780
gtctctacta aaatacaaa aattagctgg gcgtggtggc gcacatctgt agtcccagct    3840
actcaggagg cggaggcagg agaattgctt gaacctggga ggtggaggtt gcagtgagct   3900
gagatcgcgc cactgcattc cagccagtct ggcgaaagag caagactctg tctcaaaaaa   3960
aaaaaaaaaa aaaaaaaaag actaaagtac atggtttctt caaagcttct ctctctttct   4020
cccaccttag atgattttc ctttgcaatg tcctgtgtcc attccgcccc actcctcctg    4080
gggccacctg gaccaggtct tcatcatctc atatctatat gtttgctgtg tctcctggct   4140
ggccactctt ctgtaatttc tcctcctctg agctctctgg gcagctgaat cttctcacta   4200
gtgaagtcgc ctggttggat gctgatgaga ctgaccagct gaatccagtt gaaaacttca   4260
cacttggcag tgatctggtt ctaaagacac aattttccat agtttcctaa caccatcctg   4320
catgccacct gccttatttc cccacatcac atcgtcccac ttagcgggac tgcactgctg   4380
atccaaattt tacatccttt agggcccact caggtcatat gtcctcaggg aagtctttct   4440
ggaagaacct taaaccagag gttctcaaca gggggcagtt ttgctccctg tggaacgttt   4500
gccaatgtct ggacacattt cattcgtcac aaacggagag ggggatgcta cagggatctg   4560
gcggatagag gccagggatg ctgctgaaca tctgcaatgc ataggacagc ccaccccccac  4620 ccccacaccc ccagtaaata atgatccagc ccaagtgtca ctggtgctga cgttgagtaa   4680
ccctatctta agctgaactc atcatctctc cattccagcc ttggtggatt ctgtctcctc   4740
tgaaccattc ccatctcact ttagcctacc tagatcacaa agcttggcac tcattataga   4800
ctcccctatt tattactcct tcaagatgtg caagaatctt ttctctgcac tttttaagttc  4860 tgtaagaaga gtctgtgtcg ttcctataat aaccagcata ggacgttgca cgtgttgtgt   4920
gctcagtgaa cctggatttg ttgattgttg actgactcac tctagagttg gaaatcttat   4980
gcttggggaa acttaatatc tctttctttc tctgtgtgtg tgcatttgtg cacgtgtctg   5040
tgcatagctg tgagaccaaa gacctggttg tgcaacaggc aggcacaaac aagactgatg   5100
ttgtctgtgg tgagtcctgg acaatgggcc ctggagaaag cctaggaagg tgggaactga   5160 aggggagat gaggcacaca ggaacactgg atggaaaaa ggggagggga ggcagtttgg    5220
gggtgtggta tcacagctct gccacttatc ttgggagtct gggcaaatca cttcccctct   5280
cttagcctca gtttcttcat ctgtaaaatg ggatgataac agcacttcct tagtaggttt   5340 tgatttaga gtgagaaggt tggcctacag taaagatcag ataatgtaaa tcagtgaaaa    5400
aggtcagggg taagaaaatt acattctctt tacctaacgc taaatgacca gttaatgggt   5460
gcagcacacc aacatggtac atgtatacat atgtaacaaa cctgcacatt atgcacatgt   5520
accctaaagc ttaaagtata ataataataa aatttaaaaa aacgaaaaat acattctctt   5580 tgcttttct caaaatgtac tttcctcttt gtagggctgg gactagaatg aggtgagcaa    5640
ggcacttgcc ctcgggcgca atatttaaga aggtgccata aaagtgtagt aatcaaggta   5700
aattcatttt gatgcaatat ttttaaaaat aaaaattaat gcaaagaaat ccatgatgag   5760
caagatagca acatttttaaa taagaacag gatccgaccc tgtgtttgca tgaccctgcc    5820
```

```
tcactcacct caccctaatc ctggccctgg ttccagtaaa aggaataggc agccagcctg    5880
caggccgtag tttgctgact tggtgtccgc ctgatgattt tcaaaatatg cattaaaag    5940 aatgtttacc ttgatgactg agtgttttgg acatcctttt caattttgtc ctgaaacaat    6000
ttcatccctt gcctcacgct agtctccgcc ctgccttttg gtctttcttt tattttccca    6060
ctttgaaaaa aaaattcggc atgagaaata ctttacctt ccctccact cttctatacc    6120 aaaagcaaca tgcagacatg aatcatgcta gacctcggca ttgggcagag agcagggagt    6180
ggcggggagc atggtgagca ggtggtgaca gccactgcca ccactcgctt ctagatggtt    6240
cccaggtggg gaggctgcca actggaaccc agtcttccca gtttgtaaga gaaatcagat    6300
gtctaggttt gaatatgtga tctcccagtt taaaaatgtc ggcaaatatt tccaaacgtt    6360
aagaaaatgt tctggctcct ttaaagacat ctgccagcca catttcccca aggaccgcgg    6420
tttgaacctt ctgatgtaga tgagctctga cattggaaga ttctggagtc tgacaagtca    6480
cagcaggttg agggtaggga gaaactgcag gtgaggggtg catgctgaag tcctgatttc    6540
tccaggtccc caggatcggc tgcgagccct gctggtcatt cctgtcgtga tgggcatcct    6600
catcaccatt ttcggggtgt ttctctatat cagtgagtgc tcaggagagg aaagggaggg    6660
agggttcagc cctgtcgaac cagcctcctg actcaccctc gcaatgtccc acacccttc    6720 ttcttctcac tagaaaaggt ggtcaagaaa ccaaaggata atgaggtaag ccatccctga    6780
gggagagatg ctggaaagag tgactggtgg cagggaggg aggctcacgg cgtagggaga    6840
cagactcagt aagcagagag ctt                                            6863

<210> SEQ ID NO 25
<211> LENGTH: 870
<212> TYPE: DNA
<213> ORGANISM: Artificial Sequence
<220> FEATURE:
<223> OTHER INFORMATION: Homo sapiens and Mus musculus

<400> SEQUENCE: 25
atggtgtctt tgcctcggct gtgcgcgcta tggggctgct tgttgacagc ggtccatcca      60
gaaccaccca ctgcatgcag agaaaaacag tacctaataa acagtcagtg ctgttctttg     120
tgccagccag gacagaaact ggtgagtgac tgcacagagt tcactgaaac ggaatgcctt     180
ccttgcggtg aaagcgaatt cctagacacc tggaacagag agacacactg ccaccagcac     240
aaatactgcg acccccaacct agggcttcgg gtccagcaga agggcacctc agaaacagac     300
accatctgca cctgtgaaga aggctggcac tgtacgagtg aggcctgtga gagctgtgtc     360
ctgcaccgct catgctcgcc cggctttggg gtcaagcaga ttgctacagg ggtttctgat     420
accatctgcg agcccgccc agtcggcttc ttctccaatg tgtcatctgc tttcgaaaaa     480
tgtcacccct ggacaagctg tgagaccaaa gacctggttg tgcaacaggc aggcacaaac     540
aagactgatt tgtctgtgtg gtccccaggat cggctgcgag ccctgctggt cattcctgtc     600
gtgatgggca tcctcatcac catttttcggg gtgtttctct atatcaaaaa ggtggtcaag     660
aaaccaaagg ataatgagat cttacccct gcggctcgac ggcaagatcc ccaggagatg     720
gaagattatc ccggtcataa caccgctgct ccagtgcagg agacgctgca cgggtgtcag     780
cctgtcacac aggaggatgg taaagagagt cgcatctcag tgcaggagcg gcaggtgaca     840
gacagcatag ccttgaggcc cctggtctga                                      870

<210> SEQ ID NO 26
<211> LENGTH: 1683
```

```
<212> TYPE: DNA
<213> ORGANISM: Artificial Sequence
<220> FEATURE:
<223> OTHER INFORMATION: Homo sapiens and Mus musculus

<400> SEQUENCE: 26
agcagggact ttggagtgac ttgtggcttc agcaggagcc ctgtgatttg gctcttctga    60
tctcgccctg cgatggtgtc tttgcctcgg ctgtgcgcgc tatggggctg cttgttgaca   120
gcggtccatc cagaaccacc cactgcatgc agagaaaaac agtacctaat aaacagtcag   180
tgctgttctt tgtgccagcc aggacagaaa ctggtgagtg actgcacaga gttcactgaa   240
acggaatgcc ttccttgcgg tgaaagcgaa ttcctagaca cctggaacag agagacacac   300
tgccaccagc acaaatactg cgaccccaac ctagggcttc gggtccagca aagggcacc   360
tcagaaacag acaccatctg cacctgtgaa aaggctggc actgtacgag tgaggcctgt   420
gagagctgtg tcctgcaccg ctcatgctcg cccggctttg gggtcaagca gattgctaca   480
ggggtttctg ataccatctg cgagcccgc ccagtcggct tcttctccaa tgtgtcatct   540
gctttcgaaa aatgtcaccc ttggacaagc tgtgagacca agacctggt tgtgcaacag   600
gcaggcacaa acaagactga tgttgtctgt ggtccccagg atcggctgcg agccctgctg   660
gtcattcctg tcgtgatggg catcctcatc accatttcg gggtgtttct ctatatcaaa   720
aaggtggtca gaaaccaaa ggataatgag atcttacccc ctgcggctcg acggcaagat   780
ccccaggaga tggaagatta tcccggtcat aacaccgctg ctccagtgca ggagacgctg   840
cacgggtgtc agcctgtcac acaggaggat ggtaaagaga gtcgcatctc agtgcaggag   900
cggcaggtga cagacagcat agccttgagg cccctggtct gaaccctgga actgctttgg   960
aggcgatggc tcggctcggg agcaggggcc tggctctgag gactgcttgc tgacctttga  1020
agtttgagat gagccaagac agagcccagt gcagctaact ctcatgcctg cccctatca   1080
tttctcaact tgctttttaa ggatggaggg agagctcggg catcggggct ccacagtgat  1140
acctaccaag tgcagcagtg caggacccag agtcgtcttg ctgcggcgtt cactgtaagg  1200
agtcatggac acaggagtcc gtggcccaca gcttgtgctg ctagagggca cctggttgcc  1260
catcagcagg gtactggcta aataaatctg taattattta taatgaca tctcagaaac  1320
tctagcaggt ggggcagaaa acaggtagta gaatgatggg tagagaaata gcttttaaaa  1380
cacattccaa ggcaggtaag atggcttttg tgagtaaagg agcttgctgc caaacccgg  1440
ttacctgatt ttgatccctg ggacttcatg gtaaagggaa gagaaccaaa tccagagggt  1500
tgtcatttga cctccatgtg tgctctgtgg taatgtaccc cgtgtgtgca catgtgcaca  1560
tatcctaaaa tggatgtggt ggtgtattgt agaaattatt taatcccgcc ctggggtttc  1620
tacctgtgtg ttaccattta gttccttgaat aaaagacaca ctcaacccttt atatttacaa  1680
taa                                                                1683

<210> SEQ ID NO 27
<211> LENGTH: 289
<212> TYPE: PRT
<213> ORGANISM: Artificial Sequence
<220> FEATURE:
<223> OTHER INFORMATION: Homo sapiens and Mus musculus

<400> SEQUENCE: 27

Met Val Ser Leu Pro Arg Leu Cys Ala Leu Trp Gly Cys Leu Leu Thr
1               5                   10                  15

Ala Val His Pro Glu Pro Pro Thr Ala Cys Arg Glu Lys Gln Tyr Leu
```

|  |  |  | 20 |  |  |  |  | 25 |  |  |  |  | 30 |  |
|---|---|---|---|---|---|---|---|---|---|---|---|---|---|---|

Ile Asn Ser Gln Cys Cys Ser Leu Cys Gln Pro Gly Gln Lys Leu Val
    35      40      45

Ser Asp Cys Thr Glu Phe Thr Glu Thr Glu Cys Leu Pro Cys Gly Glu
 50      55      60

Ser Glu Phe Leu Asp Thr Trp Asn Arg Glu Thr His Cys His Gln His
65      70      75      80

Lys Tyr Cys Asp Pro Asn Leu Gly Leu Arg Val Gln Gln Lys Gly Thr
     85      90      95

Ser Glu Thr Asp Thr Ile Cys Thr Cys Glu Glu Gly Trp His Cys Thr
   100      105      110

Ser Glu Ala Cys Glu Ser Cys Val Leu His Arg Ser Cys Ser Pro Gly
    115      120     125

Phe Gly Val Lys Gln Ile Ala Thr Gly Val Ser Asp Thr Ile Cys Glu
   130      135      140

Pro Cys Pro Val Gly Phe Phe Ser Asn Val Ser Ser Ala Phe Glu Lys
145      150      155      160

Cys His Pro Trp Thr Ser Cys Glu Thr Lys Asp Leu Val Val Gln Gln
     165      170      175

Ala Gly Thr Asn Lys Thr Asp Val Val Cys Gly Pro Gln Asp Arg Leu
    180      185      190

Arg Ala Leu Leu Val Ile Pro Val Val Met Gly Ile Leu Ile Thr Ile
   195      200      205

Phe Gly Val Phe Leu Tyr Ile Lys Lys Val Val Lys Lys Pro Lys Asp
   210      215     220

Asn Glu Ile Leu Pro Pro Ala Ala Arg Arg Gln Asp Pro Gln Glu Met
225      230      235      240

Glu Asp Tyr Pro Gly His Asn Thr Ala Ala Pro Val Gln Glu Thr Leu
     245      250      255

His Gly Cys Gln Pro Val Thr Gln Glu Asp Gly Lys Glu Ser Arg Ile
    260      265      270

Ser Val Gln Glu Arg Gln Val Thr Asp Ser Ile Ala Leu Arg Pro Leu
   275      280      285

Val

<210> SEQ ID NO 28
<211> LENGTH: 1542
<212> TYPE: DNA
<213> ORGANISM: Artificial
<220> FEATURE:
<223> OTHER INFORMATION: Mus musculus

<400> SEQUENCE: 28

| | | | | | |
|---|---|---|---|---|---|
| ctgctggaca | aacctcagag | agtggctgcc | tccgcccagg | ggcgaagcag | cagagagctg | 60 |
| agctgcaggc | agcttaggca | gttctccagg | gtggagtcct | tctgggcagg | gattggtgag | 120 |
| acttcatgct | caaggattgg | tgggttcgca | tagttctttt | atttttttccc | aactaggaag | 180 |
| tgggctcagg | cctttccccc | agctagagtt | tcactgttct | ttaaaaaaca | tcattttgtt | 240 |
| tttatttcat | gtgaattggt | gttttgcccc | gcatgtttct | ctgtgtgagg | gtgtcagatt | 300 |
| ccctggatct | ggagttacaa | ctggtggttg | tgagttgcca | tgtggatgct | gggaactgaa | 360 |
| cttgggtcct | ctgaaagagt | aaccagtgct | cttagccatt | gagccatctc | tccagctcct | 420 |
| ccaaatcctt | ttcttattca | tttaaaaaat | tacatgtatg | tatgtatgta | tgtatgtatg | 480 |
| tatgcatgtt | tgtacgcaca | cacacacaca | cacacacaca | cacggagatt | agatgctaac | 540 |

```
ttttgagagt tggttctctc cttccatttc tgggccttga aattctggtt atcagtcttg      600
gcagcaagcg ccttgattgg ctgagccatc tcgctccttg gttcttcaag gagtaagtct      660
ctggcgctag ctagatcata gttaatgcct tttttttttc ttttttcttt ttttgagaca      720
gggtttctct gtgtagcttt ggctgtcttg gaactcactc tgtagaccag gctggactca      780
cagagatctg cctgcctctg cctctggagt gctgggatta gaggcttatg ccaccacagt      840
tggccagtta acacctctga aagacttgct accaacccac cccaggctta aaagtaaaat      900
caagagcaga cagagcgaag gatctcagca aagaaagcta cgcatcgagg cttaataacc      960
ctgttatgaa tctgttgagt gtattttttag ggtttctttt aatttatagg aagtgatact     1020
tgctgacctc ttgatgcagc agtagaagat ttacagttaa aagaagtgtg cttaaattag     1080
caagaagcag ctcatagcat gggtggtccc cggatgttgt agaaacacat gttgagagtc     1140
ccgcccctgt ggactctgtt cagtgttgcc ctctgtgggg tgattcttat ctctttggtg     1200
gcagggagct ggggacagaa accgggagaa gggctgaggc cagcttgagc cagcagtctc     1260
gggactctgg aggaagaact ggagttctcc ctacctgctg cgtctttggg agcactgaag     1320
agtcctgtgc atctgttcgg attagagggt tctgcgttct tgctttggta gatggcagta     1380
agacgatgtg acaacagagt aaaaaaaaaa atagacctca cactctgggg gctcactttt     1440
ctgctttgga tttccacatc agctacagcc tgcgtcttgg ctaactttca acatgccggt     1500
ggaagatccc ttccagctgt ccacttctgt ttttaggtcc at                         1542

<210> SEQ ID NO 29
<211> LENGTH: 1475
<212> TYPE: DNA
<213> ORGANISM: Artificial
<220> FEATURE:
<223> OTHER INFORMATION: Mus musculus

<400> SEQUENCE: 29
cgagccctgc tggtcattcc tgtcgtgatg ggcatcctca tcaccatttt cggggtgttt       60
ctctatatca gtgagtgctc aggagaggaa agggagggag ggttcagccc tgtcgaacca      120
gcctcctgac tcaccctcgc aatgtcccac accccttctt cttctcacta gaaaaggtgg      180
tcaagaaacc aaaggataat gaggtaagcc atccctgagg gagagatgct ggaaagagtg      240
actggtgggc agggagggag gctcacggcg tagggagaca gactcagtaa gcagagagct      300
tgtattggat ccttgagtgt ggacccatgg aaaaggccca ttacacccac gctggtgggg      360
gcggggagag ggggggagga tggacacagg gatcttagga gcttgctagc caaccatggg      420
ctactccagg ttccaagaga aaccctgact cggaaaataa gggttaagag tgcaagaaga      480
cacaagatgt tgacctctag cctctaataa tgtgtacatg ggtgtgtgga ccctctacgc      540
catgagcata cacccaatac cacgccacac tccgcgcgcg cacatgcgcg cacacacatg      600
cccaaacagg tttagggtcc gttccctgga acatataggt gggctactcg cacccccacc      660
cagccctgct ctcagtctcc atcgcttcct cctactcaac tacttcccct tagggcagag      720
ctgggcacca ctggcagaga aactctggct gtgctttcct ccagccttga atgctgggga      780
tgggagtcgg cggcgggggg tggggtgggg ggtgggggt gggtggatcc cgccttcagg      840
ggccagtagg tggaaccaaa ggggcagttt ccctgctgg tctgcagtgg ctctggaaat      900
ttcctgccaa atttcatgtg tccagcaggg ggcagaaggc atccaagaaa tcagttttgg      960
tacaccccca tcctcccacc ccattggaaa ggacttgaag gagggattct attcctcaga     1020
```

-continued

| | |
|---|---|
| ggcagggtgg ctctgtggct agaggtgaca ttggacctta taccttgact ccccagatct | 1080 |
| tacccctgc ggctcgacgg caagatcccc aggagatgga agattatccc ggtcataaca | 1140 |
| ccgctgctcc agtgcaggag acgctgcacg ggtgtcagcc tgtcacacag gaggatggta | 1200 |
| aagagagtcg catctcagtg caggagcgg aggtgacaga cagcatagcc ttgaggcccc | 1260 |
| tggtctgaac cctggaactg cttttggaggc gatggctcgg ctcgggagca ggggcctggc | 1320 |
| tctgaggact gcttgctgac cttttgaagtt tgagatgagc caagacagag cccagtgcag | 1380 |
| ctaactctca tgcctgcccc ctatcatttc tcaacttgct tttttaaggat ggagggagag | 1440 |
| ctcgggcatc gggggtccac agtgatacct accaa | 1475 |

<210> SEQ ID NO 30
<211> LENGTH: 6329
<212> TYPE: DNA
<213> ORGANISM: Artificial
<220> FEATURE:
<223> OTHER INFORMATION: Homo sapiens

<400> SEQUENCE: 30

| | |
|---|---|
| ccagaaccac ccactgcatg cagagaaaaa cagtacctaa taaacagtca gtgctgttct | 60 |
| ttgtgccagc caggtgagat gccaaccctc tagccccatc atggagtccc cctttgcttt | 120 |
| ggtggcagac gcagacccca tatgttaact gtaaactcaa atctgaaacg acccatttcc | 180 |
| cagccctgct tcactgtcag aatgttctgg ttccctctct accaggtaaa actctgtcta | 240 |
| ccctgaacta gggatcccag cttctccatc ttcctcgcct gattatgaag gatccaagac | 300 |
| tttcatcttt gaatccccta ccctaaagcc tggcctgatc attgtgtggt tagtgtctga | 360 |
| ctcatggagt tggccagagc cctccctcat ttcctgatgt tttccaggac agaaactggt | 420 |
| gagtgactgc acagagttca ctgaaacgga atgccttcct tgcggtgaaa gcgaattcct | 480 |
| agacacctgg aacagagaga cacactgcca ccagcacaaa tactgcgacc ccagtgcgtg | 540 |
| cgctgttggg aaagggacgc ttgggaaccg ggctgatatt cccgacaatg cagccattct | 600 |
| aattttatgt agccagggtc tgctctgatt ggttggagtc cgggctgtac tgatcattaa | 660 |
| atgatttgat tgccatctct acttggaaga gggtctgagg aagaaagagc aggcaatgtg | 720 |
| gggagtgagg ctcagagcat ggcccagcag ggggttccca tccttcctgc ccttctcttc | 780 |
| tcagacctag ggcttcgggt ccagcagaag ggcacctcag aaacagacac catctgcacc | 840 |
| tgtgaagaag gctggcactg tacgagtgag gcctgtgaga gctgtgtcct gcaccgctca | 900 |
| tgctcgcccg gctttggggt caagcagatt ggtaagtggc tcatctggga atcagttttg | 960 |
| gaggggaca gaggagctta gggcccaagg tgaggggctg ggcagtgggc acttagcccc | 1020 |
| agaggcagag gaagcagagg ctccaaccta tgtcggtatc cccactggag tgagctgcag | 1080 |
| acgggacctt gttcattctg ccttctgcca tggggatctg cctttgaagg gcaatgggag | 1140 |
| aagtcctcct ggggactgca gctgtcgggg gcagtaccac atcgggggaa gagtgctcaa | 1200 |
| ggcaggagct cttcccgtcc tgcctggcca ctggctgcct tgtgagccgg acaggtggtc | 1260 |
| cactgtgatg gttaatgtcc ccctcccccac ccactcccag ctacaggggt ttctgatacc | 1320 |
| atctgcgagc cctgcccagt cggcttcttc tccaatgtgt catctgcttt cgaaaaatgt | 1380 |
| cacccttgga caaggtataa gcactcatcc cttgtgtttc ctgctctaag agtggcatgg | 1440 |
| agctgcctcc attctctcca gccacctgtc ctgtccctgc tcccagaggt ccacacacac | 1500 |
| tcatgtactt gtgaagcatc tgcagagtgg cctcatggcc aaccagacag gcacatttcc | 1560 |
| acatttttttt tgcctgctgt ctctttgagg taatagacac tgttgatctc tcgcttcatg | 1620 |

```
agagcctcct atcttggggg tattgggaca cttattttag cttcttct gcccctcctg      1680 cttctcctca gttttcctcg tcttgctttc accttacctg gctttctagg gctttctggg      1740
ctctgggtgc tcaccctgag ggcctccctc tcttacctcc aactccaaac ccacaccagg      1800
tcctgccact ggctgtctac gtgttttggg aacttactgt ctccactgtt gtcactttag      1860
tttgggcctc atcactgtgg tctgggtgat gccttttctg cctcctggcc tccctgcctc      1920
tgtctctccc ctcctgctgg ttctgtctcc atcctcttgc caacatgagc gttcgacagt      1980
ttctttcaaa tcatgacact ctcctatttg agatgcttcc tgtctctctg ttggaactaa      2040
gactccttag catggcaccc aaccttcctg ttgcatttcc tgctctcttt cctgcatcgc      2100
atagcttcat gctacttgca atcctctgaa cacactgttc attctcttcc atcaaactca      2160
tctgcctgga ataccttaaa catgggcccc aggccaggcg cggtggctct tgcctgtaat      2220
ctcagcactt tggatgccaa ggcgggtgga tcacttgagg tcaggagttc aagaccagcc      2280
agcacaacat ggtaaaaacc catctctact aaaaatacca aaaaattagc tgggtgtggt      2340
ggtgggcgcc tgtaatccca gctcctcggg aggctgaggc aggagaatca cttgaacccg      2400
gaaggtggag tttgcagtga gccaagatag cgccactgca ctccagcctg ggcaacagag      2460
cgacattctg tctcaaaaaa caaacacctg ccccattaac ttttttgcatt tgatttttaa      2520 aaatgggcaa gataggcaca tgggacagaa ggcacaaaag agccaaagtg atgtctttct      2580
cccatccctg cccccttaggc tcccagttct ttctggaggg agccattgtt ccttgcatat      2640
ccttccagag attctacata taaacaaacc aacacacaca cacacacaca caaacacaca      2700
caaaatttcc ctccttttac ttttgcacaa ataggagtat acattttatt tgttaactgt      2760 ctgccttttcc ctaatagatt gaaaattcct taaatgtaga aacttggcct ttttttttttc      2820 ttccattgat acatcccta tacctggaac agtacctgac gcatggtagg tgcttaaatt      2880
tttactgata aatgttgact gataactgga ggcaccactg gtatagtttt tttttttttt      2940
tttttttttt tttttttttg agacagagtc tcactctgtc gcccaggctg gagtgcagtg      3000
gcgcaatctc ggctcactgc aagctctgcc tcccaggttc acgccattct cctgcctcag      3060
cctcctgagt agctgggact ataggcgccc gccaccacac ccggctaatt tttttgtatt      3120
tttagtagag acggcgtttc accgtgttag ccaggatggt cttgatctcc tgacctcgtg      3180
atccgtctgc cttggcctcc caaagtgctg ggattacagg cgtgagccac cgtgcccggc      3240
caccagtggt atagtattaa tggaatcagt gcattggctt acgtatctga ttacagctca      3300
gtaagtgtgt gaccctcact gagcctcagt ctcctcatct gaaaaatggg aatgaccttc      3360
atttcacaag gcttgagcta aaaacatgta agtgtattg taaattcctg aatgctctac      3420
tcatgtaaga ctaaagtagg ccgggcgtgg tggctcacac ctgtaattgc agcactttgg      3480
gaggccgagg agggcagatc atgaggtcaa gagatcgaga ccatcctggc taatatggta      3540
aaaccctgtc tctactaaaa atacaaaaat tagctgggcg tggtggcgca catctgtagt      3600
cccagctact caggaggcgg aggcaggaga attgcttgaa cctgggaggt ggaggttgca      3660
gtgagctgag atcgcgccac tgcattccag ccagtctggc gaaagagcaa gactctgtct      3720
caaaaaaaaa aaaaaaaaa aaaaaagact aaagtacatg gtttcttcaa agcttctctc      3780
tctttctccc accttagatg attttccctt tgcaatgtcc tgtgtccatt ccgccccact      3840
cctcctgggg ccacctggac caggtcttca tcatctcata tctatatgtt tgctgtgtct      3900
cctggctggc cactcttctg taatttctcc tcctctgagc tctctgggca gctgaatctt      3960
```

```
ctcactagtg aagtcgcctg gttggatgct gatgagactg accagctgaa tccagttgaa    4020
aacttcacac ttggcagtga tctggttcta aagacacaat tttccatagt ttcctaacac    4080
catcctgcat gccacctgcc ttatttcccc acatcacatc gtcccactta gcgggactgc    4140
actgctgatc caaattttac atcctttagg gcccactcag gtcatatgtc ctcagggaag    4200
tctttctgga agaaccttaa accagaggtt ctcaacaggg ggcagttttg ctccctgtgg    4260
aacgtttgcc aatgtctgga cacatttcat tcgtcacaaa cggagagggg gatgctacag    4320
ggatctggcg gatagaggcc agggatgctg ctgaacatct gcaatgcata ggacagccca    4380
cccccacccc cacaccccca gtaaataatg atccagccca agtgtcactg gtgctgacgt    4440
tgagtaaccc tatcttaagc tgaactcatc atctctccat tccagccttg gtggattctg    4500
tctcctctga accattccca tctcacttta gcctacctag atcacaaagc ttggcactca    4560
ttatagactc ccctatttat tactccttca agatgtgcaa gaatcttttc tctgcacttt    4620
taagttctgt aagaagagtc tgtgtcgttc ctataataac cagcatagga cgttgcacgt    4680
gttgtgtgct cagtgaacct ggatttgttg attgttgact gactcactct agagttggaa    4740
atcttatgct tggggaaact taatatctct ttctttctct gtgtgtgtgc atttgtgcac    4800
gtgtctgtgc atagctgtga gaccaaagac ctggttgtgc aacaggcagg cacaaacaag    4860
actgatgttg tctgtggtga gtcctggaca atgggccctg gagaaagcct aggaaggtgg    4920
gaactgaagg gggagatgag gcacacagga acactggatg ggaaaagggg gaggggaggc    4980
agtttggggg tgtggtatca cagctctgcc acttatcttg ggagtctggg caaatcactt    5040
cccctctctt agcctcagtt tcttcatctg taaaatggga tgataacagc acttccttag    5100
taggttttga ttttagagtg agaaggttgg cctacagtaa agatcagata atgtaaatca    5160
gtgaaaaagg tcagggtaa gaaaattaca ttctctttac ctaacgctaa atgaccagtt    5220
aatgggtgca gcacaccaac atggtacatg tatacatatg taacaaacct gcacattatg    5280
cacatgtacc ctaaagctta aagtataata ataataaaat ttaaaaaaac gaaaaataca    5340
ttctctttgc ttttttctcaa aatgtacttt cctctttgta gggctgggac tagaatgagg    5400
tgagcaaggc acttgccctc gggcgcaata tttaagaagg tgccataaaa gtgtagtaat    5460
caaggtaaat tcattttgat gcaatatttt taaaaataaa aattaatgca aagaaatcca    5520
tgatgagcaa gatagcaaca ttttaaataa agaacaggat ccgaccctgt gtttgcatga    5580
ccctgcctca ctcacctcac cctaatcctg gccctggttc cagtaaaagg aataggcagc    5640
cagcctgcag gccgtagttt gctgacttgg tgtccgcctg atgattttca aaatatggca    5700
ttaaaagaat gtttaccttg atgactgagt gttttggaca tccttttcaa ttttgtcctg    5760
aaacaatttc atcccttgcc tcacgctagt ctccgccctg ccttttggtc tttcttttat    5820
tttcccactt tgaaaaaaaa attcggcatg agaaatactt taccttcccc ctccactctt    5880
ctataccaaa agcaacatgc agacatgaat catgctagac ctcggcattg ggcagagagc    5940
agggagtggc ggggagcatg gtgagcaggt ggtgacagcc actgccacca ctcgcttcta    6000
gatggttccc aggtggggag gctgccaact ggaacccagt cttcccagtt tgtaagagaa    6060
atcagatgtc taggtttgaa tatgtgatct cccagtttaa aaatgtcggc aaatatttcc    6120
aaacgttaag aaaatgttct ggctcccttta aagacatctg ccagccacat ttccccaagg    6180
accgcggttt gaaccttctg atgtagatga gctctgacat tggaagattc tggagtctga    6240
caagtcacag caggttgagg gtagggagaa actgcaggtg aggggtgcat gctgaagtcc    6300
tgatttctcc aggtccccag gatcggctg                                      6329
```

<210> SEQ ID NO 31
<211> LENGTH: 39
<212> TYPE: DNA
<213> ORGANISM: Artificial Sequence
<220> FEATURE:
<223> OTHER INFORMATION: PCR primer

<400> SEQUENCE: 31
ctagctcgag ctgctggaca aacctcagag agtggctgc                    39

<210> SEQ ID NO 32
<211> LENGTH: 50
<212> TYPE: DNA
<213> ORGANISM: Artificial Sequence
<220> FEATURE:
<223> OTHER INFORMATION: PCR primer

<400> SEQUENCE: 32
ctgcatgcag tgggtggttc tggatggacc taaaaacaga agtggacagc         50

<210> SEQ ID NO 33
<211> LENGTH: 52
<212> TYPE: DNA
<213> ORGANISM: Artificial Sequence
<220> FEATURE:
<223> OTHER INFORMATION: PCR primer

<400> SEQUENCE: 33
gctgtccact tctgttttta ggtccatcca gaaccaccca ctgcatgcag ag      52

<210> SEQ ID NO 34
<211> LENGTH: 47
<212> TYPE: DNA
<213> ORGANISM: Artificial Sequence
<220> FEATURE:
<223> OTHER INFORMATION: PCR primer

<400> SEQUENCE: 34
ctagggtacc atcgactagt atctttcgaa agcagatgac acattgg            47

<210> SEQ ID NO 35
<211> LENGTH: 28
<212> TYPE: DNA
<213> ORGANISM: Artificial Sequence
<220> FEATURE:
<223> OTHER INFORMATION: PCR primer

<400> SEQUENCE: 35
ccaatgtgtc atctgctttc gaaaaatg                                28

<210> SEQ ID NO 36
<211> LENGTH: 27
<212> TYPE: DNA
<213> ORGANISM: Artificial Sequence
<220> FEATURE:
<223> OTHER INFORMATION: PCR primer

<400> SEQUENCE: 36
ggcgacttca ctagtgagaa gattcag                                 27

<210> SEQ ID NO 37
<211> LENGTH: 27
<212> TYPE: DNA
<213> ORGANISM: Artificial Sequence
<220> FEATURE:

<223> OTHER INFORMATION: PCR primer

<400> SEQUENCE: 37
ctgaatcttc tcactagtga agtcgcc                                      27

<210> SEQ ID NO 38
<211> LENGTH: 46
<212> TYPE: DNA
<213> ORGANISM: Artificial Sequence
<220> FEATURE:
<223> OTHER INFORMATION: PCR primer

<400> SEQUENCE: 38
acaggaatga ccagcagggc tcgcagccga tcctggggac ctggag                 46

<210> SEQ ID NO 39
<211> LENGTH: 46
<212> TYPE: DNA
<213> ORGANISM: Artificial Sequence
<220> FEATURE:
<223> OTHER INFORMATION: PCR primer

<400> SEQUENCE: 39
tccaggtccc caggatcggc tgcgagccct gctggtcatt cctgtc                 46

<210> SEQ ID NO 40
<211> LENGTH: 35
<212> TYPE: DNA
<213> ORGANISM: Artificial Sequence
<220> FEATURE:
<223> OTHER INFORMATION: PCR primer

<400> SEQUENCE: 40
ctagggtacc ttggtaggta tcactgtgga ccccc                             35

<210> SEQ ID NO 41
<211> LENGTH: 25
<212> TYPE: DNA
<213> ORGANISM: Artificial Sequence
<220> FEATURE:
<223> OTHER INFORMATION: PCR primer

<400> SEQUENCE: 41
gaagtgttac agctccgctc tgagg                                        25

<210> SEQ ID NO 42
<211> LENGTH: 25
<212> TYPE: DNA
<213> ORGANISM: Artificial Sequence
<220> FEATURE:
<223> OTHER INFORMATION: PCR primer

<400> SEQUENCE: 42
agctcaagcc ttgtgaaatg aaggt                                        25

<210> SEQ ID NO 43
<211> LENGTH: 25
<212> TYPE: DNA
<213> ORGANISM: Artificial Sequence
<220> FEATURE:
<223> OTHER INFORMATION: PCR primer

<400> SEQUENCE: 43
aatggaatca gtgcattggc ttacg                                        25

```
<210> SEQ ID NO 44
<211> LENGTH: 25
<212> TYPE: DNA
<213> ORGANISM: Artificial Sequence
<220> FEATURE:
<223> OTHER INFORMATION: PCR primer

<400> SEQUENCE: 44
tttgggcagc aagctccttt actca                                          25

<210> SEQ ID NO 45
<211> LENGTH: 46
<212> TYPE: DNA
<213> ORGANISM: Artificial Sequence
<220> FEATURE:
<223> OTHER INFORMATION: PCR primer

<400> SEQUENCE: 45
gcatcaagct tggtaccgat gttctgcgtt cttgctttgg tagatg                   46

<210> SEQ ID NO 46
<211> LENGTH: 48
<212> TYPE: DNA
<213> ORGANISM: Artificial Sequence
<220> FEATURE:
<223> OTHER INFORMATION: PCR primer

<400> SEQUENCE: 46
acttaatcgt ggaggatgat ctcattatcc tttggtttct tgaccacc                 48

<210> SEQ ID NO 47
<211> LENGTH: 20
<212> TYPE: DNA
<213> ORGANISM: Artificial Sequence
<220> FEATURE:
<223> OTHER INFORMATION: PCR primer

<400> SEQUENCE: 47
acatgccggt ggaagatccc                                                20

<210> SEQ ID NO 48
<211> LENGTH: 20
<212> TYPE: DNA
<213> ORGANISM: Artificial Sequence
<220> FEATURE:
<223> OTHER INFORMATION: PCR primer

<400> SEQUENCE: 48
gagacgggac agcttggggt                                                20

<210> SEQ ID NO 49
<211> LENGTH: 24
<212> TYPE: DNA
<213> ORGANISM: Artificial Sequence
<220> FEATURE:
<223> OTHER INFORMATION: PCR primer

<400> SEQUENCE: 49
agacatctgc cagccacatt tccc                                           24

<210> SEQ ID NO 50
<211> LENGTH: 28
<212> TYPE: DNA
<213> ORGANISM: Artificial Sequence
<220> FEATURE:
<223> OTHER INFORMATION: PCR primer
```

<400> SEQUENCE: 50
ctcattatcc tttggtttct tgaccacc                28

<210> SEQ ID NO 51
<211> LENGTH: 25
<212> TYPE: DNA
<213> ORGANISM: Artificial Sequence
<220> FEATURE:
<223> OTHER INFORMATION: PCR primer

<400> SEQUENCE: 51
cttccacatg agcgtggtca gggcc                25

<210> SEQ ID NO 52
<211> LENGTH: 25
<212> TYPE: DNA
<213> ORGANISM: Artificial Sequence
<220> FEATURE:
<223> OTHER INFORMATION: PCR primer

<400> SEQUENCE: 52
ccaagggact attttagatg ggcag                25

<210> SEQ ID NO 53
<211> LENGTH: 26
<212> TYPE: DNA
<213> ORGANISM: Artificial Sequence
<220> FEATURE:
<223> OTHER INFORMATION: PCR primer

<400> SEQUENCE: 53
gaagctacaa gctcctaggt aggggg                26

<210> SEQ ID NO 54
<211> LENGTH: 23
<212> TYPE: DNA
<213> ORGANISM: Artificial Sequence
<220> FEATURE:
<223> OTHER INFORMATION: PCR primer

<400> SEQUENCE: 54
acgggttggc tcaaaccatt aca                23

<210> SEQ ID NO 55
<211> LENGTH: 25
<212> TYPE: DNA
<213> ORGANISM: Artificial Sequence
<220> FEATURE:
<223> OTHER INFORMATION: PCR primer

<400> SEQUENCE: 55
ccagggaggt ggcccactga taata                25

<210> SEQ ID NO 56
<211> LENGTH: 25
<212> TYPE: DNA
<213> ORGANISM: Artificial Sequence
<220> FEATURE:
<223> OTHER INFORMATION: PCR primer

<400> SEQUENCE: 56
actaacgcaa gcaggtccag ctccc                25

<210> SEQ ID NO 57
<211> LENGTH: 22

```
<212> TYPE: DNA
<213> ORGANISM: Artificial Sequence
<220> FEATURE:
<223> OTHER INFORMATION: sgRNA sequence

<400> SEQUENCE: 57
aaacggttta aagtcccgga tg                                            22

<210> SEQ ID NO 58
<211> LENGTH: 25
<212> TYPE: DNA
<213> ORGANISM: Artificial Sequence
<220> FEATURE:
<223> OTHER INFORMATION: PCR primer

<400> SEQUENCE: 58
cacccctgca tcctgcaatt tcaca                                         25

<210> SEQ ID NO 59
<211> LENGTH: 23
<212> TYPE: DNA
<213> ORGANISM: Artificial Sequence
<220> FEATURE:
<223> OTHER INFORMATION: sgRNA sequence

<400> SEQUENCE: 59
taggacaaac agtacctcca cga                                           23

<210> SEQ ID NO 60
<211> LENGTH: 23
<212> TYPE: DNA
<213> ORGANISM: Artificial Sequence
<220> FEATURE:
<223> OTHER INFORMATION: sgRNA sequence

<400> SEQUENCE: 60
aaactcgtgg aggtactgtt tgt                                           23

<210> SEQ ID NO 61
<211> LENGTH: 22
<212> TYPE: DNA
<213> ORGANISM: Artificial Sequence
<220> FEATURE:
<223> OTHER INFORMATION: sgRNA sequence

<400> SEQUENCE: 61
taggcatccg ggactttaaa cc                                            22
```